(12) United States Patent
Izumi et al.

(10) Patent No.: US 7,943,584 B2
(45) Date of Patent: *May 17, 2011

(54) MEDICINAL COMPOSITION CONTAINING DIABETES REMEDY

(75) Inventors: Masanori Izumi, Tokyo (JP); Akira Okuno, Tokyo (JP); Keiko Matsumura, Tokyo (JP)

(73) Assignee: Sankyo Company, Limited (JP)

( * ) Notice: Subject to any disclaimer, the term of this patent is extended or adjusted under 35 U.S.C. 154(b) by 813 days.

This patent is subject to a terminal disclaimer.

(21) Appl. No.: 11/572,752

(22) PCT Filed: Jul. 29, 2005

(86) PCT No.: PCT/JP2005/013912
§ 371 (c)(1),
(2), (4) Date: Jan. 26, 2007

(87) PCT Pub. No.: WO2006/011588
PCT Pub. Date: Feb. 2, 2006

(65) Prior Publication Data
US 2008/0039367 A1      Feb. 14, 2008

(30) Foreign Application Priority Data
Jul. 29, 2004     (JP) .................................. 2004-222419

(51) Int. Cl.
*A01N 43/04* (2006.01)
*A61K 31/70* (2006.01)
(52) U.S. Cl. ...................................................... 514/27
(58) Field of Classification Search .................... None
See application file for complete search history.

(56) References Cited

U.S. PATENT DOCUMENTS

| | | | |
|---|---|---|---|
| 4,687,777 | A | 8/1987 | Meguro et al. |
| 5,002,953 | A | 3/1991 | Hindley |
| 5,594,016 | A | 1/1997 | Ueno et al. |
| 5,783,568 | A | 7/1998 | Schlessinger et al. |
| 5,886,014 | A | 3/1999 | Fujita et al. |
| 6,166,219 | A | 12/2000 | Yamasaki et al. |
| 6,339,146 | B1 | 1/2002 | Ogawa et al. |
| 6,596,696 | B1 | 7/2003 | Uchida et al. |
| 2004/0006046 | A1 | 1/2004 | Uchida et al. |
| 2004/0006064 | A1 | 1/2004 | Robin et al. |
| 2006/0025350 | A1 | 2/2006 | Honda et al. |

FOREIGN PATENT DOCUMENTS

| | | |
|---|---|---|
| AU | 2004207726 B2 * | 3/2007 |
| WO | WO 99/62872 | 12/1999 |
| WO | WO 00/34241 | 6/2000 |
| WO | WO 00/50494 | 9/2000 |
| WO | WO 00/71540 | 11/2000 |
| WO | WO 01/21602 | 3/2001 |
| WO | WO 01/68603 | 9/2001 |
| WO | WO 01/94367 | 12/2001 |
| WO | WO 02/100813 | 12/2002 |
| WO | WO 03/004498 | 1/2003 |
| WO | WO 2004/067542 | 8/2004 |
| WO | WO 2005/003135 | 1/2005 |

OTHER PUBLICATIONS

Florence et al. Treatment of Type 2 Diabetes Mellitus—May 15, 1999, American Academy of Family Physicians.*
Moller, Nature vol. 414, Dec. 13, 2001, pp. 821-827.*
Deacon et al. Expert Opin. Investig. Drugs (2004) 13(9): 1091-1102.*
The Merck Manuals Online Medical Library, Diabetes Mellitus, May 2010.*
Uchida et al., "Synthesis of New N-Containing Maltooligosaccharides, α-Amylase Inhibitors, and Their Biological Activites," *Chem. Pharm. Bull.*, 47(2), 187-193, 1999.
Yamashita et al., "New Polyhydroxylated Pyrrolidine, Piperidine, and Pyrrolizidine Alkaloids from Scilla *Sibirica*," *J.Nat. Prod.*, vol. 65, 1875-1881, 2002.
Published International Search Report for Application No. PCT/JP2005/013912 completed on Oct. 6, 2005 and mailed on Oct. 25, 2005. English language abstract of WO 2004/067542; Published Date: Jan. 13, 2005.
Greene, T.W., et al., Protective Groups in Organic Synthesis, Third Edition, John Wiley & Sons, Inc., 1999. In particular, Chapter 2, pp. 17-246.
Sugawara, S., et al., "Stereoselective Synthesis of 1- and 2-*O*-α-D-Cellotriosyl-3-deoxy-2(*R*)- and 2(*S*)-glycerols Related to Rhynchosporoside", Agric. Biol. Chem, 1986, 50, pp. 2261-2272.
Koto, S. et al., "2-Methoxyethyl Group for Protection of Reducing Hydroxyl Group of Aldose", Bull. Chem. Soc. Jpn., 1989, 62, pp. 3549-3566.
Kovac, P., "A short synthesis of 2-deoxy-2-fluoro-D-glucose", Carbohydrate Research, 153, 1986, pp. 168-170.

(Continued)

*Primary Examiner* — Shaojia Anna Jiang
*Assistant Examiner* — Layla Bland
(74) *Attorney, Agent, or Firm* — Brandon T. Schurter; Locke Lord Bissell & Liddell LLP

(57) ABSTRACT

A pharmaceutical composition effective for the prophylaxis and treatment of diabetes is provided. This pharmaceutical composition comprises the combination of an α-amylase inhibitor selected from a compound represented by the following general formula (I):

[Chemical formula 1]

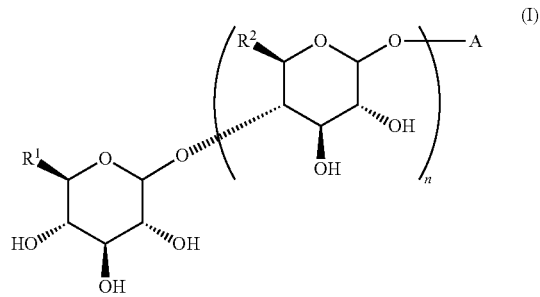

[wherein A represents, for example, a cyclic group, etc. $R^1$ and $R^2$ represent an alkyl group, hydroxymethyl group, etc., and n represents 1 or 2], or a pharmacologically acceptable salt or ester thereof, and at least one type of drug selected from an insulin sensitizer, an insulin secretagogue, a biguanide drug, an insulin preparation and a DPP-IV inhibitor.

25 Claims, 3 Drawing Sheets

OTHER PUBLICATIONS

Kovac, P., et al., "Synthesis and N.M.R. Spectra of Methyl 2-Deoxy-2-Fluoro- and 3-Deoxy-3-fluoro-α- and β-D-Glucopyranosides", Carbohydrate Research, 169, 1987, pp. 23-34.

Kayakiri, H. et al., "Structure and Synthesis of Nectrisine, a New Immunomodulator Isolated from a Fungus", Chem. Pharm. Bull., 1991, 39, pp. 2807-2812.

Totani, K. et al., "Highly Diastereoselective 1,4-Addition of an Organocuprate to Methyl α-D-Gluco-, α-D-Manno-, or α-D-Galactopyranosides Tethering an α,β-Unsaturated Ester. Novel Asymmetric Access to β-C-Substituted Butanoic Acids", J. Org. Chem., 2001, 66, pp. 5965-5975.

Fleet, G.W.J., et al., "Enantiospecific Synthesis of Deoxymannojirimycin, Fagomine and 2R,5R-Dihydroxymethy1-3R,4R-Dihydroxypyrrolidine from d-glucose", Tetrahedron Letters, vol. 26, 1985, pp. 1469-1472.

Fleet, G.W.J., et al., "The Synthesis from D-xylose of the Potent and Specific Enantiomeric Flucosidase Inhibitors, 1,4-Dideoxy-1,4-imino-D-arabinitol and 1,4-dideoxy-1,4-imino=1-arabinitol", Tetrahedron, 1986, vol. 42, pp. 5685-5692.

* cited by examiner (FIG. 1)
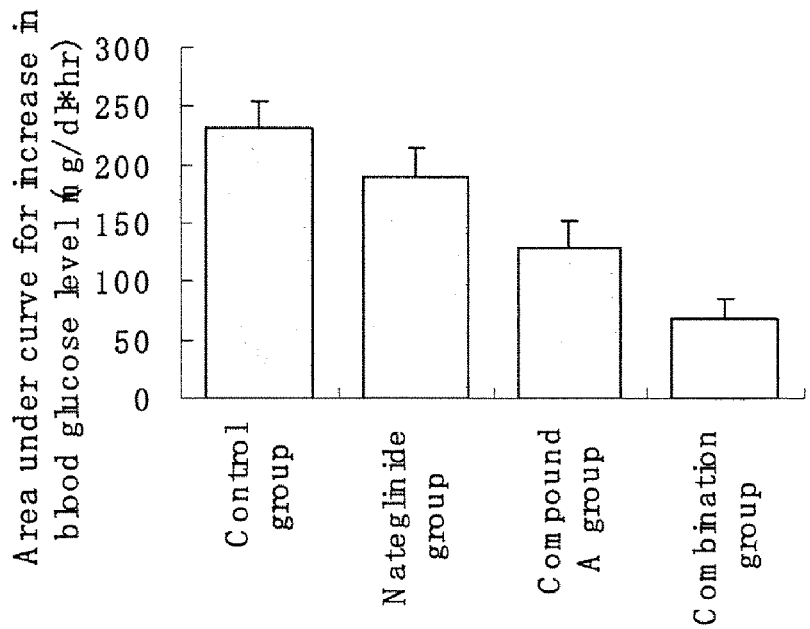
(FIG. 2)
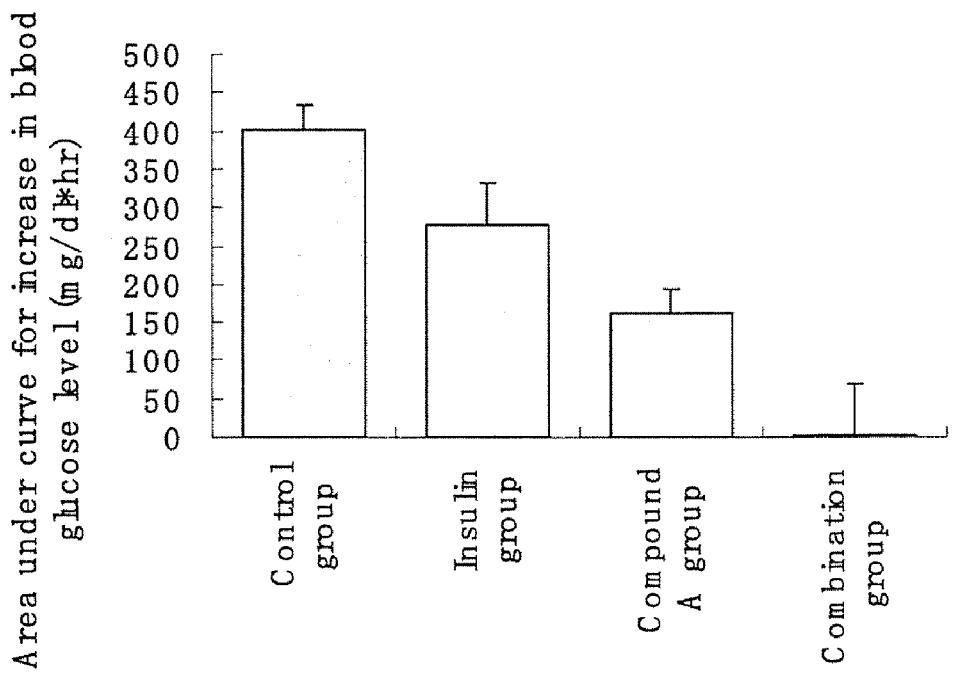

(FIG. 3)
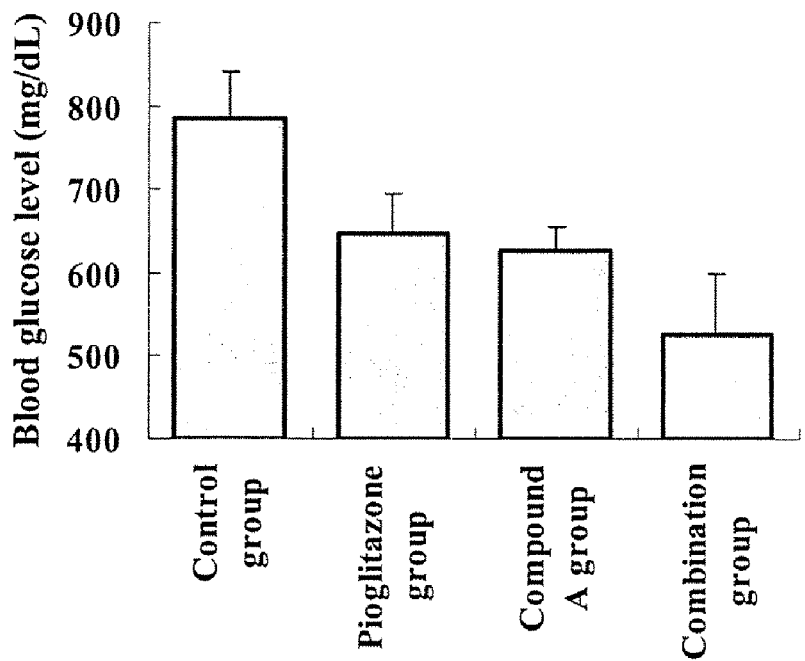
(FIG. 4)
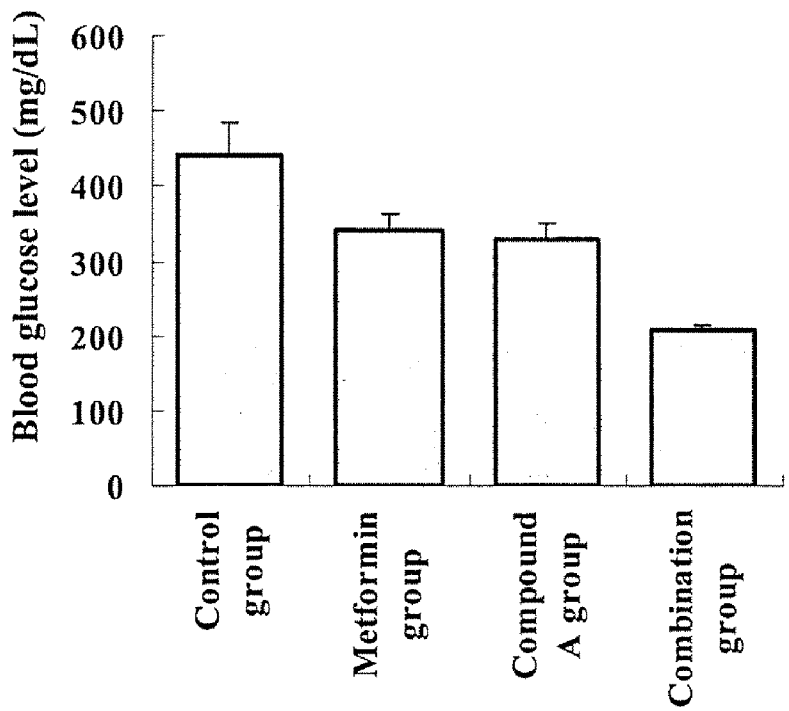

(FIG. 5)
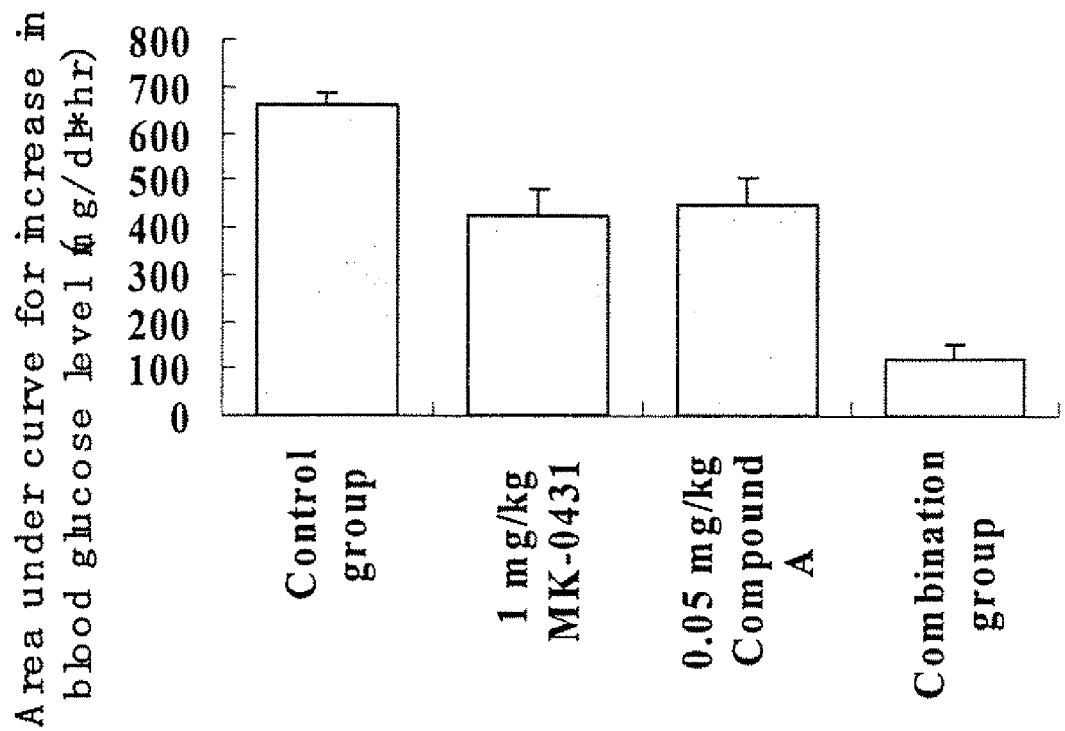

US 7,943,584 B2

MEDICINAL COMPOSITION CONTAINING DIABETES REMEDY

TECHNICAL FIELD

The present invention relates to a pharmaceutical composition combining an α-amylase inhibitor and another diabetes prophylactic and/or therapeutic drug having a different mechanism of action (preferably, the pharmaceutical composition is an agent for the treatment and/or prophylaxis of postprandial hyperglycemia and diabetes).

Moreover, the present invention relates to the use of the aforementioned compound for production of the aforementioned pharmaceutical, or a method for preventing and/or treating the aforementioned diseases by administering the aforementioned pharmaceutical to a warm-blooded animal (preferably to a human).

BACKGROUND ART

α-amylase inhibitors suppress decomposition of carbohydrates by inhibiting α-amylase, a digestive enzyme, and are known to generate effects that lower blood glucose levels (see, for example, Patent documents 1 to 3).

However, a pharmaceutical composition having the specific combination of the present invention is completely unknown.

[Patent document 1]
International Patent Publication WO 00/50434
[Patent document 2]
International Patent Publication WO 01/94367
[Patent document 3]
Japanese Patent Application (Kokai) No. 2004-250446

DISCLOSURE OF THE INVENTION

Problem to be Solved by the Invention

Diabetes is a chronic illness. Since it also has a complex pathology, there are many cases in which symptoms progress while accompanied by numerous types of complications. Thus, although it is necessary to select a drug that is most suited to the symptoms of each patient at that time, in the case of using individual drugs alone, there are cases in which adequate effects are not obtained depending on the symptoms. In addition, since there are also various problems such as the appearance of adverse side effects from increasing the dose or prolonged administration, there are many cases in which selection of such a drug is difficult in the clinical setting.

As a result of conducting extensive studies on a diabetes preventive and/or therapeutic drug having few adverse side effects even during prolonged drug administration and effective in numerous diabetes patients in consideration of the aforementioned circumstances, the inventors of the present invention found that this object can be achieved by combining an α-amylase inhibitor as an essential component with another diabetes preventive and/or therapeutic drug having a different mechanism of action, thereby leading to completion of the present invention.

Means for Solving the Problem

Namely, the present invention relates to:
(1) A pharmaceutical composition comprising a combination of an α-amylase inhibitor selected from a compound represented by the following general formula (I):

[Chemical formula 1]

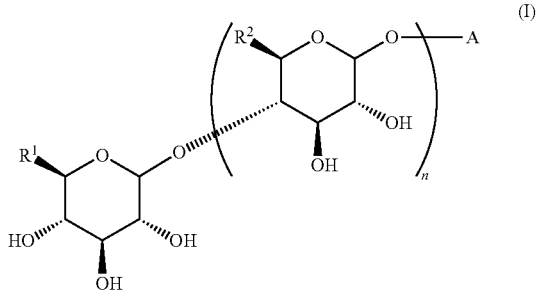

(I)

[wherein A represents the following general formula (A1), (A2) or (A3),

[Chemical formula 2]

(A1)

(A2)

(A3)

$R^1$ and $R^2$ may respectively be the same or different and represent a $C_1$-$C_6$ alkyl group, hydroxymethyl group, $C_1$-$C_6$ alkoxymethyl group or $C_1$-$C_6$ haloalkyl group, $R^3$, $R^4$, $R^5$ and $R^6$ may respectively be the same or different and represent a $C_1$-$C_6$ alkyl group, $C_1$-$C_6$ alkoxy group, $C_1$-$C_6$ hydroxyalkyl group, $C_1$-$C_6$ haloalkyl group, amino group (wherein said amino group may be substituted with 1 or 2 $C_1$-$C_6$ alkyl groups or $C_1$-$C_6$ hydroxyalkyl groups), hydroxyl group, hydrogen atom or halogen atom, $R^7$ represents a $C_1$-$C_6$ alkyl group, $C_1$-$C_6$ alkoxy group, $C_1$-$C_6$ hydroxyalkyl group, $C_1$-$C_6$ haloalkyl group, hydroxyl group or hydrogen atom, and n represents an integer of 1 or 2], or a pharmacologically acceptable salt or ester thereof, and at least one type of drug selected from an insulin sensitizer, an insulin secretagogue, a biguanide drug, an insulin preparation and a DPP-IV inhibitor.

(2) A pharmaceutical composition comprising a combination of an α-amylase inhibitor selected from a compound represented by the following general formula (I):

[Chemical formula 3]

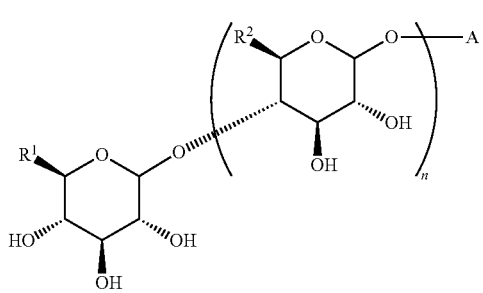

(I)

[wherein A represents the following general formula (A1), (A2) or (A3),

[Chemical formula 4]

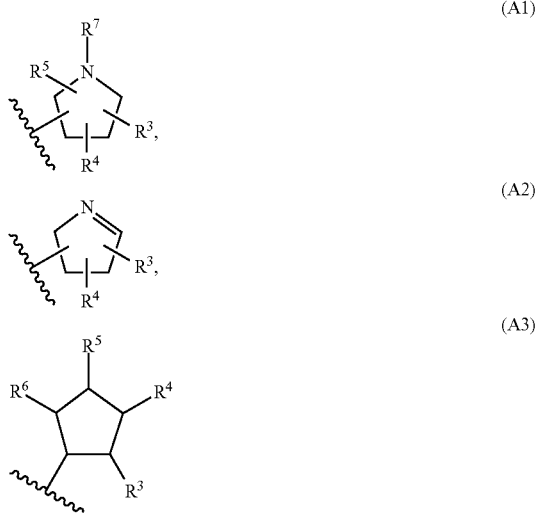

$R^1$ and $R^2$ may respectively be the same or different and represent a $C_1$-$C_6$ alkyl group, hydroxymethyl group, $C_1$-$C_6$ alkoxymethyl group or $C_1$-$C_6$ haloalkyl group, $R^3$, $R^4$, $R^5$ and $R^6$ may respectively be the same or different and represent a $C_1$-$C_6$ alkyl group, $C_1$-$C_6$ alkoxy group, $C_1$-$C_6$ hydroxyalkyl group, $C_1$-$C_6$ haloalkyl group, amino group (wherein said amino group may be substituted with 1 or 2 $C_1$-$C_6$ alkyl groups or $C_1$-$C_6$ hydroxyalkyl groups), hydroxyl group, hydrogen atom or halogen atom, $R^7$ represents a $C_1$-$C_6$ alkyl group, $C_1$-$C_6$ alkoxy group, $C_1$-$C_6$ hydroxyalkyl group, $C_1$-$C_6$ haloalkyl group, hydroxyl group or hydrogen atom, and n represents an integer of 1 or 2], or a pharmacologically acceptable salt or ester thereof, and at least one type of drug selected from an insulin sensitizer, an insulin secretagogue, a biguanide drug, and an insulin preparation.

(3) The pharmaceutical composition of (1) or (2), wherein $R^1$ is a $C_1$-$C_3$ alkyl group, hydroxymethyl group, $C_1$-$C_3$ alkoxymethyl group or $C_1$-$C_3$ haloalkyl group.

(4) The pharmaceutical composition of (1) to (3), wherein $R^1$ is a methyl group or hydroxymethyl group.

(5) The pharmaceutical composition of (1) to (4), wherein $R^2$ is a hydroxymethyl group or $C_1$-$C_3$ haloalkyl group.

(6) The pharmaceutical composition of (1) to (5), wherein $R^2$ is a hydroxymethyl group.

(7) The pharmaceutical composition of (1) to (6), wherein A is represented by the following general formula (A1).

[Chemical formula 5]

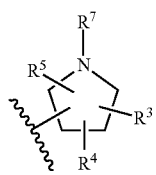

(A1)

(8) The pharmaceutical composition of (7), wherein $R^3$, $R^4$ and $R^5$ may respectively be the same or different and represent a hydroxymethyl group, hydroxyl group or hydrogen atom.

(9) The pharmaceutical composition of (7) or (8), wherein $R^7$ represents a hydrogen atom.

(10) The pharmaceutical composition of (1), comprising the combination of an α-amylase inhibitor and an insulin sensitizer.

(11) The pharmaceutical composition of (1), comprising the combination of an α-amylase inhibitor and an insulin sensitizer, and by which weight gain is suppressed.

(12) The pharmaceutical composition of (1), comprising the combination of an α-amylase inhibitor and an insulin sensitizer, and by which cardiac hypertrophy is suppressed.

(13) The pharmaceutical composition of (10) to (12), wherein the insulin sensitizer is a PPARγ agonist.

(14) The pharmaceutical composition of (10) to (12), wherein the insulin sensitizer is pioglitazone or rosiglitazone.

(15) The pharmaceutical composition of (10) to (12), wherein the insulin sensitizer is pioglitazone.

(16) The pharmaceutical composition of (1), comprising the combination of an α-amylase inhibitor and an insulin secretagogue.

(17) The pharmaceutical composition of (16), wherein the insulin secretagogue is a sulfonyl urea drug or a fast-acting insulin secretagogue.

(18) The pharmaceutical composition of (16), wherein the insulin secretagogue is glibenclamide, glimepiride or nateglinide.

(19) The pharmaceutical composition of (16), wherein the insulin secretagogue is nateglinide.

(20) The pharmaceutical composition of (1), comprising the combination of an α-amylase inhibitor and a biguanide drug.

(21) The pharmaceutical composition of (1), comprising the combination of an α-amylase inhibitor and a biguanide drug, which suppresses increases in lactic acid levels.

(22) The pharmaceutical composition of (20) or (21), wherein the biguanide drug is metformin, phenformin or buformin.

(23) The pharmaceutical composition of (20) or (21), wherein the biguanide drug is metformin.

(24) The pharmaceutical composition of (1), comprising the combination of an α-amylase inhibitor and a DPP-IV inhibitor.

(25) The pharmaceutical composition of (24), wherein the DPP-IV inhibitor is MK-0431, LAF-237 or BMS-477118.

(26) The pharmaceutical composition of (24), wherein the DPP-IV inhibitor is MK-0431.

(27) The pharmaceutical composition of (1) to (26) which is suitable for oral administration.

(28) The pharmaceutical composition of (1), comprising the combination of an α-amylase inhibitor and an insulin preparation.

(29) The pharmaceutical composition of (28), wherein the insulin preparation is fast-acting insulin.

(30) The pharmaceutical composition of (1) to (29), wherein the α-amylase inhibitor is (2R,3R,4R)-4-hydroxy-2-hydroxymethylpyrrolidin-3-yl 4-O-(6-deoxy-α-D-glucopyranosyl)-α-D-glucopyranoside, (2R,3R,4R)-4-hydroxy-2-hydroxymethyl-pyrrolidin-3-yl 4-O-(6-deoxy-β-D-glucopyranosyl)-α-D-glucopyranoside, (2R,3R,4R)-4-hydroxy-2-hydroxymethylpyrrolidin-3-yl 4-O-β-D-glucopyranosyl-α-D-glucopyranoside, (2R,3R,4R)-4-hydroxy-2-hydroxymethyl-pyrrolidin-3-yl 4-O-(6-fluoro-6-deoxy-β-D-glucopyranosyl)-D-glucopyranoside or a pharmacologically acceptable salt or ester thereof.

(31) The pharmaceutical composition of (1) to (29), wherein the α-amylase inhibitor is (2R,3R,4R)-4-hydroxy-2-hydroxymethylpyrrolidin-3-yl 4-O-(6-deoxy-α-D-glucopyranosyl)-α-D-glucopyranoside, (2R,3R,4R)-4-hydroxy-2-(hydroxymethyl)-pyrrolidin-3-yl 4-O-(6-deoxy-β-D-glucopyranosyl)-α-D-glucopyranoside, or a pharmacologically acceptable salt or ester thereof.

(32) The pharmaceutical composition of (1) to (29), wherein the α-amylase inhibitor is (2R,3R,4R)-4-hydroxy-2-(hydroxymethyl)pyrrolidin-3-yl 4-O-(6-deoxy-β-D-glucopyranosyl)-α-D-glucopyranoside, or a pharmacologically acceptable salt or ester thereof.

(33) The pharmaceutical composition of (1) to (32) which is a drug for the prophylaxis or treatment of diabetes.

(34) The pharmaceutical composition of (1) to (32) which is a drug for the prophylaxis or treatment of postprandial hyperglycemia.

(35) The pharmaceutical composition of (1) to (32) for the prophylaxis or treatment of diabetes having enhanced blood glucose lowering action as compared with single-drug administration.

(36) Use of an α-amylase inhibitor and a drug selected from an insulin sensitizer, insulin secretagogue, biguanide drug, insulin preparation and DPP-IV inhibitor for producing a pharmaceutical composition comprising the combination of said α-amylase inhibitor selected from a compound represented by the following general formula (I):

[Chemical formula 6]

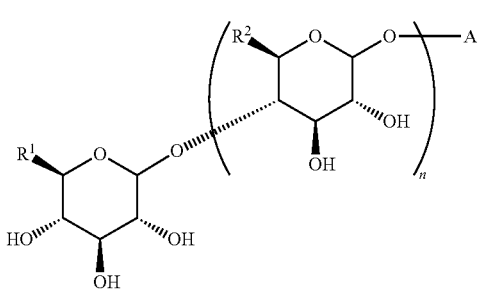

[wherein A represents the following general formula (A1), (A2) or (A3),

[Chemical formula 7]

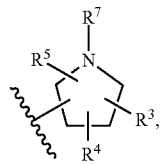
(A1)

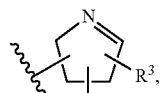
(A2)

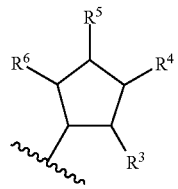
(A3)

$R^1$ and $R^2$ may respectively be the same or different and represent a $C_1$-$C_6$ alkyl group, hydroxymethyl group, $C_1$-$C_6$ alkoxymethyl group or $C_1$-$C_6$ haloalkyl group, $R^3$, $R^4$, $R^5$ and $R^6$ may respectively be the same or different and represent a $C_1$-$C_6$ alkyl group, $C_1$-$C_6$ alkoxy group, $C_1$-$C_6$ hydroxyalkyl group, $C_1$-$C_6$ haloalkyl group, amino group (wherein said amino group may be substituted with 1 or 2 $C_1$-$C_6$ alkyl groups or $C_1$-$C_6$ hydroxyalkyl groups), hydroxyl group, hydrogen atom or halogen atom, $R^7$ represents a $C_1$-$C_6$ alkyl group, $C_1$-$C_6$ alkoxy group, $C_1$-$C_6$ hydroxyalkyl group, $C_1$-$C_6$ haloalkyl group, hydroxyl group or hydrogen atom, and n represents an integer of 1 or 2], or a pharmacologically acceptable salt or ester thereof, and at least one type of drug selected from an insulin sensitizer, an insulin secretagogue, a biguanide drug, an insulin preparation and a DPP-IV inhibitor.

(37) A method for treating diabetes comprising the enhancement of therapeutic effects and reduction of adverse side effects by administering to a patient to be treated a combination of an α-amylase inhibitor selected from a compound represented by the following general formula (I):

[Chemical formula 8]

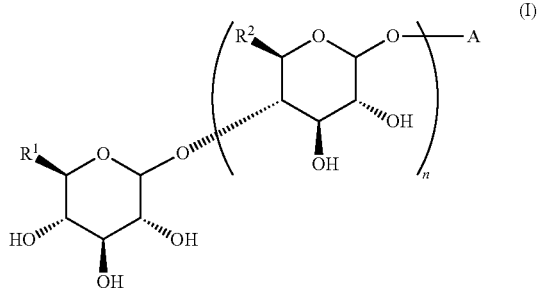

[wherein A represents the following general formula (A1), (A2) or (A3),

[Chemical formula 9]

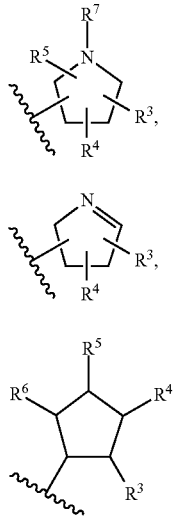

(A1)

(A2)

(A3)

R¹ and R² may respectively be the same or different and represent a $C_1$-$C_6$ alkyl group, hydroxymethyl group, $C_1$-$C_6$ alkoxymethyl group or $C_1$-$C_6$ haloalkyl group, $R^3$, $R^4$, $R^5$ and $R^6$ may respectively be the same or different and represent a $C_1$-$C_6$ alkyl group, $C_1$-$C_6$ alkoxy group, $C_1$-$C_6$ hydroxyalkyl group, $C_1$-$C_6$ haloalkyl group, amino group (wherein said amino group may be substituted with 1 or 2 $C_1$-$C_6$ alkyl groups or $C_1$-$C_6$ hydroxyalkyl groups), hydroxyl group, hydrogen atom or halogen atom, $R^7$ represents a $C_1$-$C_6$ alkyl group, $C_1$-$C_6$ alkoxy group, $C_1$-$C_6$ hydroxyalkyl group, $C_1$-$C_6$ haloalkyl group, hydroxyl group or hydrogen atom, and n represents an integer of 1 or 2], or a pharmacologically acceptable salt or ester thereof, and at least one type of drug selected from an insulin sensitizer, an insulin secretagogue, a biguanide drug, an insulin preparation and a DPP-IV inhibitor.

In the present invention, there are no particular limitations on the "α-amylase inhibitor" provided it is a drug which inhibits amylase, a digestive enzyme, an example of which is a compound represented by the following general formula (I):

[Chemical formula 10]

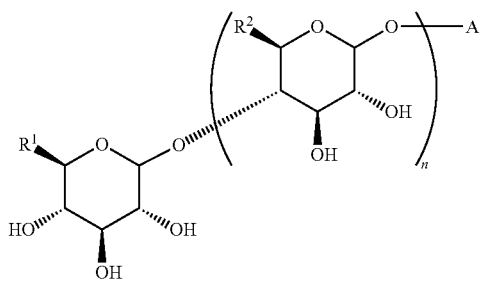

(I)

[wherein A represents the following general formula (A1), (A2) or (A3),

[Chemical formula 11]

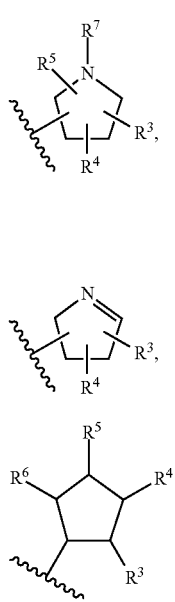

(A1)

(A2)

(A3)

R¹ and R² may respectively be the same or different and represent a $C_1$-$C_6$ alkyl group, hydroxymethyl group, $C_1$-$C_6$ alkoxymethyl group or $C_1$-$C_6$ haloalkyl group, $R^3$, $R^4$, $R^5$ and $R^6$ may respectively be the same or different and represent a $C_1$-$C_6$ alkyl group, $C_1$-$C_6$ alkoxy group, $C_1$-$C_6$ hydroxyalkyl group, $C_1$-$C_6$ haloalkyl group, amino group (wherein said amino group may be substituted with 1 or 2 $C_1$-$C_6$ alkyl groups or $C_1$-$C_6$ hydroxyalkyl groups), hydroxyl group, hydrogen atom or halogen atom, $R^7$ represents a $C_1$-$C_6$ alkyl group, $C_1$-$C_6$ alkoxy group, $C_1$-$C_6$ hydroxyalkyl group, $C_1$-$C_6$ haloalkyl group, hydroxyl group or hydrogen atom, and n represents an integer of 1 or 2], or pharmacologically acceptable salt or ester thereof. Preferably, the α-amylase inhibitor is (2R,3R,4R)-4-hydroxy-2-hydroxymethylpyrrolidin-3-yl 4-O-(6-deoxy-α-D-glucopyranosyl)-α-D-glucopyranoside, (2R,3R,4R)-4-hydroxy-2-hydroxymethyl-pyrrolidin-3-yl 4-O-(6-deoxy-β-D-glucopyranosyl)-α-D-glucopyranoside, (2R,3R,4R)-4-hydroxy-2-hydroxymethylpyrrolidin-3-yl 4-O-β-D-glucopyranosyl-α-D-glucopyranoside or (2R,3R,4R)-4-hydroxy-2-hydroxymethylpyrrolidin-3-yl 4-O-(6-fluoro-6-deoxy-β-D-glucopyranosyl)-D-glucopyranoside or pharmacologically acceptable salt or ester thereof. More preferably, the α-amylase inhibitor is (2R,3R,4R)-4-hydroxy-2-hydroxymethylpyrrolidin-3-yl 4-O-(6-deoxy-α-D-glucopyranosyl)-α-D-glucopyranoside, (2R,3R,4R)-4-hydroxy-2-hydroxymethyl-pyrrolidin-3-yl 4-O-(6-deoxy-β-D-glucopyranosyl)-α-D-glucopyranoside, or a pharmacologically acceptable salt or ester thereof.

In the present invention, an "insulin sensitizer" is the generic term for a drug which lowers blood glucose levels by improving insulin action insufficiency, examples of which include pioglitazone, rosiglitazone, MCC-555, BMS-298585, AZ-242, LY-519818, R-483 and K-111 represented by the following structural formulas:

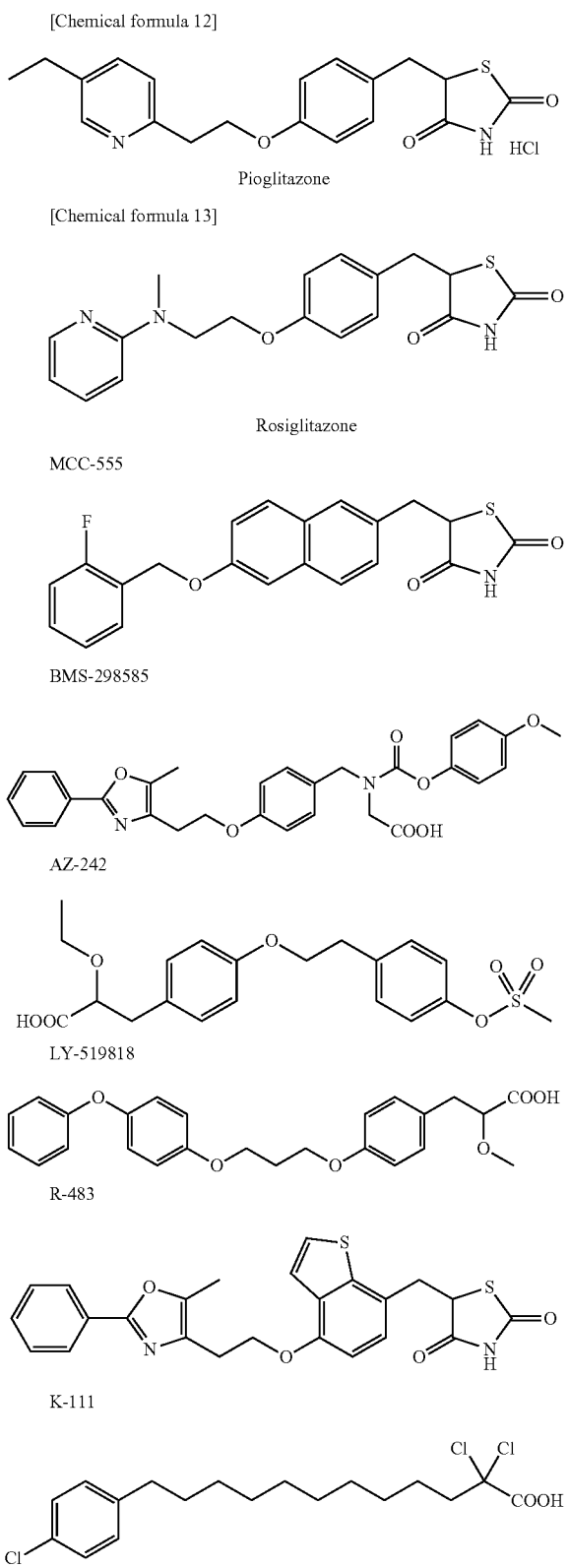

and, 3-(2,4-dichlorobenzyl)-2-methyl-N-(pentylsulfonyl)-3H-benzimidazole-5-carboxamide (FK-614), 5-[4-(6-methoxy-1-methyl-1H-benzimidazol-2-ylmethoxy)benzyl]thiazolidine-2,4-dione, and pharmacologically acceptable salts thereof The insulin sensitizer is preferably a thiazolidine-based insulin resistance ameliorant in the manner of pioglitazone, rosiglitazone, 5-[4-(6-methoxy-1-methyl-1H-benzimidazol-2-ylmethoxy)benzyl]thiazolidine-2,4-dione or a pharmacologically acceptable salt thereof, and these compounds are also known to be drugs which activate peroxisome proliferator-activated receptor (PPAR)γ.

Pioglitazone is a compound described in U.S. Pat. No. 4,687,777. Rosiglitazone is a compound described in U.S. Pat. No. 5,002,953. MCC-555 is a compound described in U.S. Pat. No. 5,594,016. BMS-298585 is a compound described in International Patent Publication WO 01/21602 pamphlet. AZ-242 is a compound described in International Patent Publication WO 99/62872 pamphlet. LY-519818 is a compound described in International Patent Publication WO 02/100813 pamphlet. 3-(2,4-Dichlorobenzyl)-2-methyl-N-(pentylsulfonyl)-3H-benzimidazole-5-carboxamide (FK-614) is a compound described in U.S. Pat. No. 6,166,219. 5-[4-(6-Methoxy-1-methyl-1H-benzimidazol-2-ylmethoxy)benzyl]thiazolidine-2,4-dione, and pharmacologically acceptable salts thereof, can be produced according to a method described in Japanese Patent Application (Kakai) No. Hei 9-295970, EP Patent No. 0745600, U.S. Pat. No. 5,886,014 and International Patent Publication WO 00/71540 pamphlet.

In the present invention, there are no particular limitations on the "biguanide drug" provided it is a drug having actions such as anaerobic glycolysis promoting action, terminal insulin action enhancement, inhibition of glucose absorption from the gastrointestinal tract, and inhibition of hepatic gluconeogenesis, and examples include 1,1-dimethylbiguanide monohydrochloride (generic name: metformin), phenformin and buformin, with metformin being preferable.

In the present invention, there are no particular limitations on the "insulin secretagogue" provided it is a drug having an action of promoting the secretion of insulin from pancreatic β cells, examples of which include sulfonyl urea (SU) agents such as glibenclamide and glimepiride, and fast-acting insulin secretagogues (phenylalanine-based blood glucose depressors) such as (−)-N-(trans-4-isopropylcyclohexanecarbonyl)-D-phenylalanine (generic name: nateglinide), with nateglinide being preferable.

In the present invention, examples of an "insulin preparation" include animal insulin preparations extracted from the pancreas of a cow or pig, and human insulin preparations synthesized by genetic engineering techniques using E. coli or yeast. Although insulin preparations include various types such as ultra-fast-acting types, fast-acting types, biphasic types, intermediate types and sustained types, these can be selected and administered according to the patient's condition, with fast-acting insulin (regular insulin) being preferable.

In the present invention, there are no particular limitations on the "dipeptidyl peptidase IV (DPP-IV) inhibitor" provided it is a drug having an action such as suppressing decomposition of GLP-1 by inhibiting DPP-IV, and examples include MK-0431 described International Patent Publication WO 2005/3135 pamphlet and International Patent Publication WO 2003/4498 pamphlet, LAF-237 described in International Patent Publication WO 2000/34241 pamphlet, and BMS-477118 described in International Patent Publication WO 2001/68603 pamphlet, which are represented by the following structural formulas, with MK-0431 being preferable.

[Chemical formula 14]

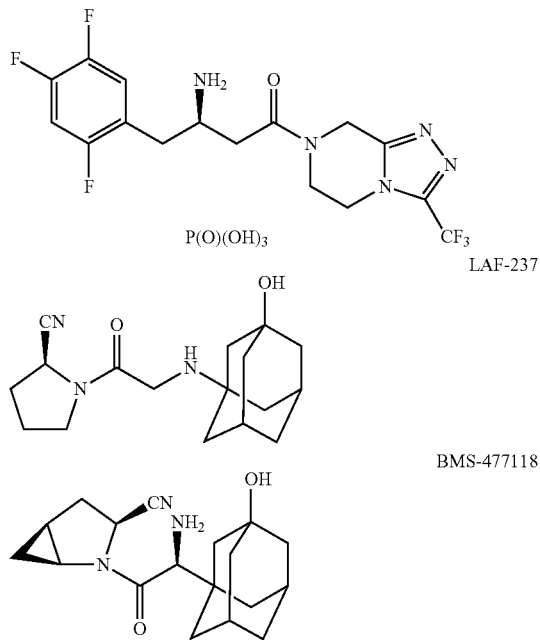

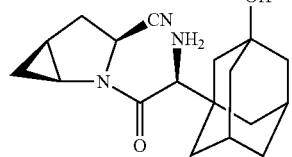

In the present invention, a "$C_1$-$C_3$ alkyl group" refers to a linear or branched alkyl group having 1 to 3 carbon atoms, examples of which include a methyl, ethyl, n-propyl and isopropyl group. A $C_1$-$C_3$ alkyl group is preferably a methyl group in $R^1$, $R^2$, $R^3$, $R^4$, $R^5$ and $R^6$.

In the present invention, a "$C_1$-$C_6$ alkyl group" refers to a linear or branched alkyl group having 1 to 6 carbon atoms, examples of which include the groups previously listed as examples of $C_1$-$C_3$ alkyl groups as well as an n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl group. A $C_1$-$C_6$ alkyl group is preferably an alkyl group having 1 to 3 carbon atoms, and most preferably a methyl group, in $R^1$, $R^2$, $R^3$, $R^4$, $R^5$, $R^6$ and $R^7$ and as a substituent of the amino group of $R^3$, $R^4$, $R^5$ and $R^6$.

In the present invention, a "halogen atom" refers to a fluorine atom, chlorine atom, bromine atom or iodine atom, and it is preferably a fluorine atom in $R^3$, $R^4$, $R^5$, $R^6$, $R^7$, $R^8$, $R^9$ and $R^{11}$.

In the present invention, a "$C_1$-$C_3$ haloalkyl group" or "$C_1$-$C_6$ haloalkyl group" refers to a group in which the above-mentioned "halogen atom" is a substituent of the above-mentioned "$C_1$-$C_3$ alkyl group" or "$C_1$-$C_6$ alkyl group", respectively. Examples of a "$C_1$-$C_3$ haloalkyl group" include a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl and 2,2-dibromoethyl group, and is preferably a fluoromethyl group in $R^1$, $R^2$, $R^3$, $R^4$, $R^5$, $R^6$ and $R^{10}$. Examples of a "$C_1$-$C_6$ haloalkyl group" include the previously listed examples of a "$C_1$-$C_3$ haloalkyl group" as well as a 4-iodobutyl, 4-fluorobutyl, 4-chlorobutyl, 5-iodopentyl, 5-fluoropentyl, 5-chloropentyl, 6-iodohexyl, 6-fluorohexyl and 6-chlorohexyl group, and it is preferably a $C_1$-$C_3$ haloalkyl group and more preferably a fluoromethyl group in $R^1$, $R^2$, $R^3$, $R^4$, $R^5$, $R^6$, $R^7$ and $R^{10}$.

In the present invention, a "$C_1$-$C_3$ hydroxyalkyl group" or "$C_1$-$C_6$ hydroxyalkyl group" refers to a group in which a hydroxyl group is a substituent of the above-mentioned "$C_1$-$C_3$ alkyl group" or "$C_1$-$C_6$ alkyl group", respectively. Examples of a "$C_1$-$C_3$ hydroxyalkyl group" include a hydroxymethyl, hydroxyethyl and hydroxypropyl group, and it is preferably a hydroxymethyl group in $R^3$, $R^4$, $R^5$, $R^6$ and $R^{10}$. Examples of a "$C_1$-$C_6$ hydroxyalkyl group" include the previously listed examples of a "$C_1$-$C_3$ hydroxyalkyl group" as well as a hydroxybutyl, hydroxypentyl and hydroxyhexyl group, and it is preferably a $C_1$-$C_3$ hydroxyalkyl group and more preferably a hydroxymethyl group in $R^3$, $R^4$, $R^5$, $R^6$, $R^7$, $R^{10}$ and $R^{11}$, and as a substituent of the amino group of $R^1$.

In the present invention, a "$C_1$-$C_3$ alkoxy group" or "$C_1$-$C_6$ alkoxy group" refers to a group in which the aforementioned "$C_1$-$C_3$ alkyl group" or "$C_1$-$C_6$ alkyl group", respectively, is bonded to an oxygen atom. Examples of a "$C_1$-$C_3$ alkoxy group" include a methoxy, ethoxy, n-propoxy and isopropoxy group. Examples of a "$C_1$-$C_6$ alkoxy group" include the previously listed examples of a "$C_1$-$C_3$ alkoxy group" as well as an n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy group, and it is preferably a $C_1$-$C_3$ alkoxy group and more preferably a methoxy group in $R^3$, $R^4$, $R^5$, $R^6$ and $R^7$.

In the present invention, a "$C_1$-$C_3$ alkoxymethyl group" or "$C_1$-$C_6$ alkoxymethyl group" refers to a group in which the aforementioned "$C_1$-$C_3$ alkoxy group" or "$C_1$-$C_6$ alkoxy group", respectively, is bonded to a methyl group. Examples of a "$C_1$-$C_3$ alkoxymethyl group" include a methoxymethyl group, ethoxymethyl group, n-propoxymethyl group and isopropoxymethyl group, and it is preferably a methoxymethyl group in $R^1$ and $R^2$. Examples of a "$C_1$-$C_6$ alkoxymethyl group" include the previously listed examples of a "$C_1$-$C_3$ alkoxymethyl group" as well as an n-butoxymethyl, isobutoxymethyl, s-butoxymethyl, tert-butoxymethyl, n-pentoxymethyl, isopentoxymethyl, 2-methylbutoxymethyl, neopentoxymethyl, n-hexyloxymethyl, 4-methylpentoxymethyl, 3-methylpentoxymethyl, 2-methylpentoxymethyl, 3,3-dimethylbutoxymethyl, 2,2-dimethylbutoxymethyl, 1,1-dimethylbutoxymethyl, 1,2-dimethylbutoxymethyl, 1,3-dimethylbutoxymethyl and 2,3-dimethylbutoxymethyl group, and it is preferably a "$C_1$-$C_3$ alkoxymethyl group" and more preferably a methoxymethyl group in $R^1$ and $R^2$.

An oligosaccharide derivative having the aforementioned general formula (I) of the present invention can be converted to an acid addition salt in the case of having a basic group in accordance with conventional methods. Examples of such salts include salts of halogenated hydroacids such as hydrofluoric acid, hydrochloric acid, hydrobromic acid and hydroiodic acid; inorganic acid salts such as nitrates, perchlorates, sulfates and phosphates; salts of lower alkanesulfonic acids such as methanesulfonic acid, trifluoromethanesulfonic acid and ethanesulfonic acid; salts of arylsulfonic acids such as benzenesulfonic acid and p-toluenesulfonic acid; salts of amino acids such as glutamic acid and aspartic acid; and salts of carboxylic acids such as acetic acid, fumaric acid, tartaric acid, oxalic acid, maleic acid, malic acid, succinic acid, benzoic acid, mandelic acid, ascorbic acid, lactic acid, gluconic acid and citric acid. This acid addition salt is preferably a salt of a halogenated hydroacid, and most preferably a hydrochloride.

Moreover, since the oligosaccharide derivative having general formula (I) of the present invention has a hydroxyl group, it can be converted to a metal salt in accordance with conventional methods. Examples of such salts include salts of alkaline metals such as lithium, sodium and potassium; salts of alkaline earth metals such as calcium, barium and magnesium; and aluminum salts. A preferable salt is an alkaline metal salt.

The oligosaccharide derivative having general formula (I) of the present invention can be converted to a pharmacologically acceptable ester in accordance with conventional methods. There are no particular limitations on such esters provided they are used in medical applications and are pharmacologically acceptable as compared with the oligosaccharide having general formula (I).

Examples of an ester of the oligosaccharide derivative having general formula (I) of the present invention include a $C_1$-$C_6$ alkyl group (wherein said alkyl group may be substituted with a trialkylsilyl group), $C_7$-$C_{16}$ aralkyl group, $C_1$-$C_5$ alkyl group substituted with $C_1$-$C_6$ alkanoyloxy, $C_1$-$C_5$ alkyl group substituted with $C_1$-$C_6$ alkyloxycarbonyloxy, $C_1$-$C_5$ alkyl group substituted with $C_5$-$C_7$ cycloalkyloxycarbonyloxy, $C_1$-$C_5$ alkyl group substituted with $C_6$-$C_{10}$ aryloxycarbonyloxy, and 2-oxo-1,3-dioxolen-4-yl group having $C_1$-$C_6$ alkyl as a substituent at the 5-position.

Here, a $C_1$-$C_6$ alkyl group is preferably a linear or branched alkyl group having 1 to 4 carbon atoms, more preferably a methyl, ethyl, propyl, isopropyl, butyl or isobutyl group, and most preferably a methyl group or ethyl group.

A $C_1$-$C_5$ alkyl group is a linear or branched alkyl group having 1 to 5 carbon atoms, preferably a methyl, ethyl, propyl, isopropyl, butyl or isobutyl group, and most preferably a methyl group or ethyl group.

A $C_5$-$C_7$ cycloalkyl group is a 5- to 7-membered saturated cyclic hydrocarbon group, examples of which include a cyclopentyl, cyclohexyl and cycloheptyl group, and it is preferably a cyclohexyl group.

A $C_6$-$C_{10}$ aryl group is an aromatic hydrocarbon group having 6 to 10 carbon atoms, examples of which include a phenyl, indenyl and naphthyl group, and it is preferably a phenyl group.

A $C_7$-$C_{16}$ aralkyl group is a group in which the aforementioned "$C_6$-$C_{10}$ aryl group" is bonded to the aforementioned "$C_1$-$C_6$ alkyl group", examples of which include a benzyl, α-naphthylmethyl, β-naphthylmethyl, indenylmethyl group, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-napthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-napthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl group. The $C_7$-$C_{16}$ aralkyl group is preferably an "aralkyl group" in which the "alkyl group" has 1 to 4 carbon atoms, and more preferably a benzyl group.

Specific examples of preferable ester residues include a methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy)ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy) ethyl, propoxycarbonyloxymethyl, 1-(propoxycarbonyloxy)ethyl, isopropoxycarbonyloxymethyl, 1-(isopropoxycarbonyloxy) ethyl, butoxycarbonyloxymethyl, 1-(butoxycarbonyloxy) ethyl, isobutoxycarbonyloxymethyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopentanecarbonyloxy)ethyl group, cyclohexanecarbonyloxymethyl, 1-(cyclohexanecarbonyloxy)ethyl, cyclopentyloxycarbonyloxymethyl, 1-(cyclopentyloxycarbonyloxy)ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl, (5-methyl-2-oxo-1,3-dioxolen-4-yl)methyl and 2-trimethylsilylethyl group.

Furthermore, an oligosaccharide derivative having the general formula (I) has various isomers. For example, in an oligosaccharide having the general formula (I), optical isomers can exist for group A and the sugar bonding moiety. In the general formula (I), stereoisomers based on these asymmetric carbon atoms as well as equivolume and non-equivolume mixtures of these isomers are all represented by a single formula. Thus, the present invention includes all of these isomers and all mixtures of these isomers in various ratios.

Moreover, the present invention includes all of the oligosaccharide derivatives having the general formula (I), salts and esters thereof in the case where solvates (such as hydrates) are formed therefrom.

Moreover, all compounds converted to an oligosaccharide derivative having the general formula (I), or a salt or ester thereof, as a result of being metabolized in a living body (for example, amide derivatives in the manner of so-called prodrugs) are included in the present invention.

In the present invention, (A1) is preferably represented by the following general formula (A1a) or (A1b):

[Chemical formula 15]

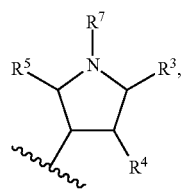

(A1a)

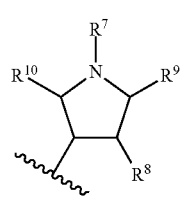

(A1b)

and is more preferably represented by the following general formula (A1c):

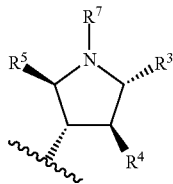

(A1c)

(A2) is preferably represented by the following general formula (A2a) or (A2b):

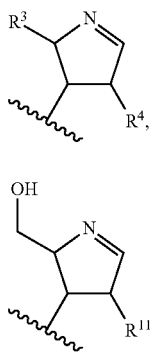

(A2a)

(A2b)

and is more preferably represented by the following general formula (A2c):

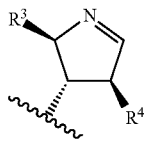

(A2c)

(A3) is preferably represented by the following general formula (A3a):

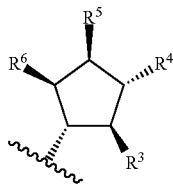

(A3a)

$R^1$ is preferably a $C_1$-$C_6$ alkyl group or hydroxymethyl group, more preferably a methyl group or hydroxymethyl group, and particularly preferably a methyl group.

$R^2$ is preferably a $C_1$-$C_6$ alkyl group or hydroxymethyl group, more preferably a methyl group or hydroxymethyl group, and particularly preferably a hydroxymethyl group.

$R^3$, in the general formulas (A1), (A1c) and (A1a), is preferably a $C_1$-$C_6$ hydroxyalkyl group, hydroxyl group, halogen atom or hydrogen atom, more preferably a $C_1$-$C_3$ hydroxyalkyl group or hydrogen atom, and particularly preferably a hydrogen atom. In general formulas (A2), (A2a), (A2b) and (A2c), it is preferably a $C_1$-$C_6$ hydroxyalkyl group, hydroxyl group, hydrogen atom or halogen atom, more preferably a $C_1$-$C_3$ hydroxyalkyl group or hydrogen atom, and particularly preferably a hydroxymethyl group. In general formulas (A3) and (A3a), it is preferably a $C_1$-$C_6$ hydroxyalkyl group, amino group, hydroxyl group, hydrogen atom or halogen atom, more preferably a hydroxymethyl group, hydroxyl group or amino group, and particularly preferably a hydroxyl group.

$R^4$, in the general formulas (A1), (A1c) and (A1a), is preferably a $C_1$-$C_6$ hydroxyalkyl group, hydrogen atom, hydroxyl group or halogen atom, more preferably a hydroxyl group or halogen atom, particularly preferably a hydroxyl group or fluorine atom, and most preferably a hydroxyl group. In general formulas (A2), (A2a), (A2b) and (A2c), it is preferably a $C_1$-$C_6$ hydroxyalkyl group, hydrogen atom, halogen atom or hydroxyl group, and more preferably a hydroxyl group. In general formulas (A3) and (A3a), it is preferably a $C_1$-$C_6$ hydroxyalkyl group, amino group, hydroxyl group, halogen atom or hydrogen atom, more preferably a hydroxyl group, halogen atom or hydrogen atom, and particularly preferably a hydroxyl group.

$R^5$, in the general formulas (A1), (A1c) and (A1a), is preferably a hydroxyl group, halogen atom, $C_1$-$C_6$ hydroxyalkyl group, $C_1$-$C_6$ haloalkyl group or hydrogen atom, more preferably a $C_1$-$C_6$ hydroxyalkyl group, particularly preferably a $C_1$-$C_3$ hydroxyalkyl group, and most preferably a hydroxymethyl group. In the general formulas (A3) and (A3a), it is preferably a $C_1$-$C_6$ hydroxyalkyl group, hydroxyl group, hydrogen atom, halogen atom or amino group (wherein said amino group may be substituted with 1 or 2 $C_1$-$C_6$ alkyl or $C_1$-$C_6$ hydroxyalkyl groups), more preferably an amino group (wherein said amino group may be substituted with 1 or 2 $C_1$-$C_6$ alkyl groups or $C_1$-$C_6$ hydroxyalkyl groups), and particularly preferably an amino group.

$R^6$, in general formulas (A3) and (A3a), is preferably a $C_1$-$C_6$ hydroxyalkyl group, amino group, hydroxyl group, hydrogen atom or halogen atom, more preferably a $C_1$-$C_6$ hydroxyalkyl group, particularly preferably a $C_1$-$C_3$ hydroxyalkyl group, and most preferably a hydroxymethyl group.

$R^7$ is preferably a hydrogen atom, $C_1$-$C_6$ hydroxyalkyl group or $C_1$-$C_6$ alkyl group, more preferably a hydrogen atom or methyl group, and particularly preferably a hydrogen atom.

$R^8$ and $R^9$ are preferably a $C_1$-$C_3$ hydroxyalkyl group, halogen atom, hydrogen atom or hydroxyl group, and more preferably a hydrogen atom or hydroxyl group.

$R^{10}$ is preferably a $C_1$-$C_6$ hydroxyalkyl group, more preferably a $C_1$-$C_3$ hydroxyalkyl group, and particularly preferably a hydroxymethyl group.

$R^{11}$ is preferably a hydroxyl group.

n is preferably 1.

The general formula (I) is preferably represented by the following general formula (IA) or (IB):

[Chemical formula 20]

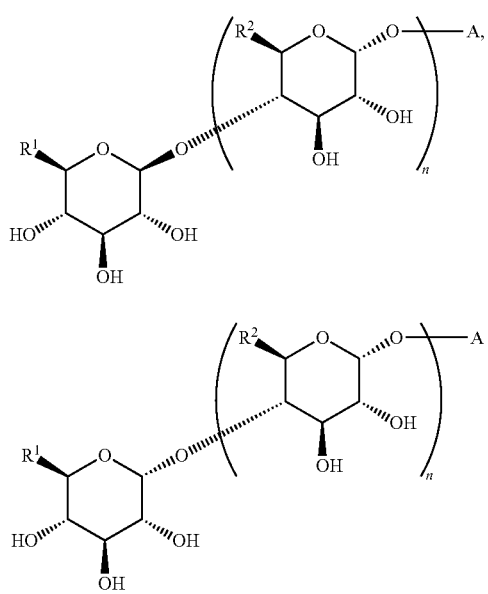

A is preferably represented by the following general formula (A1) or (A2):

[Chemical formula 21]

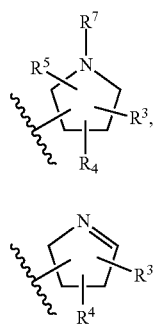

and preferably (A1).

A compound having the aforementioned general formula (I) of the present invention can be produced using a known compound as a starting raw material according to, for example, the method indicated below.

In the aforementioned formulas and following descriptions, A, $R^1$, $R^2$, $R^3$, $R^4$, $R^5$, $R^6$, $R^7$, $R^8$, $R^9$, $R^{10}$, $R^{11}$ and n are the same as previously defined. However, in the case $R^1$, $R^2$, $R^3$, $R^4$, $R^5$, $R^6$, $R^7$, $R^8$, $R^9$, $R^{10}$ or $R^{11}$ represent a hydroxyl group or group having a hydroxyl group, said hydroxyl group may be protected.

Step A:

[Chemical formula 22]

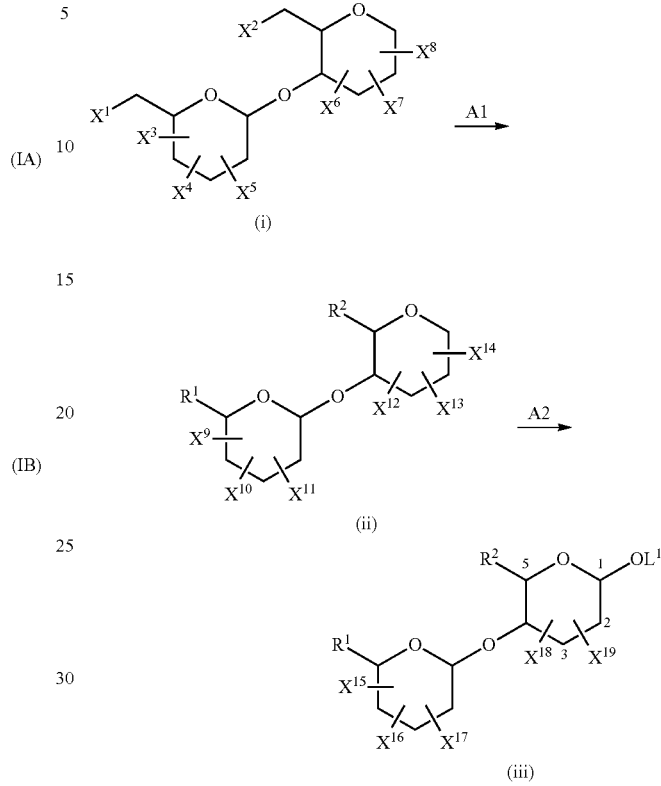

Step B:
Method Ba:

[Chemical formula 23]

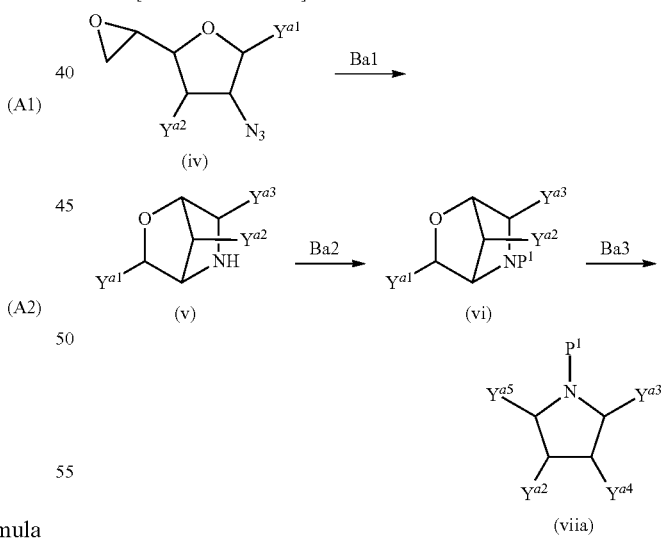

Method Bb:

[Chemical formula 24]

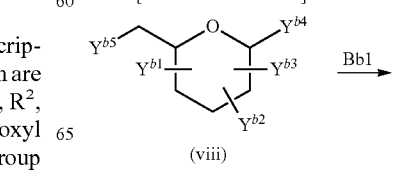

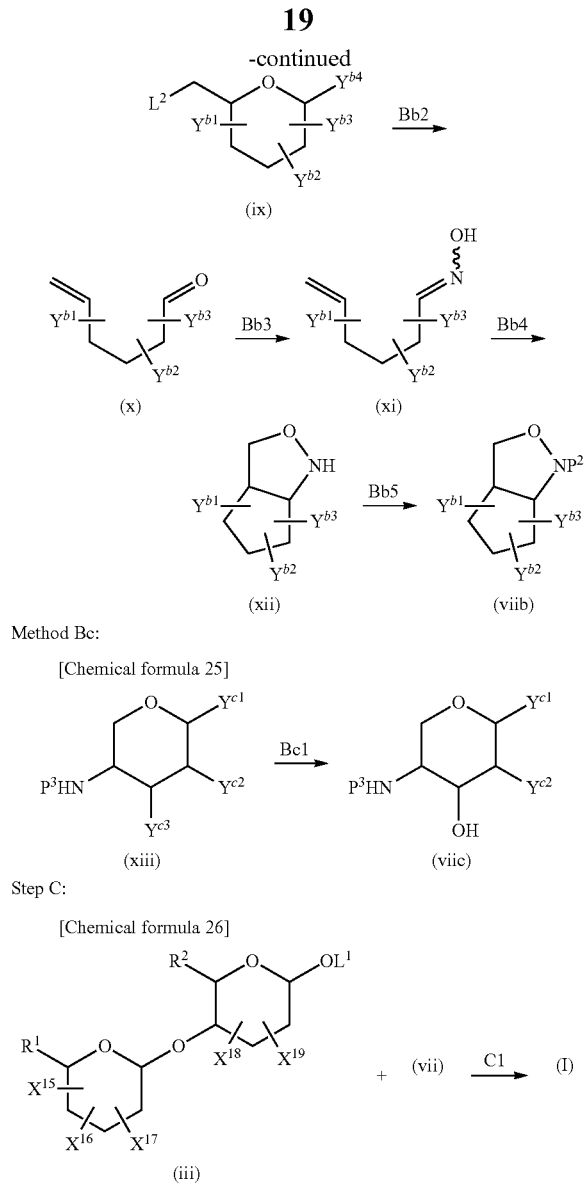

Method Bc:

[Chemical formula 25]

Step C:

[Chemical formula 26]

In the aforementioned steps and following descriptions, $X^1$-$X^{19}$, $Y^{a1}$-$Y^{a5}$ and $Y^{c1}$-$Y^{c3}$ may be the same or different and each represents a hydrogen atom or hydroxyl group (said hydroxyl group may optionally be protected by a protecting group), $Y^{b1}$-$Y^{b5}$ may be the same or different, and each represents a halogen atom, hydrogen atom or hydroxyl group (said hydroxyl group may optionally be protected by a protecting group), $P^1$ represents $R^6$ or a protecting group of an amino group such as a $C_1$-$C_6$ alkoxycarbonyl group (preferably a t-butoxycarbonyl group) or $C_7$-$C_{16}$ aralkyloxycarbonyl group (preferably a benzyloxycarbonyl group), $P^2$ and $P^3$ are the same or different and each represents $R^7$ or a protecting group of an amino group, such as $C_1$-$C_6$ alkoxycarbonyl group (and preferably a t-butoxycarbonyl group) or $C_7$-$C_{16}$ aralkyloxycarbonyl group (and preferably a benzyloxycarbonyl group), and $L^1$ and $L^2$ represent a hydroxyl group (wherein said hydroxyl group may be protected by a protecting group or a hydrogen atom may be substituted with a leaving group) or a leaving group.

There are no particular limitations on the protecting group used for protecting a hydroxyl group provided it is typically used to protect a hydroxyl group, examples of which include "aliphatic acyl groups" such as alkylcarbonyl groups, e.g. a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl group, icosanoyl or henaicosanoyl group, carboxylated alkylcarbonyl groups, e.g. a succinoyl, glutaroyl or adipoyl group, halogeno lower alkylcarbonyl groups, e.g. a chloroacetyl, dichloroacetyl, trichloroacetyl or trifluoroacetyl group, lower alkoxy lower alkylcarbonyl groups, e.g. methoxyacetyl, and unsaturated alkylcarbonyl groups, e.g. (E)-2-methyl-2-butenoyl; "aromatic acyl groups" including arylcarbonyl groups such as a benzoyl, α-naphthoyl or β-naphthoyl group, halogenoarylcarbonyl groups such as 2-bromobenzoyl or 4-chlorobenzoyl, lower alkylated arylcarbonyl groups such as 2,4,6-trimethylbenzoyl or 4-toluoyl, lower alkoxylated arylcarbonyl groups such as 4-anisoyl, carboxylated arylcarbonyl groups such as 2-carboxybenzoyl, 3-carboxybenzoyl or 4-carboxybenzoyl, nitrated arylcarbonyl groups such as 4-nitrobenzoyl or 2-nitrobenzoyl, lower alkoxycarbonylated arylcarbonyl groups such as 2-(methoxycarbonyl)benzoyl, and arylated arylcarbonyl groups such as 4-phenylbenzoyl; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl; "tetrahydrofuranyl or tetrahydrothiofuranyl groups" such as tetrahydrofuran-2-yl or tetrahydrothiofuran-2-yl; "silyl groups" including tri-lower alkylsilyl groups such as trimethylsilyl, triethylsilyl, isopropyldimethylsilyl, t-butyldimethylsilyl, methyldiisopropylsilyl, methyldi-t-butylsilyl or triisopropylsilyl, and tri-lower alkylsilyl groups substituted with 1 or 2 aryl groups such as diphenylmethylsilyl, diphenylbutylsilyl, diphenylisopropylsilyl or phenyldiisopropylsilyl; "alkoxymethyl groups" including lower alkoxymethyl groups such as methoxymethyl, 1,1-dimethyl-1-methoxymethyl, ethoxymethyl, propoxymethyl, isopropoxymethyl, butoxymethyl or t-butoxymethyl, lower alkoxylated lower alkoxymethyl groups such as 2-methoxyethoxymethyl, and halogeno lower alkoxymethyl groups such as 2,2,2-trichloroethoxymethyl or bis(2-chloroethoxy)methyl; "substituted ethyl groups" including lower alkoxylated ethyl groups such as 1-ethoxyethyl or 1-(isopropoxy)ethyl, and halogenated ethyl groups such as 2,2,2-trichloroethyl; "aralkyl groups" including lower alkyl groups substituted with 1 to 3 aryl groups such as benzyl, α-naphthylmethyl, β-naphthylmethyl, diphenylmethyl, triphenylmethyl, α-naphthyldiphenylmethyl or 9-anthrylmethyl, and lower alkyl groups substituted with 1 to 3 aryl groups in which an aryl ring is substituted with lower alkyl, lower alkoxy, halogen or cyano group such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, or piperonyl; "alkoxycarbonyl groups" including lower alkoxycarbonyl groups such as methoxycarbonyl, ethoxycarbonyl, t-butoxycarbonyl or isopropoxycarbonyl, and lower alkoxycarbonyl groups substituted with a halogen atom or tri-lower alkylsilyl group such as 2,2,2-trichloroethoxycarbonyl or 2-trimethylsilylethoxycarbonyl; "alkenyloxycarbonyl groups" such as vinyloxycarbonyl or allyloxycarbonyl; and, "aralkyloxycarbonyl groups" in which the aryl ring may be substituted with 1 or 2 lower alkoxy or nitro groups such as a benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl group. In addition, there are no particular limitations on the reagent used to protect a diol provided it is normally used for protecting diols, and preferable examples include aldehyde derivatives such as benzaldehyde, ketone derivatives such as acetone, and dimethoxy compounds such as 2,2-dimethoxypropane or dimethoxybenzyl.

The process for producing a compound (I) of the present invention is composed of the following three steps.
(1) Step A is to produce an intermediate (iii) which is the left side portion of compound (I).
(2) Step B is to produce an intermediate (vii) which is the right side portion of compound (I), and method a, method b or method c can be selected for this step corresponding to the desired compound (I).
(3) Step C is to produce compound (I) of the present invention by condensing the intermediate (iii) obtained in Step A and the intermediate (vii) obtained in Step B.

The following provides an explanation of each step.
(Step A)
Raw material compound (i) is produced by protecting and de-protecting a hydroxyl group of a known compound according to a known method. In addition, the hydroxyl group can be protected and de-protected as necessary in this step.

Protection and de-protection of the hydroxyl group is carried out according to commonly known methods, and can be carried out in compliance with, for example, Green & Watts eds., "Protective Groups in Organic Synthesis, Third Edition" (Wiley-Interscience, USA).

In addition, de-protection can also be carried out, for example, by a method like that described below.

In the case of using a silyl group as the protecting group of the hydroxyl group, it can normally be removed by treating with a compound that forms a fluorine anion such as tetrabutyl ammonium fluoride, hydrofluoric acid, hydrofluoric acid-pyridine or potassium fluoride, or by treating with an organic acid such as acetic acid, methanesulfonic acid, para-toluenesulfonic acid, trifluoroacetic acid or trifluoromethanesulfonic acid, or an inorganic acid such as hydrochloric acid.

Furthermore, in the case of removing with a fluorine anion, the reaction can be promoted by adding an organic acid such as formic acid, acetic acid or propionic acid.

There are no particular limitations on the solvent used provided it does not inhibit the reaction and dissolves the starting substance to a certain degree, preferable examples of which include ethers such as diethyl ether, diisopropyl ether, tetrahydrofuran, dioxane, dimethoxyethane or diethylene glycol dimethyl ether; nitriles such as acetonitrile or isobutyronitrile; water; organic acids such as acetic acid; and mixed solvents thereof.

There are no particular limitations on the reaction temperature and reaction time, and the reaction is normally carried out at 0 to 100° C. (and preferably 10 to 30° C.) for 1 to 24 hours.

In the case the protecting group of the hydroxyl group is an aralkyl group or aralkyloxycarbonyl group, it is normally preferably removed by contacting with a reducing agent in a solvent (and preferably by catalytic reduction at normal temperature in the presence of a catalyst), or by using an oxidizing agent.

There are no particular limitations on the solvent used when removing by catalytic reduction provided it is not involved in the reaction, preferable examples of which include alcohols such as methanol, ethanol or isopropanol, ethers such as diethyl ether, tetrahydrofuran or dioxane, aromatic hydrocarbons such as toluene, benzene or xylene, aliphatic hydrocarbons such as hexane or cyclohexane, esters such as ethyl acetate or propyl acetate, amides such as formamide, dimethylformamide, dimethylacetamide, N-methyl-2-pyrrolidone or hexamethylphosphotriamide, fatty acids such as formic acid or acetic acid, water and mixed solvents thereof, and more preferable examples including alcohols, fatty acids, mixed solvents of alcohols and ethers, mixed solvents of alcohols and water, and mixed solvents of fatty acids and water.

There are no particular limitations on the catalyst used provided it is normally used in catalytic reduction reactions, preferable examples of which include palladium carbon, palladium black, Rainey nickel, platinum oxide, platinum black, rhodium-aluminum oxide, triphenylphosphine-rhodium chloride and palladium-barium sulfate.

There are no particular limitations on the pressure, and the reaction is normally carried out at a pressure of 1 to 10 atmospheres.

Although varying depending on the types of starting substance, solvent, catalyst and so forth, the reaction temperature and reaction time are normally 0 to 100° C. (and preferably 20 to 70° C.) for 5 minutes to 48 hours (and preferably 1 to 24 hours).

There are no particular limitations on the solvent used to remove the protecting group by oxidation provided it is not involved in the reaction, and is preferably a water-containing organic solvent.

Preferable examples of such organic solvents include ketones such as acetone, halogenated hydrocarbons such as methylene chloride, chloroform or carbon tetrachloride, nitrites such as acetonitrile, ethers such as diethyl ether, tetrahydrofuran and dioxane, amides such as dimethylformamide, dimethylacetamide or hexamethylphosphorotriamide, and sulfoxides such as dimethyl sulfoxide.

There are no particular limitations on the oxidizing agent used provided it is a compound used for oxidation, preferable examples of which include potassium persulfate, sodium persulfate, cerium ammonium nitrate (CAN) and 2,3-dichloro-5,6-dicyano-p-benzoquinone (DDQ).

Although varying according to the types of starting substance, solvent, catalyst and so forth, the reaction temperature and reaction time are normally 0 to 150° C. for 10 minutes to 24 hours.

In addition, the protecting group can also be removed by allowing an alkaline metal such as lithium metal or sodium metal to act at −78 to −20° C. in liquid ammonia or an alcohol such as methanol or ethanol.

Moreover, the protecting group can also be removed by using aluminum chloride-sodium iodide or an alkylsilyl halide such as trimethylsilyliodide in a solvent.

There are no particular limitations on the solvent used provided it is not involved in the reaction, preferable examples of which include nitrites such as acetonitrile, halogenated hydrocarbons such as methylene chloride or chloroform, and mixed solvents thereof.

Although varying depending on the starting substance, solvent and so forth, the reaction temperature and reaction time are normally 0 to 50° C. for 5 minutes to 3 days.

Furthermore, in the case the reaction substrate has a sulfur atom, aluminum chloride-sodium iodide is used preferably.

In the case the protecting group of the hydroxyl group is an aliphatic acyl group, aromatic acyl group or alkoxycarbonyl group, the protecting group can be removed by treating with a base in a solvent.

There are no particular limitations on the base used provided it does not have an effect on other portions of the compound, preferable examples of which include metal alkoxides such as sodium methoxide; alkaline metal carbonates such as sodium carbonate, potassium carbonate or lithium carbonate; alkaline metal hydroxides such as sodium hydroxide, potassium hydroxide, lithium hydroxide or barium hydroxide; and, ammonias such as aqueous ammonia or concentrated ammonia-methanol.

There are no particular limitations on the solvent used provided it is normally used in hydrolysis reactions, preferable examples of which include water; organic solvents including alcohols such as methanol, ethanol or n-propanol, and ethers such as tetrahydrofuran or dioxane; and, mixed solvents of water and the aforementioned organic solvents.

Although varying depending on the starting substance, solvent, base used and so forth, there are no particular limitations on the reaction temperature and reaction time, and the reaction is normally carried out at 0 to 150° C. for 1 to 10 hours to suppress side reactions.

In the case the protecting group of the hydroxyl group is an alkoxymethyl group, tetrahydropyranyl group, tetrahydrothiopyranyl group, tetrahydrofuranyl group, tetrahydrothiofuranyl group or substituted ethyl group, the protecting group is normally removed by treating with an acid in a solvent.

There are no particular limitations on the acid used provided it is normally used as a Bronsted acid or Lewis acid, preferable examples of which include Bronsted acids including hydrogen chloride; inorganic acids such as hydrochloric acid, sulfuric acid or nitric acid; and, organic acids such as acetic acid, trifluoroacetic acid, methanesulfonic acid or p-toluenesulfonic acid; and, Lewis acids such as boron trifluoride. However, strongly acidic cation exchange resins such as Dowex 50W can also be used.

There are no particular limitations on the solvent used provided it does not inhibit the reaction and dissolves the starting substance to a certain degree, preferable examples of which include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, disopropyl ether, tetrahydrofuran, dioxane, dimethoxyethane or diethylene glycol dimethyl ether; alcohols such as methanol, ethanol, n-propanol, isopropanol, n-butanol, isobutanol, tert-butanol, isoamyl alcohol, diethylene glycol, glycerin, octanol, cyclohexanol or methyl cellusorb; ketones such as acetone, methyl ethyl ketone, methyl isobutyl ketone, isophorone or cyclohexanone; water, and mixed solvents thereof, while preferable examples include halogenated hydrocarbons, esters and ethers.

Although varying depending on the types and concentrations of the starting substance, solvent and acid used, the reaction temperature and reaction time is normally −10 to 100° C. (and preferably −5 to 50° C.) for 5 minutes to 48 hours (and preferably 30 minutes to 10 hours).

In the case the protecting group of the hydroxyl group is an alkenyloxycarbonyl group, removal of the protecting group is normally achieved by treating with a base under similar conditions as the removal reaction in the case the protecting group of the hydroxyl group is the aforementioned aliphatic acyl group, aromatic acyl group or alkoxycarbonyl group.

Furthermore, in the case the protecting group of the hydroxyl group is allyloxycarbonyl, a method whereby the protecting group is removed by using palladium and triphenylphosphine or bis(methyldiphenylphosphine) (1,5-cyclooctadiene) iridium (I)-hexafluorophosphate in particular is simple, and can be carried out with few side reactions.

In the case the protecting group of the hydroxyl group is a formyl group, it can be removed by treating with a base in a solvent.

There are no particular limitations on the base used provided it does not have an effect on other portions of the compound, and an alkaline metal hydrogen carbonate such as potassium hydrogencarbonate are used preferably.

There are no particular limitations on the solvent used provided it is normally used in hydrolysis reactions, and water, an organic solvent including alcohols such as methanol, ethanol or n-propanol, and ethers such as tetrahydrofuran or dioxane, or a mixed solvent of water and the organic solvent, is used preferably.

Although varying depending on the starting substance, solvent, base used and so forth, there are no particular limitations on the reaction temperature and reaction time, and the reaction is normally carried out at 0 to 150° C. for 1 to 10 hours to suppress side reactions.

In the case the protecting group of the hydroxyl group is a halogen-substituted acetamide group such as a trifluoroacetamide group, it is removed by treating with a base in a solvent.

There are no particular limitations on the base used provided it does not have an effect on other portions of the compound, and a basic resin such as Dowex 1×4(OH⁻) is used preferably.

There are no particular limitations on the solvent used provided it is normally used in hydrolysis reactions, and water or an alcohol such as methanol, ethanol or n-propanol is used preferably, while water are more preferable.

A palladium catalyst such as palladium chloride or an iridium catalyst is preferable for de-protecting an allyl group at an anomeric position.

There are no particular limitations on the solvent used provided it is normally used in catalytic reactions, and alcohol solvents such as methanol, ether solvents such as tetrahydrofuran or water are preferable, while methanol or tetrahydrofuran are more preferable.

[Step A1]

This step is for producing compound (ii), and is achieved by introducing a leaving group for a hydroxyl group at a desired site as necessary, followed by carrying out a nucleophilic substitution reaction with a reagent corresponding to the introduced $R^1$ and $R^2$ groups.

In the case the leaving group is a halogen atom, there are no particular limitations on the solvent used provided it does not inhibit the reaction and dissolves the starting substance, preferable examples of which include ethers such as diethyl ether, tetrahydrofuran or dioxane; amides such as dimethylformamide, dimethylacetamide or hexamethylphosphotriamide; halogenated hydrocarbons such as dichloromethane, chloroform or 1,2-dichloroethane; nitriles such as acetonitrile or propionitrile; esters such as ethyl formate or ethyl acetate; and, mixed solvents thereof, with halogenated hydrocarbons or ethers being more preferable, and dichloromethane or tetrahydrofuran being particularly preferable.

There are no particular limitations on the halogenation agent used provided it is normally used to convert a hydroxyl group to a halogen atom, preferable examples of which include dialkylaminosulfate trihalides such as diethylaminosulfur trifluoride (DAST), thionyl halides such as thionyl chloride, thionyl bromide or thionyl iodide, sulfuryl halides such as sulfuryl chloride, sulfuryl bromide or sulfuryl iodide, phosphorus trihalides such as phosphorus trichloride, phosphorus tribromide or phosphorus triiodide, phosphorus pentahalides such as phosphorus pentachloride, phosphorus pentabromide or phosphorus pentaiodide, and phosphorus oxyhalides such as phosphorus oxychloride, phosphorus oxybromide or phosphorus oxyiodide.

The reaction temperature is 0° C. to the heating temperature (boiling point of the solvent used), and preferably room temperature to the heating temperature (boiling point of the solvent used).

The reaction time is 10 minutes to 24 hours, and preferably 1 to 5 hours.

In the case the leaving group is a sulfonyl group, there are no particular limitations on the sulfonylation agent used provided it is normally used in reactions for sulfonylating a hydroxyl group, examples of which include alkanesulfonyl halides such as ethanesulfonyl chloride, arylsulfonyl halides such as p-toluenesulfonyl chloride, and sulfonic acid anhydrides such as methanesulfonic acid anhydride, benzenesulfonic acid anhydride or trifluoromethanesulfonic acid anhydride. Preferable examples include methanesulfonyl chloride, p-toluenesulfonyl chloride and trifluoromethanesulfonic acid anhydride.

There are no particular limitations on the solvent used provided it does not inhibit the reaction and dissolves the starting substance to a certain degree, examples of which include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; and, ethers such as diethyl ether, diisopropyl ether, tetrahydrofuran, dioxane, dimethoxyethane or diethylene glycol dimethyl ether. Preferable examples include halogenated hydrocarbons, esters and ethers, with tetrahydrofuran being particularly preferable.

There are no particular limitations on the base used provided it is used as a base in ordinary reactions, preferable examples of which include organic bases such as triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]nona-5-ene (DBN), 1,4-diazabicyclo[2.2.2]octane (DABCO) or 1,8-diazacyclo[5.4.0]undec-7-ene (DBU), while triethylamine or pyridine is more preferable.

The reaction temperature is 0° C. to the heating temperature (boiling point of the solvent used), and preferably 0° C. to room temperature.

The reaction time is 10 minutes to 24 hours, and preferably 10 minutes to 1 hour.

The reagent used as a reagent corresponding to the $R^1$ and $R^2$ groups is a commercially available reducing agent or halogenation agent and so forth.

Preferable examples of reducing agents used include alkaline metal borohydrides such as sodium borohydride or lithium borohydride, aluminum hydride compounds such as lithium aluminum hydride or lithium triethoxide aluminum hydride, and hydride reagents such as sodium tellurium hydride.

There are no particular limitations on the solvent used provided it does not inhibit the reaction and dissolves the starting substance, preferable examples of which include alcohols such as methanol or ethanol, ethers such as ether or tetrahydrofuran, and mixed solvents thereof.

There are no particular limitations on the halogenation agent used provided it is normally used in halogenation reactions, preferable examples of which include dialkylaminosulfate trihalides such as diethylaminosulfur trifluoride (DAST), thionyl halides such as thionyl chloride, thionyl bromide or thionyl iodide, sulfuryl halides such as sulfuryl chloride, sulfuryl bromide or sulfuryl iodide, phosphorus trihalides such as phosphorus trichloride, phosphorus tribromide or phosphorus triiodide, phosphorus pentahalides such as phosphorus pentachloride, phosphorus pentabromide or phosphorus pentaiodide, and phosphorus oxyhalides such as phosphorus oxychloride, phosphorus oxybromide or phosphorus oxyiodide, with diethylaminosulfur trifluoride being more preferable.

There are no particular limitations on the solvent used provided it does not inhibit the reaction and dissolves the starting substance to a certain degree, examples of which include ethers such as ether or tetrahydrofuran, with tetrahydrofuran being preferable.

The reaction temperature is 0° C. to the heating temperature (boiling point of the solvent used), and preferably room temperature to the heating temperature (boiling point of the solvent used).

The reaction time is 10 minutes to 24 hours, and preferably 1 to 5 hours.

(Step A2)

This step is for producing intermediate (iii), and is achieved by introducing a leaving group at position 1 of compound (ii) in compliance with the method of step A1.

(Step B)

(Method Ba)

Raw material compound (iv) can be produced in compliance with the method described in Tetrahedron, Vol. 26, 1985, p. 1469. Moreover, raw material compound (v) can be produced by protecting and de-protecting a hydroxyl group of a known compound in compliance with a known method. In addition, the hydroxyl group can be protected and de-protected as necessary in this step in the same manner as method A. Moreover, in the case of having a halogen atom for a substituent, a halogen atom can also be introduced in compliance with the halogenation reaction of step A1.

(Step Ba1)

This step is for producing bicyclic compound (v), and is achieved by reducing the azide group of compound (iv) followed by heating.

There are no particular limitations on the solvent used provided it does not inhibit the reaction and dissolves the starting substance to a certain degree, examples of which include water-soluble ethers such as tetrahydrofuran or dioxane, water, or mixtures thereof, with a mixture of water and tetrahydrofuran being preferable.

Examples of azide group reducing agents include phosphines and aqueous ammonia. Specific examples include trialkylphosphines such as trimethylphosphine or triethylphosphine and aqueous ammonia, or triarylphosphines such as triphenylphosphine and aqueous ammonia, with triarylphosphines such as triphenylphosphine and aqueous ammonia being preferable.

In addition, a catalyst can also be used for the reducing agent. There are no particular limitations on the catalyst used provided it is normally used in contact reduction reactions, examples of which include palladium carbon, palladium black, palladium carbon hydroxide, Rainey nickel, platinum oxide, platinum black, rhodium-aluminum oxide, triphenylphosphine-rhodium chloride or palladium-barium sulfate, with palladium carbon or palladium carbon hydroxide being preferable.

In the case of using a catalyst for the reducing agent, there are no particular limitations on the solvent used provided it does not inhibit the reaction and dissolves the starting substance, examples of which include alcohols such as methanol or ethanol, ethers such as tetrahydrofuran or dioxane, fatty acids such as acetic acid and esters such as ethyl acetate, with methanol being preferable.

The reaction temperature is 0 to 50° C., and preferably 0° C. to room temperature.

The reaction time is 10 minutes to 24 hours, and preferably 1 to 5 hours.

(Step Ba2)

This step is for producing compound (vi) in which the amino group is protected, and is achieved by protecting the amino group of compound (v) with a suitable protecting group.

There are no particular limitations on the solvent used provided it does not inhibit the reaction and dissolves the starting substance, preferable examples of which include ethers such as tetrahydrofuran, dioxane, dimethoxyethane or diethylene glycol, alcohols such as methanol or ethanol, ketones such as acetone or methyl ethyl ketone, amides such as N,N-dimethylformamide or N,N-dimethylacetamide, and sulfoxides such as dimethyl sulfoxide.

There are no particular limitations on the reagent used provided it is normally used in reactions for introducing a protecting group to a free amino group, preferable examples of which include di-t-butyl dicarbonate, benzyloxycarbonyl chloride and p-nitrobenzyloxycarbonyl chloride, with di-t-butyl dicarbonate being more preferable.

There are no particular limitations on the base used provided it is used as a base in ordinary reactions, preferable examples of which include alkaline metal carbonates, alkaline metal bicarbonates and organic bases, with alkaline metal bicarbonates being more preferable.

The reaction temperature is 0 to 50° C., and preferably 0° C. to room temperature.

The reaction time is 10 minutes to 24 hours, and preferably 1 to 10 hours.

(Step Ba3)

This step is for producing pyrrolidine compound (viia), and is achieved by opening one of the rings of the bicyclic compound (vi) in the presence of a reducing agent, protecting the hydroxyl group as necessary, and de-protecting the hydroxyl group at the site to be glycosylated with intermediate (iii).

There are no particular limitations on the reducing agent used provided it is normally used in reduction reactions, examples of which include alkaline metal borohydrides such as sodium borohydride or lithium borohydride, aluminum hydride compounds such as lithium aluminum hydride or lithium triethoxide aluminum hydride, and hydride reagents such as sodium tellurium hydride, with sodium borohydride being preferable.

There are no particular limitations on the solvent used provided it does not inhibit the reaction and dissolves the starting substance to a certain degree, examples of which include alcohols such as methanol or ethanol, ethers such as dioxane, ether or tetrahydrofuran, water, or mixed solvents thereof, with methanol or tetrahydrofuran being preferable.

The reaction temperature is 0° C. to the boiling point of the solvent used, and preferably 50° C. to the boiling point of the solvent used.

The reaction time is 10 minutes to 24 hours, and preferably 1 to 5 hours.

There are no particular limitations on the solvent used provided it does not inhibit the reaction and dissolves the starting substance, examples of which include alcohols such as methanol or ethanol, ethers such as ether or tetrahydrofuran, and mixed solvents thereof being preferable.

The reaction temperature is 0° C. to the boiling point of the solvent used, and preferably 50° C. to the boiling point of the solvent used.

The reaction time is 10 minutes to 24 hours, and preferably 1 to 5 hours.

(Method Bb)

The raw material compound (viii) can be produced in compliance with the method described in Carbohydrate Research, Vol. 169, 1987, p. 23. Moreover, raw material compound (viii) can be produced by protecting and de-protecting a hydroxyl group of a known compound according to a known method. In addition, the hydroxyl group can be protected and de-protected as necessary in this step in the same manner as method A. Moreover, in the case of having a halogen atom as a substituent, a halogen atom can also be introduced in compliance with the halogenation reaction of step A1.

(Step Bb1)

This step is for producing compound (ix), and is achieved by introducing a leaving group at position 6 of raw material compound (viii) under the same conditions as step A1. In addition, the leaving group can be converted to a different leaving group as necessary.

(Step Bb2)

This step is for producing a compound (x) having a terminal olefin group, and is achieved by heating compound (ix) in the presence of a catalyst in a solvent.

There are no particular limitations on the solvent used provided it does not inhibit the reaction and dissolves the starting substance, preferable examples of which include alcohols such as methanol, ethanol or isopropanol, water, or mixed solvents thereof, with a mixed solvent of water and isopropanol being more preferable.

There are no particular limitations on the catalyst used provided it is normally used in reactions for reducing double bonds, examples of which include zinc, palladium carbon, platinum, Rainey nickel, alkaline metal borohydrides such as sodium borohydride or lithium borohydride, aluminum hydride compounds such as lithium aluminum hydride or lithium triethoxide aluminum hydride, and hydride reagents such as sodium tellurium hydride, and zinc being preferable.

The reaction temperature is 0° C. to the boiling point of the solvent used, and preferably 50° C. to the boiling point of the solvent used.

The reaction time is 10 minutes to 24 hours, and preferably 1 to 5 hours.

(Step Bb3)

This step is for producing a compound (xi) having a hydroxylamino group, and is achieved by treating compound (x) with hydroxylamine hydrochloride.

There are no particular limitations on the solvent used provided it does not inhibit the reaction and dissolves the starting substance, preferable examples of which include mixed solvents of alcohols such as methanol, ethanol or isopropanol and organic bases such as pyridine, with a mixed solvent of ethanol and pyridine being more preferable.

The reaction temperature is 0° C. to the boiling point of the solvent used, and preferably 0 to 60° C.

The reaction time is 10 minutes to 24 hours, and preferably 1 to 5 hours.

(Step Bb4)

This step is for producing bicyclic compound (xii), and is achieved by cyclizing compound (xi) by heating in a solvent.

There are no particular limitations on the solvent used provided it is inert, preferable examples of which include aromatic hydrocarbons such as benzene, toluene or xylene, with toluene being more preferable.

The reaction temperature is 0° C. to the boiling point of the solvent used, and preferably 50° C. to the boiling point of the solvent used.

The reaction time is 10 minutes to 24 hours, and preferably 1 to 5 hours.

(Step Bb5)

This step is for producing intermediate compound (viib), and is achieved by de-protecting the hydroxyl group at the site to be glycosylated with intermediate (iii), and protecting the secondary amine of compound (xii) under the same conditions as step A1.

(Method Bc)

Raw material compound (xiii) can be produced in compliance with the method described in the Chemical Pharmaceutical Bulletin, Vol. 39, 1991, p. 2807. Moreover, raw material compound (xiii) can be produced by protecting and de-protecting a hydroxyl group of a known compound according to a known method. In addition, the hydroxyl group can be protected and de-protected as necessary in this step in the same manner as method A. Moreover, in the case of having a halogen atom for a substituent, a halogen atom can also be introduced in compliance with the halogenation reaction of step A1.

(Step Bc1)

This step is for producing intermediate compound (viic), and is achieved by de-protecting the protecting group of hydroxyl group of raw material compound (xiii).

(Step C)

(Step C1)

This step is for producing the target compound (I), and is achieved by glycosylating with intermediate compounds (iii) and (vii), and de-protecting the hydroxyl groups and amino groups as necessary in accordance with established methods.

Preferable examples of the leaving group at the anomeric position of compound (iii) include a fluorine atom, bromine atom, chlorine atom, trichloroimidate group, diphenylphosphate group, diethylphosphite group, thiomethyl group and phenylthio group.

There are no particular limitations on the solvent used provided it is inert, preferable examples of which include halogenated hydrocarbons such as methylene chloride or chloroform, ethers such as ether or tetrahydrofuran, and aromatic hydrocarbons such as benzene, toluene or xylene, with halogenated hydrocarbons or ethers being more preferable, and methylene chloride or ether being particularly preferable.

There are no particular limitations on the catalyst used provided it is normally used in glycosylation reactions, preferable examples of which include trimethylsilyl trifluoromethanesulfonic acid, trifluoromethanesulfonic acid, boron trifluoride-ether complex, toluenesulfonic acid, silver trifluoromethanesulfonic acid and tetrabutyl ammonium iodide.

The reaction temperature is 0° C. to the boiling point of the solvent used, and preferably room temperature.

The reaction time is 10 minutes to 24 hours, and preferably 1 to 5 hours.

In addition, target compound (I) can also be produced by glycosylating with intermediate compounds (iii) and (viic) followed by de-protecting the hydroxyl groups and further subjecting to basic conditions.

In addition, in the case n=2, compound (I) can also be produced using the same method as method A or method C by using a trisaccharide derivative as the raw material compound.

In addition, compound (I) can be converted to an acid addition salt, and preferably to a hydrochloride, in accordance with ordinary methods in the case of having a basic group.

Following completion of the reactions of each of the aforementioned steps, the target compound is recovered from the reaction mixture in accordance with conventional methods. For example, the target compound can be obtained by suitably neutralizing the reaction mixture, or removing insoluble matter by filtration in the case insoluble matter is present, followed by adding water and an immiscible organic solvent such as ethyl acetate, washing with water and so forth, separating the organic layer containing the target compound, drying with anhydrous magnesium sulfate and so forth, and distilling off the solvent.

The resulting target compound can be separated and purified as necessary using, for example, recrystallization, reprecipitation or other methods routinely used for separation and purification of organic compounds, including eluting with a suitable eluent by suitably combining methods such as methods using synthetic adsorbents such as adsorption column chromatography or partition column chromatography, methods using ion exchange chromatography, and forward phase and/or reverse phase column chromatography methods using a silica gel or alkylated silica gel.

In the present invention, one or more types of α-amylase inhibitor can be used. In addition, one or more types of insulin sensitizers, biguanide drugs, insulin secretagogues, insulin preparations and DPP-IV inhibitors can also be used.

The α-amylase inhibitor and at least one type of insulin sensitizer, biguanide drug, insulin secretagogue, insulin preparation and DPP-IV inhibitor can be administered in the form of a compounded agent. In addition, each single agent can also be administered simultaneously. In addition, each single agent can also be administered in early and late phases at suitable intervals. The allowed administration interval for the effects generated by administration of these drugs to be achieved can be confirmed through clinical or animal studies.

The pharmaceutical composition of the present invention is administered in various forms. There are no particular limitations on the administration form, and is determined corresponding to each type of preparation form, patient age, gender and other conditions, and the degree of the disease and so forth. For example, the pharmaceutical composition is administered orally in the case of tablets, pills, powders, granules, syrups, liquids, suspensions, emulsions and capsules.

Each of these preparations can be formulated using known assistants normally able to be used in known pharmaceutical preparation fields, such as vehicles, binders, disintegration agents, lubricants, dissolution agents, correctives and coating agents, with the primary drug in accordance with conventional methods.

When molding into the form of tablets, conventionally known carriers in this field can be widely used for the carrier, examples of which include vehicles such as lactose, sucrose, sodium chloride, glucose, urea, starch, calcium carbonate, kaolin, crystalline cellulose or silicic acid, binders such as water, ethanol, propanol, simple syrup, liquid glucose, liquid starch, gelatin solution, carboxymethyl cellulose, shellac, methyl cellulose, potassium phosphate or polyvinylpyrrolidone, disintegration agents such as dry starch, sodium alginate, powdered agar, powdered laminarin, sodium bicarbonate, calcium carbonate, polyoxyethylene sorbitan fatty acid esters, sodium lauryl sulfate, stearic acid monoglyceride, starch or lactose, disintegration suppressants such as sucrose, stearin, cacao butter or hydrogenated oils, absorption promoters such as quaternary ammonium salts or sodium lauryl sulfate, moisture retention agents such as glycerin or starch, adsorbents such as starch, lactose, kaolin, bentonite or colloidal silica, and lubricants such as purified talc, stearates, powdered boric acid or polyethylene glycol. Moreover, the tablets can be in the form of tablets provided with a conventional coating as necessary, examples of which include sugar-coated tablets, gelatin-encapsulated tablets, enteric tablets, film-coated tablets, double-layer tablets and multilayer tablets.

When molding into the form of pills, conventionally known carriers in this field can be widely used for the carrier, examples of which include vehicles such as glucose, lactose, starch, cocoa butter, hydrogenated vegetable oils, kaolin or talc, binders such as powdered gum arabic, powdered tragacanth, gelatin or ethanol, and disintegration agents such as laminarin agar.

Moreover, a colorant, preservative, fragrance, flavoring, sweetener or other pharmaceutical may also be contained as necessary.

Although there are no particular limitations on the amount of the active ingredient compound contained in the aforementioned pharmaceutical preparation, and it is suitably selected over a wide range, it is normally contained at 1 to 70% by weight, and preferably 1 to 30% by weight, of the total composition.

The doses and administration ratios of each of the diabetes therapeutic drugs used in the present invention can be altered over a wide range according to various conditions such as the activities of individual substances, and patient symptoms, age and body weight.

Although the dose of the diabetes therapeutic drug used in the present invention can be altered over a wide range as previously described, the normal adult daily dose has a lower limit of 0.0001 mg/kg (preferably 0.001 mg/kg, and more preferably 0.01 mg/kg), and has an upper limit of 30 mg/kg (preferably 3 mg/kg, and more preferably 1.5 mg/kg).

Although the administration ratios of the α-amylase inhibitor and other diabetes therapeutic drugs can also be altered over a wide range, they are normally within the range of a weight ratio of 0.001 to 100 (w/w).

In the present invention, the α-amylase inhibitor and other diabetes therapeutic drugs are respectively administered separately at the aforementioned doses once a day, or divided among several administrations either simultaneously or at different times.

According to the present invention, by using an α-amylase inhibitor in combination with other diabetes therapeutic drugs, superior blood glucose lowering action can be demonstrated against elevated blood glucose levels during diabetes, thereby enabling effective prevention and treatment of diabetes. In addition, said pharmaceutical is also effective against diabetes complications attributable to elevated blood glucose levels. Moreover, by suitably selecting the type of each drug, administration method and dose according to symptoms, stable blood glucose lowering action can be expected to be demonstrated even during extended administration, thereby enabling this pharmaceutical to serve as a preventive and therapeutic for the aforementioned diseases while having an extremely low incidence of adverse side effects.

BRIEF DESCRIPTION OF THE DRAWINGS

FIG. 1 is a graph showing the areas under the curve for increases in blood glucose levels in the case of combined use of an α-amylase inhibitor (compound A: compound of Reference Example No. 2) and an insulin secretagogue (nateglinide) (Test Example 2);

FIG. 2 is a graph showing the areas under the curve for increases in blood glucose levels in the case of combined use of an α-amylase inhibitor (compound A: compound of Reference Example No. 2) and an insulin preparation (Regular Insulin) (Test Example 3);

FIG. 3 is a graph showing a comparison of blood glucose levels in each group in the case of combined use of an α-amylase inhibitor (compound A: compound of Reference Example No. 2) and an insulin sensitizer (pioglitazone) (Test Example 4);

FIG. 4 is a graph showing a comparison of blood glucose levels in each group in the case of combined use of an α-amylase inhibitor (compound A: compound of Reference Example No. 2) and a biguanide drug (metformin) (Test Example 5); and, FIG. 5 is a graph showing the areas under the curve for increases in blood glucose levels in the case of combined use of an α-amylase inhibitor (compound A: compound of Reference Example No. 2) and a DPP-IV inhibitor (MK-0431) (Test Example 6).

BEST MODE FOR CARRYING OUT THE INVENTION

Although the following provides a more detailed explanation of the present invention through examples, test examples, reference examples and preparation examples thereof, the present invention is not limited thereto.

EXAMPLE

Test Example 1

α-Amylase Inhibitory Action
(1) Preparation of Human α-Amylase Solution

Calibzyme AMY (International Reagents Co., Ltd.) was used for the human pancreatic α-amylase (HPA). Distilled water was added to the commercially available HPA and dissolved to a concentration of 200 IU/l to prepare the α-amylase solution. The activity of the α-amylase was measured using a commercially available α-amylase assay reagent (Neo Amylase Test Daiichi, Daiichi Pure Chemicals Co., Ltd.).

(2) Preparation of Inhibitory Solutions

Each test compound was prepared with distilled water to a final concentration of 0.1 to 30 µg/ml.

(3) Measurement of Human α-Amylase Inhibitory Activity of Inhibitory Solutions 3.78 to 3.9 ml of distilled water and 0 to 120 µl of inhibitory solution were added to 100 µl of HPA solution to be adjusted to a total volume of 4 ml. After incubating for 10 minutes at 37° C., a Blue Starch tablet (Neo Amylase Test Daiichi, Daiichi Pure Chemicals Co., Ltd.) was added followed by stirring for about 10 seconds with a mixer, and the mixture was then heated for 30 minutes at 37° C. Subsequently, 1.0 ml of 0.5 N aqueous sodium hydroxide solution was added and stirred to stop the reaction followed by centrifuging (1,500 G, 5 minutes) and the optical absorbance of the supernatant at 620 nm was measured. A mixture to which inhibitory solution had not been added was used as a control. In addition, a mixture to which distilled water was added instead of α-amylase solution was used as a blank. The inhibition rate was calculated using the equation indicated below, and the final concentration (µg/ml) of test compound required for 50% inhibition of the activity of the HPA solution is shown in Table 1 as the $IC_{50}$ value.

Inhibition rate(%)=[1−{(absorbance of control)−(absorbance of blank)}/{(absorbance when inhibitor added)−(absorbance of blank)}]×100  [Equation 1]

TABLE 1

| Reference Example No. | IC$_{50}$ (μg/ml) |
|---|---|
| 1 | $7 \times 10^{-1}$ |
| 2 | $2 \times 10^{-1}$ |
| 3 | $4 \times 10^{-1}$ |
| 4 | $3 \times 10^{-1}$ |
| 5 | 7 |
| 7 | 4 |
| 8 | $4 \times 10^{-1}$ |
| 9 | $3 \times 10$ |
| 11 | $1 \times 10$ |
| 13 | 4 |
| 14 | 1 |
| 15 | $6 \times 10^{-1}$ |
| 17 | $3 \times 10$ |
| 18 | $2 \times 10^{-3}$ |
| 19 | $6 \times 10^{-1}$ |

According to Table 1, compounds having general formula (I) were determined to have superior α-amylase inhibitory action.

Test Example 2

Effects of Combined Use of α-Amylase Inhibitor (Compound A: Compound of Reference Example No. 2) and Insulin secretagogue (Nateglinide)

(1) Animals Used

Commercially available obese rats (Zucker fatty rats, males, age at time of use: 16 weeks, supplier: Japan Charles River) were used.

(2) Experimental Method and Results

The rats (5 to 6 animals/group) were used in the study after fasting overnight, and were orally administered starch suspended in a solvent (0.5% methyl cellulose solution) by gavage at a dose of 2 g/10 ml/kg, followed by evaluating the subsequent increases in blood glucose levels.

Animals orally administered the solvent (5 mL/kg) 5 minutes prior to starch administration were used as a control group.

Animals of the nateglinide group were orally administered a nateglinide dosing solution at a dose of 20 mg/5 ml/kg 5 minutes prior to starch administration.

Animals of the compound A dose group were orally administered the solvent (5 mL/kg) 5 minutes prior to starch administration, and then orally administered compound A mixed in a starch solution at a dose of 0.1 mg/10 mL/kg by gavage at the time of starch administration.

Animals of the combination group were orally administered the nateglinide dosing solution at a dose of 20 mg/5 mL/kg 5 minutes prior to starch administration, and then orally administered compound A mixed in the starch solution at a dose of 0.1 mg/10 mL/kg by gavage at the time of starch administration.

Blood glucose levels were measured before starch administration and at 0.5, 1, 2 and 3 hours after starch administration. Blood samples were collected from the tail vein of the rats, blood glucose levels were measured using a simple glucose analyzer (Glucoloader GXT, A & T Co., Ltd.), and the areas under the curve were calculated for the increases in blood glucose levels, the results of which are shown in FIG. 1.

According to FIG. 1, prominent activity which inhibited increases in blood glucose levels was determined to be demonstrated by combined use of the α-amylase inhibitor and insulin secretagogue as compared with the use of either alone. Thus, since a pharmaceutical of the present invention lowers blood glucose levels during diabetes even more effectively than administration of a single drug alone, it is useful for the prophylaxis and treatment of diabetes. In addition, since a pharmaceutical of the present invention allows the obtaining of adequate effects even if used in a smaller amount when compared with the case of administration of each drug alone, adverse side effects associated with insulin secretagogues during the treatment of diabetes (such as hypoglycemia, pancreatic β-cell damage, liver function disorders and weight gain) can be diminished.

Test Example 3

Combination Effects of α-Amylase Inhibitor (Compound A: Compound of Reference Example No. 2) and Insulin Preparation (Regular Insulin)

(1) Animals Used

Commercially available diabetic rats (Goto-Kakizaki rats, males, age at time of use: 31 weeks, supplier: Japan Charles River) were used.

(2) Experimental Method and Results

The rats (4 to 5 animals/group) were used in the study after fasting overnight, and were orally administered starch suspended in a solvent (0.5% carboxymethyl cellulose solution) by gavage at a dose of 2 g/10 ml/kg, followed by evaluating the subsequent increases in blood glucose levels.

Animals subcutaneously administered physiological saline (1 mL/kg) just before starch administration were used as a control group.

Animals of the insulin group were subcutaneously administered an insulin dosing solution (regular insulin) at a dose of 0.25 U/1 mL/kg just before starch administration.

Animals of the compound A dose group were subcutaneously administered physiological saline (1 mL/kg) immediately prior to starch administration, and then orally administered compound A mixed in a starch solution at a dose of 0.05 mg/10 mL/kg by gavage at the time of starch administration.

Animals of the combination group were subcutaneously administered the insulin dosing solution (regular insulin) at a dose of 0.25 U/1 mL/kg just before starch administration, and then orally administered compound A mixed in the starch solution at a dose of 0.05 mg/10 mL/kg by gavage at the time of starch administration.

Blood glucose levels were measured before starch administration and at 0.5, 1, 2 and 4 hours after starch administration. Blood samples were collected from the tail vein of the rats, blood glucose levels were measured using a simple glucose analyzer (Glucoloader GXT, A & T Co., Ltd.), and the areas under the curve were calculated for the increases in blood glucose levels, the results of which are shown in FIG. 2.

According to FIG. 2, prominent activity which inhibited increases in blood glucose levels was determined to be demonstrated by combined use of the α-amylase inhibitor and insulin preparation as compared with the use of either alone. Thus, since a pharmaceutical of the present invention lowers blood glucose levels during diabetes even more effectively than administration of a single drug alone, it is useful for the prevention and treatment of diabetes. In addition, since a pharmaceutical of the present invention allows the obtaining of adequate effects even if used in a smaller amount when compared with the case of administration of each drug alone, adverse side effects associated with insulin preparations during the treatment of diabetes (such as hypoglycemia and weight gain) can be diminished.

Test Example 4

Combination Effects of α-Amylase Inhibitor (Compound A: Compound of Reference Example No. 2) and Insulin Sensitizer (Pioglitazone)

(1) Animals Used

Commercially available diabetic mice (db/db mice, males, age at time of use: 7 weeks, supplier: Clea Japan, Inc.) were used.

(2) Experimental Method and Results

The mice were grouped into groups of 5 animals each. Animals of the control group were given unlimited access to a powdered feed (FR-2 Powdered Feed, Funabashi Farms Co., Ltd.) for 2 weeks. Animals of the pioglitazone group and the combination group were given unlimited access to the powdered feed mixed to a concentration of 50 ppm with pioglitazone, while animals of the compound A group and the combination group were given free access to the powdered feed mixed to a concentration of 100 ppm with compound A.

Blood glucose levels were measured 2 weeks after beginning administering the compound, and those results are shown in FIG. 3. Blood samples were collected from the tail vein of the rats, and blood glucose levels were measured using a simple glucose analyzer (Glucoloader GXT, A & T Co., Ltd.)

According to FIG. 3, prominent activity which lowered blood glucose levels was determined to be demonstrated by combined use of the α-amylase inhibitor and insulin sensitizer as compared with the use of either alone. Thus, since a pharmaceutical of the present invention lowers blood glucose levels during diabetes even more effectively than administration of a single drug alone, it is useful for the prevention and treatment of diabetes. In addition, since a pharmaceutical of the present invention allows the obtaining of adequate effects even if used in a smaller amount when compared with the case of administration of each drug alone, adverse side effects associated with insulin sensitizers during the treatment of diabetes (such as weight gain, cardiac hypertrophy, edema and liver function disorders) can be diminished.

Test Example 5

Combination Effects of α-Amylase Inhibitor (Compound A: Compound of Reference Example No. 2) and Biguanide Drug (Metformin)

(1) Animals Used

Commercially available diabetic rats (Goto-Kakizaki rats, males, age at time of use: 29 weeks, supplier: Japan Charles River) were used.

(2) Experimental Method and Results

The rats were grouped into groups of 5 animals each. Animals of the control group were given unlimited access to a powdered feed (FR-2 Powdered Feed, Funabashi Farms Co., Ltd.) for 2 weeks. Animals of the metformin group and the combination group were given unlimited access to the powdered feed mixed to a concentration of 300 ppm with metformin (Sigma-Aldrich Japan Co., Ltd.), while animals of the compound A group and the combination group were given free access to the powdered feed mixed to a concentration of 40 ppm with compound A.

Blood glucose levels were measured 2 weeks after beginning administering the compound, and those results are shown in FIG. 4. Blood samples were collected from the tail vein of the rats, and blood glucose levels were measured using a simple glucose analyzer (Glucoloader GXT, A & T Co., Ltd.)

According to FIG. 4, prominent activity which lowered blood glucose levels was determined to be demonstrated by combined use of the α-amylase inhibitor and biguanide drug (and preferably metformin) as compared with the use of either alone. Thus, since a pharmaceutical of the present invention lowers blood glucose levels during diabetes even more effectively than administration of a single drug alone, it is useful for the prevention and treatment of diabetes. In addition, since a pharmaceutical of the present invention allows the obtaining of adequate effects even if used in a smaller amount when compared with the case of administration of each drug alone, adverse side effects associated with biguanide drugs during the treatment of diabetes (such as digestive tract disorders, lactic acidosis and rashes) can be diminished.

Test Example 6

Combination Effects of α-Amylase Inhibitor (Compound A: Compound of Reference Example No. 2) and DPP-IV Inhibitor (MK-0431)

(1) Animals Used

Commercially available diabetic mice (KKAy mice, males, age at time of use: 6 weeks, supplier: Clea Japan, Inc.) were used.

(2) Experimental Method and Results

The mice were grouped into groups of 4 animals each. Animals of control group were orally administered distilled water (10 mL/kg) one hour before administration of a saccharide (1 g of glucose+2 g of cornstarch/10 mL/kg of body weight). Animals of the MK-0431 group were orally administered an aqueous solution of MK-0431 at a dose of 1 mg/10 mL/kg one hour before saccharide administration. Animals of the compound A group were orally administered distilled water (10 mL/kg) one hour before saccharide administration, and then orally administered compound A by mixing into the saccharide solution at a dose of 0.05 mg/10 mL/kg at the time of saccharide administration. Animals of the combination group were orally administered the MK-0431 aqueous solution at a dose of 1 mg/10 mL/kg one hour before saccharide administration, and then orally administered compound A by mixing into the saccharide solution at a dose of 0.05 mg/10 mL/kg at the time of saccharide administration.

Blood glucose levels were measured before saccharide administration and at 0.5, 1, 2 and 3 hours after saccharide administration. Blood samples were collected from the tail vein of the mice, blood glucose levels were measured using a simple glucose analyzer (Glucoloader GXT, A & T Co., Ltd.), and the areas under the curve were calculated for the increases in blood glucose levels, the results of which are shown in FIG. 5.

According to FIG. 5, prominent activity which lowered blood glucose levels was determined to be demonstrated by combined use of the α-amylase inhibitor and DPP-IV inhibitor as compared with the use of either alone. Thus, since a pharmaceutical of the present invention lowers blood glucose levels during diabetes even more effectively than administration of a single drug alone, it is useful for the prevention and treatment of diabetes. In addition, since a pharmaceutical of the present invention allows the obtaining of adequate effects even if used in a smaller amount when compared with the case of administration of each drug alone, adverse side effects associated with DPP-IV inhibitors during the treatment of diabetes (such as loss of appetite, malaise, liver function disorders and immunodeficiency) can be diminished.

According to the results described above, a pharmaceutical of the present invention was determined to have remarkably enhanced effects in comparison with effects during administration of each drug alone.

Reference Example 1

(2R,3R,4R)-4-Hydroxy-2-(hydroxymethyl)pyrrolidin-3-yl 4-O-(6-deoxy-α-D-glucopyranosyl)-α-D-glucopyranoside (1a) Allyl 4-O-(2,3,4,6-tetra-O-acetyl-α-D-glucopyranosyl)-2,3,6-tri-O-acetyl-D-glucopyranoside D-Maltose mono-hydrate (36.0 g, 100 mmol) was dissolved in pyridine (200 mL) and acetic anhydride (100 mL) and 4-dimethylaminopyridine (0.6 g, 4.90 mol) were added thereto, followed by stirring of the mixture at room temperature for 12 hours. The reaction mixture was ice-cooled, ice (30 g) was added thereto and after the mixture was stirred for 30 minutes, it was extracted with ethyl acetate (500 mL). The organic layer was washed with diluted hydrochloric acid (1N, 200 mL), a saturated aqueous sodium hydrogencarbonate solution (100 mL) and a saturated aqueous NaCl solution (100 mL). After it was dried with anhydrous sodium sulfate, the solvent was distilled off under reduced pressure. The residue was dissolved in methylene chloride (700 mL), and allyl alcohol (34 mL, 500 mol) and trimethylsilyl trifluoromethanesulfonate (18.1 mL, 100 mmol) were added thereto, followed by stirring of the mixture at room temperature for 2 hours. The reaction mixture was added to a saturated aqueous sodium hydrogencarbonate solution (1 L) and after the mixture was extracted with methylene chloride (500 mL), the organic layer was washed with a saturated aqueous NaCl solution (300 mL). After it was dried with anhydrous sodium sulfate, the solvent was distilled off under reduced pressure. The residue was purified using silica gel flash column chromatography (ethyl acetate:hexane, 2:3, V/V) to obtain the desired title compound (30.0 g, yield: 31%) as a pale yellow amorphous substance.

$^1$H NMR (400 MHz, CDCl$_3$): δ 1.99 (3H, s), 2.00 (3H, s), 2.01 (6H, s), 2.03 (3H, s), 2.09 (3H, s), 2.14 (3H, s), 3.65-3.69 (1H, m), 3.93-4.14 (4H, m), 4.20-4.26 (2H, m), 4.30 (1H, dd, J=13.2, 5.1 Hz), 4.47 (1H, dd, J=12.4, 2.9 Hz), 4.57 (1H, d, J=8.1 Hz), 4.83-4.87 (2H, m), 5.04 (1H, t, J=9.5 Hz), 5.18-5.28 (3H, m), 5.35 (1H, t, J=9.5 Hz), 5.41 (1H, d, J=3.7 Hz), 5.79-5.88 (1H, m);

MS (FAB) m/z: 677 (M+H)$^+$, 699 (M+Na)$^+$.

(1b) Allyl 4-O-(4,6-O-benzylidene-α-D-glucopyranosyl)-D-glucopyranoside

The compound (17.0 g, 25.1 mmol) synthesized in Reference example 1 (1a) was dissolved in methanol (250 mL) and sodium methoxide (2 mL, 9.8 mol) was added thereto under ice-cooling, followed by stirring of the mixture at room temperature for 1 hour. Dowex 50w×8 was added to the reaction mixture until the reaction mixture became neutral and after the mixture was filtered, the solvent was distilled off under reduced pressure. The residue was dissolved in N,N-dimethylformamide (200 mL), and benzaldehyde dimethylacetal (4.65 mL, 31.0 mmol) and p-toluenesulfonic acid monohydrate (226 mg, 1.19 mmol) were added thereto, followed by stirring of the mixture at 50° C. at 20 mmHg for 5 hours. After triethylamine (1 mL) was added to the reaction mixture, the solvent was distilled off under reduced pressure. The residue was purified using silica gel flash column chromatography (ethyl acetate:hexane:methanol, 5:5:1, V/V/V) to obtain the desired title compound (10.0 g, yield: 85%) as a pale yellow amorphous substance.

$^1$H NMR (400 MHz, CD$_3$OD): δ 3.16 (1H, t, J=9.5 Hz), 3.28-3.32 (1H, m), 3.35 (1H, t, J=9.5 Hz), 3.42 (1H, t, J=9.5 Hz), 3.47 (1H, dd, J=9.5, 3.6 Hz), 3.54 (1H, t, J=9.5 Hz), 3.61-3.66 (2H, m), 3.71 (1H, t, J=9.5 Hz), 3.74-3.81 (2H, m), 4.02-4.07 (1H, m), 4.12 (1H, dd, J=10.3, 5.1 Hz), 4.22-4.29 (2H, m), 5.06 (1H, d, J=10.2 Hz), 5.10 (1H, d, J=4.4 Hz), 5.23 (1H, d, J=17.5 Hz), 5.81-5.91 (1H, m), 7.22-7.24 (3H, m), 7.38-7.40 (2H, m); MS (FAB) m/z: 471 (M+H)$^+$, 493 (M+Na)$^+$.

(1c) Allyl 4-O-(4,6-O-benzylidene-2,3-di-O-benzyl-α-D-glucopyranosyl)-2,3,6-tri-O-benzyl-D-glucopyranoside The compound (10.0 g, 21.3 mmol) synthesized in Reference example 1 (1b) was dissolved in N,N-dimethylformamide (300 mL) and sodium hydride (9.28 g, 213 mmol) was added thereto under ice-cooling. After the mixture was stirred under ice-cooling for 30 minutes, benzyl bromide (25 mL, 213 mmol) was added thereto and the mixture was stirred at room temperature for 3 hours. Water (100 mL) was added to the reaction mixture and the mixture was extracted with ethyl acetate (500 mL). The extract was washed with water (100 mL) and a saturated aqueous NaCl solution (100 mL) and it was dried with anhydrous sodium sulfate, and then the solvent was distilled off under reduced pressure. The residue was purified using silica gel flash column chromatography (hexane:ethyl acetate, 9:1, V/V) to obtain the desired title compound (18.5 g, yield: 94%) as a pale yellow solid.

$^1$H NMR (400 MHz, CDCl$_3$): δ 3.49-3.68 (4H, m), 3.76-3.90 (3H, m), 3.93-4.03 (2H, m), 4.09-4.19 (3H, m), 4.42-4.78 (10H, m), 4.84-5.07 (3H, m), 5.23 (1H, t, J=9.8 Hz), 5.35 (1H, dd, J=17.5, 8.8 Hz), 5.54 (1H, d, J=3.9 Hz), 5.74 (1H, dd, J=24.5, 3.9 Hz), 5.92-6.02 (1H, m), 7.17-7.51 (5H, m);

MS (FAB) m/z: 922 (M+H)$^+$, 944 (M+Na)$^+$.

(1d) Allyl 2,3,6-tri-O-benzyl-4-O-(2,3,4-tri-O-benzyl-α-D-glucopyranosyl)-D-glucopyranoside The compound (30.0 g, 32.5 mmol) synthesized in Reference example 1 (1c) was dissolved in diethyl ether (300 mL) and methylene chloride (150 mL), and lithium aluminum hydride (1.85 g, 48.8 mmol) and aluminum chloride (III) (6.93 g, 52.0 mmol) were added thereto, followed by heating under reflux of the mixture for 2 hours. After the reaction mixture was diluted with diethyl ether (500 mL), 1N aqueous sodium hydroxide solution (5.6 mL) was added to the reaction mixture and the mixture was stirred for 1 hour. After the reaction mixture was extracted with ethyl acetate, the organic layer was washed with 10% aqueous hydrochloric acid solution (100 mL), a saturated aqueous sodium hydrogencarbonate solution (150 mL) and a saturated aqueous NaCl solution (100 mL) and it was dried with anhydrous sodium sulfate, the solvent was distilled off under reduced pressure. The residue was purified using silica gel flash column chromatography (hexane:ethyl acetate, 4:1-3:1-2:1, V/V) to obtain the desired title compound (21.1 g, yield: 71%) as a pale yellow solid.

$^1$H NMR (400 MHz, CDCl$_3$): δ 3.40-3.71 (6H, m), 3.74-3.85 (2H, m), 3.90 (2H, m), 3.99-4.07 (1H, m), 4.10-4.20 (3H, m), 4.42-4.70 (7H, m), 4.76-5.08 (6H, m), 5.23 (1H, t, J=10.7

Hz), 5.35 (1H, dd, J=18.6, 8.8 Hz), 5.64 (1H, dd, J=13.7, 3.9 Hz), 5.93-6.02 (1H, m), 7.18-7.34 (30H, m);
MS (FAB) m/z: 946 (M+Na)$^+$, 924 (M+H)$^+$.

(1e) Allyl 2,3,6-tri-O-benzyl-4-O-(2,3,4-tri-O-benzyl-6-deoxy-α-D-glucopyranosyl)-D-glucopyranoside The compound (15.2 g, 16.5 mmol) synthesized in Reference example (1 (1d) was dissolved in pyridine (300 mL), and p-toluenesulfonyl chloride (12.5 g, 66.0 mmol) and 4-dimethylaminopyridine (2.01 g, 16.4 mmol) were added thereto, followed by stirring of the mixture at room temperature for 13 hours. After the solvent was distilled off under reduced pressure, the residue was poured into 10% aqueous hydrochloric acid solution (50 mL) and ethyl acetate (200 mL), and the organic layer was washed with 10% aqueous hydrochloric acid solution (50 mL), a saturated aqueous sodium hydrogencarbonate solution (20 mL) and a saturated aqueous NaCl solution (20 mL). After it was dried with anhydrous sodium sulfate, the solvent was distilled off under reduced pressure. The residue was purified using silica gel flash column chromatography (hexane:ethyl acetate, 5:1-3:1, V/V) to obtain tosylate (13.5 g, yield: 76%) as a yellow oil. The tosylate (13.5 g, 12.5 mol) was dissolved in diethyl ether (300 mL) and lithium aluminum hydride (950 mg, 25 mol) was added thereto, followed by heating under reflux of the mixture for 1 hour. 1N aqueous NaOH solution (1.0 mL) and water (1.0 mL) were added to the reaction mixture and the mixture was stirred for 30 minutes. After the reaction mixture was filtered through Celite, the solvent was distilled off under reduced pressure. The residue was purified using silica gel flash column chromatography (hexane:ethyl acetate, 6:1, V/V) to obtain the desired title compound (10.2 g, yield: 90%) as a colorless solid.
$^1$H NMR (400 MHz, CDCl$_3$): δ 1.08 (3H, d, J=5.8 Hz), 3.01 (1H, t, J=9.5 Hz), 3.35 (1H, dd, J=9.5, 3.7 Hz), 3.44-3.50 (2H, m), 3.66-3.72 (5H, m), 3.78 (1H, t, J=9.5 Hz), 3.93 (1H, t, J=9.5 Hz), 4.07 (1H, dd, J=12.8, 5.9 Hz), 4.35 (1H, dd, J=13.1, 5.1 Hz), 4.39-4.57 (7H, m), 4.69 (2H, d, J=11.7 Hz), 4.77-4.88 (3H, m), 5.13 (1H, d, J=10.0 Hz), 5.26 (1H, d, J=16.9 Hz), 5.47 (1H, d, J=3.7 Hz), 5.84-5.92 (1H, m), 7.09-7.26 (30H, m);
MS (FAB) m/z: 907 (M+H)$^+$.

(1f) 4-O-(6-Deoxy-2,3,4-tri-O-benzyl-α-D-glucopyranosyl)-2,3,6-tri-O-benzyl-D-glucopyranoside The compound (10.2 g, 11.2 mmol) synthesized in Reference example 1 (1e) was dissolved in methanol (40 mL) and tetrahydrofuran (100 mL) and palladium chloride (II) (400 mg, 2.24 mmol) was added thereto, followed by stirring of the mixture at room temperature for 14 hours. After the reaction mixture was filtered through Celite, the solvent was distilled off under reduced pressure. The residue was purified using silica gel flash column chromatography (hexane:ethyl acetate, 5:1-4:1, V/V) to obtain the desired title compound (8.17 g, yield: 84%) as a pale yellow amorphous substance.
$^1$H NMR (400 MHz, CDCl$_3$): δ 1.14 (3H, d, J=6.6 Hz), 3.09 (1H, t, J=9.5 Hz), 3.41-3.47 (2H, m), 3.62-3.81 (4H, m), 3.96-4.05 (2H, m), 4.01-4.14 (1H, m), 4.49-4.68 (6H, m), 4.74-4.78 (2H, m), 4.84-4.96 (4H, m), 5.22 (1H, d, J=3.6 Hz), 5.51 (1H, d, J=3.7 Hz), 7.19-7.34 (30H, m);
MS (FAB) m/z: 889 (M+Na)$^+$.

(1g) Methyl 3-O-benzoyl-N-benzyloxycarbonyl-2,5-dideoxy-2,5-imino-α-D-lixofuranoside Methyl N-benzyloxycarbonyl-2,5-dideoxy-2,5-imino-α-D-lixofuranoside (Tetrahedron, 1986, vol 42, pp. 5685-5692) (13.9 g, 49.8 mmol) was dissolved in methylene chloride (200 mL), and pyridine (20 mL, 249.0 mmol) and benzoyl chloride (11.6 mL, 99.6 mmol) were added thereto, followed by stirring of the mixture at room temperature for 2 hours. 1N Hydrochloric acid (200 mL) was added to the reaction mixture at 0° C. and after the mixture was extracted with methylene chloride (100 mL), the organic layer was washed with a saturated aqueous sodium hydrogencarbonate solution (200 mL) and a saturated aqueous NaCl solution (200 mL). After it was dried with anhydrous sodium sulfate, the solvent was distilled off under reduced pressure. The residue was purified using silica gel flash column chromatography (hexane:ethyl acetate, 5:1-3:1, V/V) to obtain the desired title compound (15.82 g, yield: 83%) as a colorless solid.
$^1$H NMR (400 MHz, CDCl$_3$): δ 3.42-3.46 (4H, 3s), 3.60 (1H, dd, J=32.2, 10.8 Hz), 4.54 (1H, d, J=34.2 Hz), 4.64 (1H, br, d, J=7.9 Hz), 4.85 (1H, d, J=36.2 Hz), 5.13-5.22 (2H, m), 5.47 (1H, s), 7.29-7.35 (5H, m), 7.41-7.45 (2H, m), 7.59 (1H, t, J=7.8 Hz), 7.95 (2H, t, J=7.8 Hz);
MS (FAB) m/z: 406 (M+Na)$^+$, 384 (M+H)$^+$.

(1h) Benzyl (2R,3R,4R)-3-benzoyloxy-4-hydroxy-2-(hydroxymethyl)pyrrolidine-1-carboxylate The compound (15.8 g, 41.3 mmol) synthesized in Reference example 1 (1g) was dissolved in trifluoroacetic acid: water (4:1, 160 mL) and the mixture was stirred at room temperature for 15 minutes. Water (200 mL) was added to the reaction mixture at 0° C. and after the mixture was extracted with methylene chloride (300 mL), the organic layer was washed with a saturated aqueous sodium hydrogencarbonate solution (200 mL) and a saturated aqueous NaCl solution (200 mL). After it was dried with anhydrous sodium sulfate, the solvent was distilled off under reduced pressure. The residue was dissolved in ethanol (150 mL) and a reagent in which sodium borohydride (0.78 g, 20.7 mmol) was dissolved in water (15 mL) was added thereto, followed by stirring of the mixture at 0° C. for 20 minutes. After a saturated aqueous NaCl solution (20 mL) was added to the reaction mixture at 0° C., ethanol was distilled off under reduced pressure. Water (100 mL) was added thereto and after it was extracted with ethyl acetate (100 mL), the organic layer was washed with a saturated aqueous NaCl solution (100 mL). After it was dried with anhydrous sodium sulfate, the solvent was distilled off under reduced pressure. The residue was purified using silica gel flash column chromatography (hexane:ethyl acetate, 1:1, V/V) to obtain the desired title compound (14.2 g, yield: 89%) as a colorless oil.
$^1$H NMR (400 MHz, CDCl$_3$): δ 3.68 (1H, d, J=11.7 Hz), 3.86 (1H, dd, J=11.7, 4.4 Hz), 3.93-4.04 (2H, m), 4.25-4.32 (2H, m), 5.09-5.32 (3H, m), 7.32-7.46 (7H, m), 7.59 (1H, t, J=7.4 Hz), 7.99 (2H, d, J=8.8 Hz);
MS (FAB) m/z: 372 (M+H)$^+$.

(1i) Benzyl (2R,3R,4R)-4-benzyloxy-2-benzyloxymethyl-3-hydroxypyrrolidine-1-carboxylate The compound (4.26 g, 11.5 mmol) synthesized in Reference example 1 (1h) was dissolved in dichloromethane:cyclohexane (1:2, 180 mL), and benzyl trichloroacetimidate (10.6 mL, 57.5 mmol) and trifluoromethanesulfonic acid (0.15 mL, 1.7 mmol) were added thereto, followed by stirring of the mixture at room temperature for 3 hours. A saturated aqueous sodium hydrogencarbonate solution (10 mL) was added to the reaction mixture at 0° C. and after the mixture was diluted with ethyl acetate (200 mL), it was washed with water (300 mL) and a saturated aqueous NaCl solution (300 mL). After it was dried with anhydrous sodium sulfate, the solvent was distilled off under reduced pressure. The residue was purified using silica gel flash column chromatography (hexane:ethyl acetate, 10:1-5:1, V/V) to obtain 7.85 g of pale yellow oil. 7.85 g of the thus obtained yellow oil was dissolved in methanol (100 mL) and 1M aqueous potassium carbonate solution (4 mL) was added thereto, followed by stirring of the mixture at room temperature for 5 hours. After methanol was distilled off under reduced pressure, water (100 mL) was added thereto and the mixture was extracted with ethyl acetate (100 mL). The organic layer was washed with a saturated aqueous NaCl solution (100 mL). After it was dried with anhydrous sodium sulfate, the solvent was distilled off under reduced pressure. The residue was purified using silica gel flash column chromatography (hexane:ethyl acetate, 2:1, V/V) to obtain the desired title compound (4.06 g, yield: 64%) as a colorless solid.

$^1$H NMR (400 MHz, CDCl$_3$): δ 3.35 (1H, dd, J=11.7, 3.7 Hz), 3.51-3.72 (1H, m), 3.66-3.89 (4H, m), 4.37-4.52 (5H, m), 4.98-5.07 (2H, m), 7.09-7.26 (15H, m);

MS (FAB) m/z: 448 (M+H)$^+$.

(1j) Benzyl (2R,3R,4R)-4-benzyloxy-2-benzyloxymethyl-3-{[2,3,6-tri-O-benzyl-4-O-(2,3,4-tri-O-benzyl-6-deoxy-α-D-glucopyranosyl)-α-D-glucopyranosyl]oxy}pyrrolidine-1-carboxylate Benzyl (2R,3R,4R)-4-benzyloxy-2-benzyloxymethyl-3-{[2,3,6-tri-O-benzyl-4-O-(2,3,4-tri-O-benzyl-6-deoxy-α-D-glucopyranosyl)-β-D-glucopyranosyl]oxy}pyrrolidine-1-carboxylate The compound (13.5 g, 15.57 mmol) synthesized in Reference example 1 (1f) was dissolved in methylene chloride (250 mL), and trichloroacetonitrile (10 mL, 134.3 mmol) and 1,8-diazabicyclo[5.4.0]-7-undecene (2 drops) were added thereto, followed by stirring of the mixture at room temperature for 40 minutes. After the solvent was distilled off under reduced pressure, it was purified using silica gel flash column chromatography (hexane:ethyl acetate, 5:1, 1% triethylamine, V/V) to obtain imidate (13.0 g, 82%) as a yellow oil. The compound (5.48 g, 12.2 mmol) synthesized in Reference example 1 (1i) was dissolved in diethyl ether (400 mL) and the imidate (13.0 g, 13.0 mmol) was added thereto. A solution of trimethylsilyl trifluoromethanesulfonate (222 μl, 1.22 mmol) in diethyl ether (2 mL) was added dropwise to the mixture and the mixture was stirred at room temperature for 45 minutes. After triethylamine (1 mL) was added to the reaction mixture, the solvent was distilled off under reduced pressure. The residue was purified using silica gel flash column chromatography (hexane:diethyl ether, 4:1, V/V) to obtain the α isomer of the desired title compound (11.6 g, 56%) as a pale yellow oil and its β isomer (3.7 g, 18%) as a pale yellow oil.

α isomer: $^1$H NMR (400 MHz, CDCl$_3$): δ 1.20 (3H, d, J=5.9 Hz), 3.10-3.22 (2H, m), 3.30-3.38 (2H, m), 3.42 (1H, t, J=8.8 Hz), 3.50-3.70 (5H, m), 3.76-3.87 (5H, m), 4.01-4.10 (1H, m), 4.26-4.51 (9H, m), 4.61 (1H, d, J=11.0 Hz), 4.69-4.88 (8H, m), 4.96-5.16 (3H, m), 7.19-7.34 (43H, m), 7.43 (2H, d, J=7.3 Hz);

MS (FAB) m/z: 1318 (M+Na)$^+$.

β isomer: $^1$H NMR (400 MHz, CDCl$_3$): δ 1.17 (3H, d, J=6.5 Hz), 3.10 (1H, t, J=9.1 Hz), 3.41-3.48 (3H, m), 3.54-3.63 (3H, m), 3.69-3.78 (4H, m), 3.81-3.92 (2H, m), 4.02 (1H, s, J=8.79 Hz), 4.25 (1H, d, J=4.39 Hz), 4.40-4.63 (13H, m), 4.73-4.79 (3H, m), 4.86-4.95 (4H, m), 5.09-5.19 (1H, m), 5.53 (1H, d, J=3.67 Hz), 7.18-7.30 (45H, m);

MS (FAB) m/z: 1296 (M+H)$^+$.

(1k) (2R,3R,4R)-4-Hydroxy-2-(hydroxymethyl)pyrrolidin-3-yl 4-O-(6-deoxy-α-D-glucopyranosyl)-α-D-glucopyranoside The compound (5.60 g, 4.32 mmol) synthesized in Reference example 1 (1j) was dissolved in methanol (350 mL), and hydrochloric acid (4.8 mL) and 20% palladium hydroxide-carbon (2.8 g) were added thereto, followed by stirring of the mixture at room temperature under a hydrogen atmosphere for 4 hours. After the reaction mixture was filtered through Celite, 18% ammonia water (6 mL) was added thereto and the solvent was distilled off under reduced pressure. It was purified by an ion exchange resin (Dowex 50w×8) column (water-5% ammonia water). Further, it was purified using silica gel flash column chromatography (ethyl acetate:methanol:water, 2:2:1, V/V) to obtain the desired title compound (1.20 g, 63%) as a colorless solid.

$[α]_D^{20}$+145.7 (c 0.36, H$_2$O);

$^1$H NMR (400 MHz, D$_2$O): δ 1.28 (3H, d, J=6.6 Hz), 2.93 (1H, dd, J=12.4, 3.0 Hz), 3.12-3.20 (3H, m), 3.57-3.65 (4H, m), 3.71-3.87 (6H, m), 3.92-3.98 (2H, m), 4.32-4.34 (1H, m), 5.13 (1H, d, J=3.6 Hz), 5.34 (1H, d, J=3.0 Hz);

$^{13}$CNMR (125.70 MHz, D$_2$O): δ16.72, 51.62, 60.64, 61.62, 64.84, 68.79, 70.94, 71.07, 72.13, 72.83, 73.48, 74.96, 75.64, 77.13, 84.01, 97.44, 99.88;

MS (FAB) m/z: 442 (M+H)$^+$, 464 (M+Na)$^+$.

Reference Example 2

(2R,3R,4R)-4-Hydroxy-2-(hydroxymethyl)pyrrolidin-3-yl 4-O-(6-deoxy-β-D-glucopyranosyl)-α-D-glucopyranoside (2a) Allyl 4-O-β-D-glucopyranosyl-D-glucopyranoside α-D-cellobiose octaacetate (48.59 g, 71.6 mmol) was dissolved in methylene chloride (600 mL), and allyl alcohol (29 ml, 0.43 mol) and trimethylsilyl trifluoromethanesulfonate (16 mL, 86.0 mmol) were added thereto under ice-cooling, followed by stirring of the mixture at room temperature for 1.5 hours. Water (200 mL) was added to the reaction mixture and the mixture was extracted with methylene chloride (200 mL). The extract was washed with a saturated aqueous NaCl solution (100 mL) and after it was dried with anhydrous sodium sulfate, the solvent was distilled off under reduced pressure. The residue was dissolved in methanol (300 mL) and sodium methoxide (28 mL, 0.14 mol) was added thereto under ice-cooling, followed by stirring of the mixture at room temperature for 2 hours. Dowex 50w×8 was added to the reaction mixture until the reaction mixture became neutral and after it was filtered, the solvent was distilled off under reduced pressure. The residue was purified using silica gel flash column chromatography (ethyl acetate:methanol:water, 8:2:1, V/V) to obtain the desired title compound (24.8 g, yield: 91%) as a pale yellow amorphous substance.

$^1$H NMR (400 MHz, CDCl$_3$): δ 3.20-3.40 (9H, m), 3.40-3.65 (4H, m), 4.00-4.40 (3H, m), 5.18 (1H, d, J=11.7 Hz), 5.35 (1H, d, J=17.6 Hz), 5.95 (1H, ddd, J=17.6, 11.7, 5.9 Hz);

MS (FAB) m/z: 383 (M+H)$^+$.

(2b) Allyl 2,3,6-tri-O-benzyl-4-O-(2,3-di-O-benzyl-4,6-O-benzylidene-β-D-glucopyranosyl)-D-glucopyranoside The compound (24.8 g, 64.9 mmol) synthesized in Reference example 2 (2a) was dissolved in N,N-dimethylformamide (300 mL) and benzaldehyde dimethylacetal (13 mL, 84.4 mmol) and p-toluenesulfonic acid mono-hydrate (617 mg, 3.24 mmol) were added thereto, followed by stirring of the mixture at 50° C. at 20 mmHg for 5 hours. After triethylamine (900 μL) was added to the reaction mixture, the solvent was distilled off under reduced pressure. Water (100 mL) was added to the residue and the mixture was extracted with ethyl acetate (200 mL×5). The extract was washed with a saturated aqueous NaCl solution (100 mL) and after it was dried with anhydrous sodium sulfate, the solvent was distilled off under reduced pressure. The residue was dissolved in N,N-dimethylformamide (400 mL) and sodium hydride (20 g, 0.45 mmol) was added thereto under ice-cooling, followed by stirring of the mixture at the same temperature for 10 minutes. Benzyl bromide (54 mL, 0.45 mmol) was added to the reaction mixture and the mixture was stirred at room temperature for 2.5 hours. Water (100 mL) was added to the reaction mixture and the mixture was extracted with ethyl acetate (500 mL). The extract was washed with water (100 mL) and a saturated aqueous NaCl solution (50 mL) and after it was dried with anhydrous sodium sulfate, the solvent was distilled off under reduced pressure. The residue was purified using silica gel flash column chromatography (hexane:ethyl acetate, 10:1-7:1, V/V) to obtain the desired title compound (46.6 g, yield: 78%) as a pale yellow solid.

$^1$H NMR (400 MHz, CDCl$_3$): δ 3.10-5.00 (26H, m), 5.18 (1H, d, J=11.7 Hz), 5.35 (1H, d, J=17.6 Hz), 5.60 (1H, s), 5.95 (1H, ddd, J=17.6, 11.7, 5.9 Hz), 7.20-7.60 (30H, m);

MS (FAB) m/z: 922 (M+H)$^+$.

(2c) Allyl 2,3,6-tri-O-benzyl-4-O-(2,3,4-tri-O-benzyl-β-D-glucopyranosyl)-D-glucopyranoside The compound (63.0 g, 68.4 mmol) synthesized in Reference example 2 (2b) was dissolved in diethyl ether (800 mL) and methylene chloride (400 mL) and lithium aluminum hydride (10.4 g, 0.27 mol) and aluminum chloride (III) (36.4 g, 0.27 mol) were added thereto, followed by heating under reflux of the mixture for 1 hour. After the reaction mixture was diluted with diethyl ether (500 mL), 1N aqueous sodium hydroxide solution (21.0 mL) was added to the reaction mixture and the mixture was stirred for 1 hour. After the reaction mixture was extracted with ethyl acetate, the organic layer was washed with 10% aqueous hydrochloric acid solution (500 mL), a saturated aqueous sodium hydrogencarbonate solution (500 mL) and a saturated aqueous NaCl solution (300 mL). After it was dried with anhydrous sodium sulfate, the solvent was distilled off under reduced pressure. The residue was purified using silica gel flash column chromatography (hexane:ethyl acetate, 4:1-3:1-2:1, V/V) to obtain the desired title compound (37.8 g, yield: 60%) as a pale yellow solid.

$^1$H NMR (400 MHz, CDCl$_3$): δ 3.10-5.00 (29H, m), 5.18 (1H, d, J=10.8 Hz), 5.35 (1H, d, J=22.5 Hz), 5.95 (1H, ddd, J=22.5, 10.8, 5.9 Hz), 7.20-7.60 (30H, m);

MS (FAB) m/z: 924 (M+H)$^+$.

(2d) Allyl 2,3,6-tri-O-benzyl-4-O-(2,3,4-tri-O-benzyl-6-toluenesulfonyl-β-D-glucopyranosyl)-D-glucopyranoside The compound (37.8 g, 41.0 mmol) synthesized in Reference example 2 (2c) was dissolved in pyridine (300 mL), and p-toluenesulfonyl chloride (15.6 g, 82.0 mmol) and 4-dimethylaminopyridine (1.0 g, 0.82 mmol) were added thereto, followed by stirring of the mixture at room temperature for 13 hours. After the solvent was distilled off under reduced pressure, the residue was poured into 10% aqueous hydrochloric acid solution (50 mL) and ethyl acetate (200 mL), and the organic layer was washed with 10% aqueous hydrochloric acid solution (50 mL), a saturated aqueous sodium hydrogencarbonate solution (20 mL) and a saturated aqueous NaCl solution (20 mL). After it was dried with anhydrous sodium sulfate, the solvent was distilled off under reduced pressure. The residue was purified using silica gel flash column chromatography (hexane:ethyl acetate, 5:1-3:1, V/V) to obtain the desired title compound (32.6 g, yield: 74%) as a yellow oil.

$^1$H NMR (400 MHz, CDCl$_3$): δ 2.35 (3H, s), 3.10-5.00 (28H, m), 5.18 (1H, d, J=10.8 Hz), 5.35 (1H, d, J=22.5 Hz), 5.95 (1H, ddd, J=22.5, 10.8, 5.9 Hz), 7.10-7.65 (34H, m);

MS (FAB) m/z: 1078 (M+H)$^+$.

(2e) Allyl 2,3,6-tri-O-benzyl-4-O-(2,3,4-tri-O-benzyl-6-deoxy-β-D-glucopyranosyl)-D-glucopyranoside The compound (32.6 g, 30.3 mmol) synthesized in Reference example 2 (2d) was dissolved in diethyl ether (600 mL) and lithium aluminum hydride (1.72 g, 45.4 mol) was added thereto, followed by heating under reflux of the mixture for 1 hour. After the reaction mixture was diluted with diethyl ether (200 mL), 1N aqueous NaOH solution (2.0 mL) and water (2.0 mL) were added and the mixture was stirred for 30 minutes. After it was filtered through Celite, the solvent was distilled off under reduced pressure. The residue was purified using silica gel flash column chromatography (hexane:ethyl acetate, 7:1-6:1, V/V) to obtain the desired title compound (15.0 g, yield: 55%) as a colorless solid.

$^1$H NMR (400 MHz, CDCl$_3$): δ 1.20 (3H, d, J=6.0 Hz), 3.10-5.00 (26H, m), 5.20 (1H, d, J=10.8 Hz), 5.35 (1H, d, J=22.5 Hz), 5.95 (1H, ddd, J=22.5, 10.8, 5.9 Hz), 7.10-7.65 (30H, m);

MS (FAB) m/z: 908 (M+H)$^+$.

(2f) 2,3,6-tri-O-Benzyl-4-O-(2,3,4-tri-O-benzyl-6-deoxy-β-D-glucopyranosyl)-D-glucopyranoside The compound (15.0 g, 16.5 mmol) synthesized in Reference example 2 (2e) was dissolved in methanol (150 mL) and tetrahydrofuran (30 mL) and palladium chloride (II) (586 mg, 3.31 mmol) was added thereto, followed by stirring of the mixture at room temperature for 14 hours. After the reaction mixture was filtered through Celite, the solvent was distilled off under reduced pressure. The residue was purified using silica gel flash column chromatography (hexane:ethyl acetate, 5:1-4:1-3:1, V/V) to obtain the desired title compound (12.0 g, yield: 84%) as a pale yellow amorphous substance.

$^1$H NMR (400 MHz, CDCl$_3$): δ 1.19-1.22 (3H, m), 2.96-3.66 (8H, m), 3.77-4.02 (3H, m), 4.34-4.37 (2H, m), 4.54-4.89 (10H, m), 5.00-5.19 (2H, m), 7.23-7.45 (30H, m); MS (FAB) m/z: 868 (M+H)$^+$.

(2g) Benzyl (2R,3R,4R)-4-benzyloxy-2-benzyloxymethyl-3-{[2,3,6-tri-O-benzyl-4-O-(2,3,4-tri-O-benzyl-6-deoxy-β-D-glucopyranosyl)-α-D-glucopyranosyl]oxy}pyrrolidine-1-carboxylate The compound (18.8 g, 21.8 mmol) synthesized in Reference example 2 (2f) was dissolved in methylene chloride (400 mL) and trichloroacetonitrile (10.9 mL, 109 mmol) and 1,8-diazabicyclo[5.4.0]-7-undecene (0.33 mL, 2.18 mmol) were added thereto, followed by stirring of the mixture at room temperature for 15 minutes. After the solvent was distilled off under reduced pressure, it was purified using silica gel flash column chromatography (hexane:ethyl acetate, 5:1, 1% triethylamine, V/V) to obtain colorless oily imdate (19.8 g, 90%). The compound (9.5 g, 21.2 mmol) synthesized in Reference example 1 (1i) was dissolved in diethyl ether (480 mL) and a solution of trimethylsilyl trifluoromethanesulfonate (0.38 mL, 2.12 mmol) dissolved in diethyl ether (20 mL) was added thereto. A solution of imidate in diethyl ether (100 mL) was added to the reaction mixture and the mixture was stirred at room temperature for 3 hours. Triethylamine (0.35 mL, 2.54 mmol) was added to the reaction mixture and after the solvent was distilled off under reduced pressure, it was diluted with ethyl acetate (200 mL) and the mixture was washed with a saturated aqueous sodium hydrogencarbonate solution (200 mL) and a saturated aqueous NaCl solution (200 mL). After the organic layer was dried with anhydrous sodium sulfate, the solvent was distilled off under reduced pressure. The residue was purified using silica gel flash column chromatography (hexane:diethyl ether, 3:1, V/V) to obtain the desired title compound (13.3 g, 47%) and its β isomer (4.5 g, 16%) as a colorless oil.

$^1$H NMR (400 MHz, CDCl$_3$): δ 1.20 (3H, d, J=5.9 Hz), 3.10-3.22 (2H, m), 3.30-3.38 (2H, m), 3.42 (1H, t, J=8.8 Hz), 3.50-3.70 (5H, m), 3.76-3.87 (5H, m), 4.01-4.10 (1H, m), 4.26-4.51 (9H, m), 4.61 (1H, d, J=11.0 Hz), 4.69-4.88 (8H, m), 4.96-5.16 (3H, m), 7.19-7.34 (43H, m), 7.43 (2H, d, J=7.3 Hz);

MS (FAB) m/z: 1318 (M+Na)$^+$.

(2h) (2R,3R,4R)-4-Hydroxy-2-(hydroxymethyl)pyrrolidin-3-yl 4-O-(6-deoxy-β-D-glucopyranosyl)-α-D-glucopyranoside The compound (13.3 g, 10.3 mmol) synthesized in Reference example 2 (2g) was dissolved in 1% hydrochloric acid methanol solution (250 mL) and 20% palladium hydroxide-carbon (4 g) was added thereto, followed by stirring of the mixture under a hydrogen atmosphere for 2 hours. After the catalyst was removed by Celite filtration, 28% ammonia water (5 mL) was added thereto and the mixture was stirred for 10 minutes. The solvent was distilled off under reduced pressure and after it was passed through an ion exchange resin (Dowex 50w×8) column with water (200 mL), 1% ammonia water (200 mL) was passed through. The ammonia water containing the desired compound was concentrated under reduced pressure and it was purified using silica gel flash column chromatography (ethyl acetate:methanol:water, 5:2:1-1:1:1, V/V) to obtain the desired title compound (1.6 g, 35%) as a colorless solid.

$[α]_D^{20}$+88.8 (c 0.52, H$_2$O);
$^1$H NMR (500 MHz, D$_2$O): δ 1.22 (3H, d, J=6.8 Hz), 2.88 (1H, m), 3.07-3.16 (3H, m), 3.21 (1H, dd, J=7.8, 7.8 Hz), 3.36 (1H, dd, J=9.8, 9.8 Hz), 3.42 (1H, m), 3.49-3.55 (2H, m), 3.61-3.72 (5H, m), 3.75-3.83 (2H, m), 3.89 (1H, m), 4.24 (1H, m), 4.38 (1H, d J=7.9 Hz), 5.02 (1H, d, J=3.9 Hz);
$^{13}$C NMR (D$_2$O): δ 16.9, 51.7, 60.0, 61.8, 64.7, 71.0, 71.1, 71.6, 72.2, 73.6, 75.0, 75.5, 75.9, 79.2, 84.3, 97.4, 102.7;
MS (FAB) m/z: 442 (M+H)$^+$.

Reference Example 3

(2R,3R,4R)-4-Hydroxy-2-(hydroxymethyl)pyrrolidin-3-yl 4-O-β-D-glucopyranosyl-α-D-glucopyranoside (3a) Allyl 2,3,6-tri-O-benzyl-4-O-(2,3,4,6-tetra-O-benzyl-β-D-glucopyranosyl)-D-glucopyranoside α-D-Cellobiose octaacetate (4.15 g, 6.12 mmol) was dissolved in methylene chloride (50 mL) and allyl alcohol (2.09 mL, 30.6 mmol) and trimethylsilyl trifluoromethanesulfonate (1.11 mL, 6.12 mmol) were added thereto under ice-cooling, followed by stirring of the mixture at room temperature for 4 hours. Water (20 mL) was added to the reaction mixture and after the mixture was extracted with methylene chloride (50 mL), the organic layer was washed with a saturated aqueous NaCl solution (20 mL). After it was dried with anhydrous sodium sulfate, the solvent was distilled off under reduced pressure. The residue was dissolved in methanol (40 mL) and sodium methoxide (2.36 mL, 12.2 mmol) was added thereto, followed by stirring of the mixture at room temperature for 1 hour. Dowex 50w×8 was added to the reaction mixture until the reaction mixture became neutral and after it was filtered, the solvent was distilled off under reduced pressure. The residue was dissolved in N,N-dimethylformamide (60 mL) and sodium hydride (2.67 g, 61.2 mmol) was added thereto under ice-cooling, followed by stirring of the mixture at the same temperature for 10 minutes. Benzyl bromide (8.01 mL, 67.3 mmol) was added to the reaction mixture and the mixture was stirred at room temperature for 2 hours. Water (40 mL) was added to the reaction mixture and after the mixture was extracted with ethyl acetate (200 mL), the organic layer was washed with water (40 mL) and a saturated aqueous NaCl solution (20 mL). After it was dried with anhydrous sodium sulfate, the solvent was distilled off under reduced pressure. The residue was purified using silica gel flash column chromatography (hexane:ethyl acetate, 20:1-10:1-8:1, V/V) to obtain the desired title compound (4.85 g, yield: 78%) as a pale yellow solid.

$^1$H NMR (400 MHz, CDCl$_3$): δ 3.29-3.71 (10H, m), 3.80-4.15 (3H, m), 4.36-4.61 (8H, m), 4.67-4.89 (8H, m), 5.04-5.11 (1H, m), 5.17-5.22 (1H, m), 5.29-5.34 (1H, m), 5.91-5.98 (1H, m), 7.07-7.41 (35H, m);

MS (FAB) m/z: 1014 (M+H)$^+$.

(3b) 2,3,6-tri-O-Benzyl-4-O-(2,3,4,6-tetra-O-benzyl-β-D-glucopyranosyl)-D-glucopyranoside The compound (4.85 g, 4.79 mmol) synthesized in Reference example 3 (3a) was dissolved in dimethyl sulfoxide (40 mL) and potassium t-butoxide (2.15 g, 19.2 mmol) was added thereto, followed by stirring of the mixture at 110° C. for 1 hour. Water (30 mL) was added to the reaction mixture and after the mixture was extracted with ethyl acetate (150 mL), the organic layer was washed with a saturated aqueous NaCl solution (20 mL). After it was dried with anhydrous sodium sulfate, the solvent was distilled off under reduced pressure. The residue was dissolved in 1,4-dioxane (36 mL) and 16% aqueous sulfuric acid solution (3 mL) was added thereto, followed by stirring of the mixture at 100° C. for 1 hour. Water (30 mL) was added to the reaction mixture and after the mixture was extracted with ethyl acetate (150 mL), the organic layer was washed with a saturated aqueous NaCl solution (20 mL). After it was dried with anhydrous sodium sulfate, the solvent was distilled off under reduced pressure. The residue was purified using silica gel flash column chromatography (hexane:ethyl acetate, 4:1-3:1, V/V) to obtain the desired title compound (3.15 g, yield: 68%) as a brown oil.

$^1$H NMR (400 MHz, CDCl$_3$): δ 2.96-3.95 (9H, m), 4.30-4.38 (3H, m), 4.45-4.81 (7H, m), 4.98-5.10 (1H, m), 7.09-7.32 (35H, m);

MS (FAB) m/z: 974 (M+H)$^+$.

(3c) (2R,3R,4R)-4-Benzyloxy-N-benzyloxycarbonyl-2-benzyloxymethylpyrrolidin-3-yl 2,3,6-tri-O-benzyl-4-O-(2,3,4,6-tetra-O-benzyl-β-D-glucopyranosyl)-α-D-glucopyranoside The compound (537 mg, 0.55 mmol) synthesized in Reference example 3 (3b) was dissolved in methylene chloride (15 mL), and trichloroacetonitrile (277 μL, 2.76 mmol) and 1,8-diazabicyclo[5.4.0]-7-undecene (2 drops) were added thereto, followed by stirring of the mixture at room temperature for 40 minutes. After the solvent was distilled off under reduced pressure, it was purified using silica gel flash column chromatography (hexane:ethyl acetate, 5:1, 1% triethylamine, V/V) to obtain imidate (611 mg, 99%) as a yellow oil. The compound (223 mg, 0.50 mmol) synthesized in Reference example 1 (1i) was dissolved in diethyl ether (10 mL) and trimethylsilyl trifluoromethanesulfonate (9 μL, 0.05 mmol) was added thereto. A solution of the imidate (611 mg, 0.55 mmol) in diethyl ether (4 mL) was added dropwise thereto and the mixture was stirred at room temperature for 45 minutes. After triethylamine (4 drops) was added to the reaction mixture, the solvent was distilled off under reduced pressure. The residue was purified using silica gel flash column chromatography (hexane:diethyl ether, 2:1, V/V) to obtain the desired title compound (395 mg, 57%) as a pale yellow oil.

$^1$H NMR (400 MHz, CDCl$_3$): δ 3.24-3.86 (17H, m), 4.00-4.10 (2H, m), 4.25-4.54 (11H, m), 4.66-4.87 (8H, m), 4.95-5.12 (3H, m), 7.12-7.39 (50H, m);

MS (FAB) m/z: 1402 (M+H)$^+$.

(3d) (2R,3R,4R)-4-Hydroxy-2-hydroxymethylpyrrolidin-3-yl 4-O-β-D-glucopyranosyl-α-D-glucopyranoside The compound (611 mg, 0.55 mmol) synthesized in Reference example 3 (3c) was dissolved in methanol (8 mL) and ethyl acetate (2 mL), and hydrochloric acid-methanol solution (2 mL) and 20% palladium hydroxide-carbon (400 mg) were added thereto, followed by stirring of the mixture at room temperature under a hydrogen atmosphere for 4 hours. After the reaction mixture was filtered through Celite, the solvent was distilled off under reduced pressure and methanol (2 mL) and 28% ammonia water (300 μL) were added thereto, followed by stirring of the mixture at room temperature for 10 minutes. After the solvent was distilled off under reduced pressure, it was purified by an ion exchange resin (Dowex 50w×8) column (water-1.4% ammonia water). Further, it was purified using silica gel flash column chromatography (ethyl acetate:methanol:water, 1:1:1, V/V) to obtain the desired title compound (54 mg, 42%) as a colorless amorphous substance.

[α]$_D^{20}$ +91.9 (c 0.38, D$_2$O);

$^1$H NMR (400 MHz, D$_2$O): δ 2.90 (1H, dd, J=12.5, 2.2 Hz), 3.11 (1H, dd, J=12.5, 5.1 Hz), 3.16-3.22 (2H, m), 3.28-3.43 (3H, m), 3.49-3.82 (10H, m), 3.88-3.91 (1H, m), 4.23-4.27 (1H, m), 4.40 (1H, d, J=8.1 Hz), 5.01 (1H, d, J=4.4 Hz);

MS (FAB) m/z: 458 (M+H)$^+$.

Reference Example 4

(2R,3R,4R)-4-Hydroxy-2-hydroxymethylpyrrolidin-3-yl 4-O-(6-fluoro-6-deoxy-β-D-glucopyranosyl)-α-D-glucopyranoside (4a) Allyl 2,3,6-tri-O-benzyl-4-O-(2,3,4-tri-O-benzyl-6-fluoro-6-deoxy-β-D-glucopyranosyl)-α-D-glucopyranoside The compound (6.43 g, 6.97 mmol) synthesized in Reference example 2 (2c) was dissolved in 1,2-diethoxyethane (130 mL) and diethylaminosulfur trifluoride (2 mL, 20.50 mmol) was added thereto, followed by stirring of the mixture at 60° C. for 1 hour. Methanol (10 mL) was added to the reaction mixture under ice-cooling and the mixture was stirred for 30 minutes. Ethyl acetate (50 mL) was added to the reaction mixture and the organic layer was washed with a saturated aqueous sodium hydrogencarbonate solution (50 mL) and a saturated aqueous NaCl solution (50 mL). After it was dried with anhydrous sodium sulfate, the solvent was distilled off under reduced pressure. The residue was purified using silica gel flash column chromatography (hexane:ethyl acetate, 6:1, V/V) to obtain the desired title compound (5.06 g, yield: 78%) as a yellow solid.

$^1$H NMR (400 MHz, CDCl$_3$): δ 3.00-5.20 (28H, m), 5.25 (1H, d, J=8.0 Hz), 5.40 (1H, d, J=16.0 Hz), 6.00 (1H, m), 7.20-7.60 (30H, m);

MS (FAB) m/z: 926 (M+H)$^+$.

(4b) Allyl 2,3,6-tri-O-benzyl-4-O-(2,3,4-tri-O-benzyl-6-fluoro-6-deoxy-β-D-glucopyranosyl)-D-glucopyranoside The compound (5.06 g, 5.47 mmol) synthesized in Reference example 4 (4a) was dissolved in methanol (75 mL) and tetrahydrofuran (15 mL) and palladium chloride (II) (190 mg, 1.09 mmol) was added thereto, followed by stirring of the mixture at room temperature for 14 hours. After the reaction mixture was filtered through Celite, the solvent was distilled off under reduced pressure. The residue was purified using silica gel flash column chromatography (hexane:ethyl acetate, 4:1-3:1-2:1, V/V) to obtain the desired title compound (3.07 g, yield: 63%) as a pale yellow amorphous substance.

$^1$H NMR (400 MHz, CDCl$_3$): δ 3.10-5.20 (27H, m), 7.20-7.60 (30H, m);

MS (FAB) m/z: 886 (M+H)$^+$.

(4c) (2R,3R,4R)-4-Benzyloxy-N-benzyloxycarbonyl-2-(benzyloxymethyl)pyrrolidin-3-yl 2,3,6-tri-O-benzyl-4-O-(2,3,4-tri-O-benzyl-6-fluoro-6-deoxy-β-D-glucopyranosyl)-α-D-glucopyranoside The compound (646.0 mg, 0.73 mmol) synthesized in Reference example 4 (4b) was dissolved in methylene chloride (12 mL), and trichloroacetonitrile (0.38 mL, 3.66 mmol) and 1,8-diazabicyclo[5.4.0]unde-7-cene (1 drop) were added thereto, followed by stirring of the mixture at room temperature for 30 minutes. After the solvent was distilled off under reduced pressure, the residue was purified using silica gel flash column chromatography (hexane:ethyl acetate, 4:1, 1% triethylamine, V/V) to obtain yellow oily imidate (740.2 mg, 98.5%). The compound (326.7 mg, 0.73 mmol) synthesized in Reference example 1 (1i) was dissolved in diethyl ether (13 mL) and a solution of trimethylsilyl trifluoromethanesulfonate (6.6 μL, 0.037 mmol) dissolved in diethyl ether (2 mL) was added thereto under a nitrogen atmosphere. A solution of the imidate (740.2 mg) in diethyl ether (5 mL) was added to the reaction mixture and the mixture was stirred at room temperature for 2 hours. Triethylamine (5.0 μL, 0.036 mmol) was added to the reaction mixture and after the solvent was distilled off under reduced pressure, it was diluted with ethyl acetate (20 mL) and washed with a saturated aqueous sodium hydrogencarbonate solution (20 mL) and a saturated aqueous NaCl solution (20 mL). After the organic layer was dried with anhydrous sodium sulfate, the solvent was distilled off under reduced pressure and the residue containing the α, β mixture was purified using silica gel flash column chromatography (hexane:ethyl acetate, 6:1, V/V) to isolate the desired title compound α form (126.0 mg, 13%) as a colorless oil.

49

$^1$H NMR (400 MHz, CDCl$_3$): δ 3.00-5.20 (39H, m), 7.00-7.60 (45H, m);
MS (FAB) m/z: 1315 (M+H)$^+$.

(4d) (2R,3R,4R)-4-Hydroxy-2-hydroxymethylpyrrolidin-3-yl 4-O-(6-fluoro-6-deoxy-β-D-glucopyranosyl)-α-D-glucopyranoside The compound (126.0 mg, 0.096 mmol) synthesized in Reference example 4 (4c) was dissolved in methanol (10 mL) containing 1% aqueous hydrochloric acid solution and 20% palladium hydroxide-carbon (100 mg) was added thereto, followed by stirring of the mixture under a hydrogen atmosphere for 2 hours. After the catalyst was removed by Celite filtration, 28% ammonia water (0.5 mL) was added thereto and the mixture was stirred for 10 minutes. The solvent was distilled off under reduced pressure and after that an aqueous solution (100 mL) thereof was applied to an ion exchange resin (Dowex 50w×8) column, and 1% ammonia water (100 mL) was passed through. The ammonia water containing the desired compound was concentrated under reduced pressure and it was purified using silica gel flash column chromatography (ethyl acetate:methanol:water, 5:2:1-1:1:1, V/V) to obtain the desired title compound (23.1 mg, 52%) as a colorless amorphous substance.

$[α]_D^{20}$+49.6 (c 0.30, H$_2$O);
$^1$H NMR (400 MHz, D$_2$O): δ 3.00-3.07 (1H, m), 3.20-3.27 (2H, m), 3.30-3.80 (21H, m), 3.95 (1H, s), 4.29 (1H, brs), 4.43 (1H, d, J=8.0 Hz), 4.50-4.80 (2H, m), 5.00 (1H, d, J=4.0 Hz);
MS (FAB) m/z: 460 (M+H)$^+$.

Reference Example 5

(2R,3R,4R)-4-Hydroxy-2-hydroxymethylpyrrolidin-3-yl 4-O-(6-fluoro-6-deoxy-β-D-glucopyranosyl)-6-fluoro-6-deoxy-α-D-glucopyranoside (5a) Allyl 6-O-t-butyldimethylsilyl-2,3-di-O-benzyl-4-O-(6-O-t-butyldimethylsilyl-2,3,4-tri-O-benzyl-β-D-glucopyranosyl)-D-glucopyranoside The compound (7.76 g, 20.30 mmol) synthesized in Reference example 2 (2a) was dissolved in N,N-dimethylformamide (160 mL), and t-butyldimethylsilyl chloride (7.65 mL, 50.75 mmol) and imidazole (4.15 g, 60.90 mmol) were added thereto, followed by stirring of the mixture at room temperature for 1 hour. Water (50 mL) was added to the reaction mixture and after the mixture was extracted with ethyl acetate (100 mL), it was washed with a saturated aqeous NaCl solution (50 mL). After it was dried with anhydrous sodium sulfate, the solvent was distilled off under reduced pressure. The residue was dissolved in N,N-dimethylformamide (120 mL) and sodium hydride (4.0 g, 91.67 mmol) was added thereto under ice-cooling, followed by stirring of the mixture at the same temperature for 10 minutes. Benzyl bromide (11 mL, 92.48 mmol) was added to the reaction mixture and the mixture was stirred at room temperature for 3 hours. Water (50 mL) was added to the reaction mixture and after the mixture was extracted with ethyl acetate (150 mL), the organic layer was washed with water (50 mL) and a saturated aqueous NaCl solution (50 mL). After it was dried with anhydrous sodium sulfate, the solvent was distilled off under reduced pressure. The residue was purified using silica gel flash column chromatography (hexane:ethyl acetate, 12:1, V/V) to obtain the desired title compound (8.67 g, yield: 89%) as a colorless oily substance.

50

$^1$H NMR (400 MHz, CDCl$_3$): δ 0.00-0.20 (12H, m), 0.90-1.00 (18H, m), 3.00-5.20 (26H, m), 5.20 (1H, d, J=8.0 Hz), 5.35 (1H, d, J=16.0 Hz), 6.00 (1H, m), 7.20-7.60 (25H, m);
MS (FAB) m/z: 1062 (M+H)$^+$.

(5b) Allyl 2,3-di-O-benzyl-4-O-(2,3,4-tri-O-benzyl-β-D-glucopyranosyl)-D-glucopyranoside The compound (8.67 g, 8.17 mmol) synthesized in Reference example 5 (5a) was dissolved in tetrahydrofuran (150 mL) and 1.0M tetrabutylammonium fluoride THF solution (20 mL, 20 mmol) was added thereto, followed by stirring of the mixture at room temperature for 5 hours. After the solvent was distilled off under reduced pressure, the residue was purified using silica gel flash column chromatography (methylene chloride:methanol, 50:1, V/V) to obtain the desired title compound (4.19 g, yield: 62%) as a colorless oily substance.

$^1$H NMR (400 MHz, CDCl$_3$): δ 3.00-5.20 (28H, m), 5.20 (1H, d, J=12.0 Hz), 5.30 (1H, d, J=18.0 Hz), 5.98 (1H, m), 7.20-7.40 (25H, m);
MS (FAB) m/z: 833 (M+H)$^+$.

(5c) Allyl 2,3-di-O-benzyl-6-fluoro-6-deoxy-4-O-(2,3,4-tri-O-benzyl-6-fluoro-6-deoxy-β-D-glucopyranosyl)-D-glucopyranoside The compound (4.19 g, 5.03 mmol) synthesized in Reference example 5 (5b) was dissolved in 1,2-dimethoxyethane (85 mL) and diethylaminosulfur trifluoride (2.5 mL, 25.61 mmol) was added thereto, followed by stirring of the mixture at 60° C. for 1 hour. Methanol (10 mL) was added to the reaction mixture under ice-cooling and the mixture was stirred for 30 minutes. Ethyl acetate (50 mL) was added thereto and the organic layer was washed with a saturated aqueous sodium hydrogencarbonate solution (50 mL) and a saturated aqueous NaCl solution (50 mL). After it was dried with anhydrous sodium sulfate, the solvent was distilled off under reduced pressure. The residue was purified using silica gel flash column chromatography (hexane:ethyl acetate, 5:1-4:1, V/V) to obtain the desired title compound (2.23 g, yield: 53%) as a yellow solid.

$^1$H NMR (400 MHz, CDCl$_3$): δ 3.00-5.10 (26H, m), 5.23 (1H, m), 5.33 (1H, m), 5.95 (1H, m), 7.20-7.40 (25H, m);
MS (FAB) m/z: 837 (M+H)$^+$.

(5d) Allyl 2,3-di-O-benzyl-6-fluoro-6-deoxy-4-O-(2,3,4-tri-O-benzyl-6-fluoro-6-deoxy-β-D-glucopyranosyl)-D-glucopyranoside The compound (2.23 g, 2.66 mmol) synthesized in Reference example 5 (5c) was dissolved in acetic acid (20 mL) and water (1 mL), and palladium chloride (II) (0.47 g, 2.65 mmol) and sodium acetate (0.87 g, 10.61 mmol) were added thereto, followed by stirring of the mixture at room temperature for 14 hours. After the reaction mixture was filtered through Celite, the solvent was distilled off under reduced pressure. The residue was purified using silica gel flash column chromatography (hexane:ethyl acetate, 3:1, V/V) to obtain the desired title compound (0.73 g, yield: 34%) as a pale yellow amorphous substance.

$^1$H NMR (400 MHz, CDCl$_3$): δ 3.00-5.10 (25H, m), 7.20-7.60 (25H, m);
MS (FAB) m/z: 797 (M+H)$^+$.

(5e) (2R,3R,4R)-4-Benzyloxy-N-benzyloxycarbonyl-2-(benzyloxymethyl)pyrrolidin-3-yl 2,3-di-O-benzyl-6-fluoro-6-deoxy-4-O-(2,3,4-tri-O-benzyl-6-fluoro-6-deoxy-β-D-glucopyranosyl)-α-D-glucopyranoside The compound (730.0 mg, 0.92 mmol) synthesized in Reference example 5 (5d) was dissolved in methylene chloride (13.5 mL) and trichloroacetonitrile (0.46 mL, 4.60 mmol) and 1,8-diazabicyclo[5.4.0]-7-undecene (1 drop) were added thereto, followed by stirring of the mixture at room temperature for 30 minutes. After the solvent was distilled off under reduced pressure, the residue was purified using silica gel flash column chromatography (hexane:ethyl acetate, 4:1, 1% triethylamine, V/V) to obtain yellow oily imidate (675.3 mg, 78%). The compound (412.3 mg, 0.92 mmol) synthesized in Reference example 1 (1i) was dissolved in diethyl ether (13 mL) and a solution of trimethylsilyl trifluoromethanesulfonate (8.3 µL, 0.046 mmol) dissolved in diethyl ether (2 mL) was added thereto under a nitrogen atmosphere. Subsequently, a solution of the imidate (675.3 mg) in diethyl ether (5 mL) was added to the reaction mixture and the mixture was stirred at room temperature for 2 hours. Triethylamine (7.0 µL, 0.050 mmol) was added to the reaction mixture and after the solvent was distilled off under reduced pressure, it was diluted with ethyl acetate (20 mL) and washed with a saturated aqueous sodium hydrogencarbonate solution (20 mL) and a saturated aqueous NaCl solution (20 mL). After the organic layer was dried with anhydrous sodium sulfate, the solvent was distilled off under reduced pressure. The residue containing the α, β mixture was purified using silica gel flash column chromatography (hexane:ethyl acetate, 6:1, V/V) to isolate the desired title compound α form (122.6 mg, 11%) as a colorless oil.

$^1$H NMR (400 MHz, CDCl$_3$): δ 3.00-5.20 (37H, m), 7.00-7.60 (40H, m);

MS (FAB) m/z: 1227 (M+H)$^+$.

(5f) (2R,3R,4R)-4-Hydroxy-2-hydroxymethylpyrrolidin-3-yl 4-O-(6-fluoro-6-deoxy-β-D-glucopyranosyl)-6-fluoro-6-deoxy-α-D-glucopyranoside The compound (122.6 mg, 0.10 mmol) synthesized in Reference example 5 (5e) was dissolved in methanol (10 mL) containing 1% aqueous hydrochloric acid solution and 20% palladium hydroxide-carbon (100 mg) was added thereto, followed by stirring of the mixture under a hydrogen atmosphere for 2 hours. After the catalyst was removed by Celite filtration, 28% ammonia water (0.5 mL) was added thereto and the mixture was stirred for 10 minutes. The solvent was distilled off under reduced pressure and after an aqueous solution thereof (100 mL) was applied to an ion exchange resin (Dowex 50w×8) column, it was made to flow using 1% ammonia water (100 mL). The ammonia water containing the desired compound was concentrated under reduced pressure, it was purified using silica gel flash column chromatography (ethyl acetate:methanol:water, 5:2:1-1:1:1, V/V) to obtain the desired title compound (25.9 mg, 56%) as a colorless solid.

$^1$H NMR (400 MHz, D$_2$O): δ 3.20-3.90 (22H, m), 4.10 (1H, s), 4.41 (1H, d, J=8.1 Hz), 4.50-4.80 (4H, m), 5.05 (1H, d, J=6.3 Hz);

MS (FAB) m/z: 462 (M+H)$^+$.

Reference Example 6

(1S,3R,4R,5S)-1-Amino-3-hydroxy-5-hydroxymethylcyclopent-4-yl 4-O-(6-deoxy-β-D-glucopyranosyl)-α-D-glucopyranoside

(6a) Methyl 4,6-O-benzylidene-3-O-benzyl-2-deoxy-D-glucopyranoside

2-Deoxy-D-glucose (10.1 g, 61.5 mmol) was dissolved in methanol (100 mL) and hydrochloric acid-methanol solution (50 mL) was added thereto, followed by heating under reflux of the mixture for 3 hours. After the reaction mixture was cooled to room temperature, triethylamine was added to the reaction mixture until the reaction mixture became basic and the solvent was distilled off under reduced pressure. The residue was dissolved in N,N-dimethylformamide (100 mL), and benzaldehydedimethylacetal (12.9 mL, 86.1 mmol) and p-toluenesulfonic acid mono-hydrate (585 mg, 3.08 mmol) were added thereto, followed by stirring of the mixture at 20 mm Hg at 50° C. for 3 hours. After the reaction mixture was cooled to room temperature, water (50 mL) was added to the reaction mixture and after the mixture was extracted with ethyl acetate (200 mL), the organic layer was washed with water (50 mL) and a saturated aqueous NaCl solution (30 mL). After it was dried with anhydrous sodium sulfate, the solvent was distilled off under reduced pressure. The residue was dissolved in N,N-dimethylformamide (100 mL) and 55% sodium hydride (3.99 g, 92.3 mmol) was added thereto under ice-cooling, followed by stirring of the mixture at the same temperature for 10 minutes. Benzyl bromide (11.0 mL, 92.3 mmol) was added thereto and the mixture was stirred at room temperature for 19 hours. Water (50 mL) was added to the reaction mixture and after the mixture was extracted with ethyl acetate (200 mL), the organic layer was washed with water (50 mL) and a saturated aqueous NaCl solution (30 mL). After it was dried with anhydrous sodium sulfate, the solvent was distilled off under reduced pressure. The residue was purified using silica gel flash column chromatography (hexane:ethyl acetate, 20:1-10:1, V/V) to obtain the desired title compound (16.0 g, yield: 73%) as a yellow solid.

$^1$H NMR (400 MHz, CDCl$_3$): δ 1.66-1.83 (1H, m), 2.24-2.34 (1H, m), 3.33 (3H, s), 3.65-3.85 (3H, m), 3.98-4.04 (1H, m), 4.22-4.35 (1H, m), 4.66-4.84 (3H, m), 5.60-5.62 (1H, m), 7.23-7.40 (8H, m), 7.49-7.52 (2H, m);

MS (FAB) m/z: 357 (M+H)$^+$.

(6b) Methyl 3-O-benzyl-2-deoxy-D-glucopyranoside

The compound (2.00 g, 5.62 mmol) synthesized in Reference example 6 (6a) was dissolved in acetic acid (15 mL) and water (5 mL) and the mixture was stirred at 60° C. for 2 hours and 30 minutes. After the reaction mixture was cooled to room temperature, the solvent was distilled off under reduced pressure. The residue was purified using silica gel flash column chromatography (hexane:ethyl acetate, 2:1-1:2, V/V) to obtain the desired title compound (1.33 g, yield: 88%) as a pale yellow oil.

$^1$H NMR (400 MHz, CDCl$_3$): δ 1.49-1.64 (1H, m), 2.11 (1H, brs), 2.25-2.36 (1H, m), 2.62 (1H, brs), 3.33 (3H, s), 3.44-3.65 (2H, m), 3.76-3.87 (3H, m), 4.41-4.52 (1H, m), 4.65-4.71 (1H, m), 4.81-4.82 (1H, m), 7.26-7.37 (5H, m);

MS (FAB) m/z: 267 (M−H)$^+$.

(6c) Methyl 3-O-benzyl-2-deoxy-6-O-p-toluenesulfonyl-D-glucopyranoside

The compound (12.2 g, 45.3 mmol) synthesized in Reference example 6 (6b) was dissolved in pyridine (100 mL), and p-toluenesulfonyl chloride (13 g, 68.0 mmol) and 4-dimethylaminopyridine (553 mg, 4.53 mmol) were added thereto, followed by stirring of the mixture at room temperature for 12 hours. The reaction mixture was poured into 10% aqueous hydrochloric acid solution (80 mL) and ethyl acetate (200 mL) under ice-cooling and the organic layer was washed with 10% aqueous hydrochloric acid solution (80 mL), a saturated aqueous sodium hydrogencarbonate solution (80 mL) and a saturated aqueous NaCl solution (50 mL). After it was dried with anhydrous sodium sulfate, the solvent was distilled off under reduced pressure. The residue was purified using silica gel flash column chromatography (hexane:ethyl acetate, 5:1-3:1, V/V) to obtain the desired title compound (16.9 g, yield: 88%) as a pale yellow amorphous substance.

$^1$H NMR (400 MHz, CDCl$_3$): δ 1.54-1.61 (1H, m), 2.20-2.28 (1H, m), 2.44 (3H, s), 3.27 (3H, s), 3.41-3.48 (2H, m), 3.70-3.76 (2H, m), 4.22-4.41 (2H, m), 4.47-4.57 (1H, m), 4.63-4.68 (1H, m), 4.75-4.76 (1H, m), 7.26-7.36 (7H, m), 7.79-7.84 (2H, m);

MS (FAB) m/z: 421 (M−H)$^+$.

(6d) Methyl 4-O-benzoyl-3-O-benzyl-2-deoxy-6-O-p-toluenesulfonyl-D-glucopyranoside The compound (16.9 g, 40.0 mmol) synthesized in Reference example 6 (6c) was dissolved in methylene chloride (150 mL) and triethylamine (22 mL, 0.16 mol), benzoyl chloride (14 mL, 0.12 mol) and 4-dimethylaminopyridine (489 mg, 4.00 mmol) were added thereto, followed by stirring of the mixture at room temperature for 18 hours. Water (80 mL) was added to the reaction mixture and after the mixture was extracted with methylene chloride (100 mL). After the organic layer was washed with a saturated aqueous NaCl solution and dried with anhydrous sodium sulfate, the solvent was distilled off under reduced pressure. The residue was purified using silica gel flash column chromatography (hexane:ethyl acetate, 4:1-3:1, V/V) to obtain the desired title compound (20.8 g, yield: 99%) as a yellow oil.

$^1$H NMR (400 MHz, CDCl$_3$): δ 1.71-1.78 (1H, m), 2.26-2.31 (1H, m), 2.33 (3H, s), 3.32 (3H, s), 3.94-4.14 (4H, m), 4.40-4.44 (1H, m), 4.52-4.59 (1H, m), 4.80-4.81 (1H, m), 5.03-5.08 (1H, m), 7.09-7.20 (6H, m), 7.40-7.49 (3H, m), 7.57-7.62 (1H, m), 7.66-7.71 (2H, m), 7.87-7.96 (2H, m);

MS (FAB) m/z: 527 (M+H)$^+$.

(6e) Methyl 4-O-benzoyl-3-O-benzyl-2,6-dideoxy-6-iodo-D-glucopyranoside

The compound (2.53 g, 4.81 mmol) synthesized in Reference example 6 (6d) was dissolved in toluene (30 mL) and sodium iodide (3.6 g, 24.0 mmol) and 18-crown-6-ether (254 mg, 0.96 mmol) were added thereto, followed by stirring of the mixture at 100° C. under a nitrogen atmosphere for 3 hours. After the reaction mixture was cooled to room temperature, water (30 mL) was added to the reaction mixture and after the mixture was extracted with ethyl acetate (100 mL), the organic layer was washed with a saturated aqueous NaCl solution (30 mL). After it was dried with anhydrous sodium sulfate, the solvent was distilled off under reduced pressure. The residue was purified using silica gel flash column chromatography (hexane:ethyl acetate, 15:1-10:1, V/V) to obtain the desired title compound (2.11 g, yield: 91%) as a pale yellow oil.

$^1$H NMR (400 MHz, CDCl$_3$): δ 1.72-1.86 (1H, m), 2.31-2.41 (1H, m), 3.17-3.26 (1H, m), 3.33-3.40 (1H, m), 3.45 (3H, s), 3.69-3.86 (1H, m), 3.99-4.31 (1H, m), 4.44-4.48 (1H, m), 4.57-4.62 (1H, m), 4.90-4.91 (1H, m), 5.03-5.18 (1H, m), 7.13-7.26 (5H, m), 7.43-7.49 (2H, m), 7.58-7.62 (1H, m), 8.02-8.04 (2H, m);

MS (FAB) m/z: 483 (M+H)$^+$.

(6f) 4-O-Benzoyl-3-O-benzyl-2,5,6-trideoxy-D-xylo-hexa-5-enose oxime

The compound (2.11 g, 4.38 mmol) synthesized in Reference example 6 (6e) was dissolved in isopropanol (50 mL) and water (2 mL) and zinc powder (2 g) washed with 5% aqueous hydrochloric acid solution was added thereto, followed by heating under reflux of the mixture for 25 minutes. After the reaction mixture was cooled to room temperature, it was filtered through Celite and the solvent was distilled off under reduced pressure. The residue was dissolved in ethanol (50 mL) and hydroxylamine hydrochloride (913 mg, 13.1 mmol) and pyridine (1.06 mL, 13.1 mmol) were added thereto, followed by stirring of the mixture at 60° C. for 50 minutes. After the reaction mixture was cooled to room temperature, the solvent was distilled off under reduced pressure. Water (20 mL) was added thereto and after the mixture was extracted with ethyl acetate (100 mL), the organic layer was washed with a saturated aqueous NaCl solution (20 mL). After it was dried with anhydrous sodium sulfate, the solvent was distilled off under reduced pressure. The residue was purified using silica gel flash column chromatography (hexane:ethyl acetate, 6:1-5:1-4:1-3:1, V/V) to obtain the desired title compound (1.14 g, yield: 77%) as a colorless oil.

$^1$H NMR (400 MHz, CDCl$_3$): δ 2.47-2.55 (1H, m), 2.61-2.79 (1H, m), 3.88 (0.5H, dt, J=8.1, 5.1 Hz), 3.94 (0.5H, dt, J=8.1, 4.4 Hz), 4.65 (0.5H, d, J=11.7 Hz), 4.67 (0.5H, d, J=11.7 Hz), 4.74 (0.5H, d, J=11.7 Hz), 4.75 (0.5H, d, J=11.7 Hz), 5.33-5.36 (1H, m), 5.41-5.47 (1H, m), 5.74-5.77 (1H, m), 6.01 (1H, ddd, J=16.8, 5.9, 5.1 Hz), 6.84 (0.5H, t, J=5.1 Hz), 7.26-7.33 (5H, m), 7.43-7.48 (2.5H, m), 7.56-7.60 (1H, m), 8.06-8.08 (2H, m);

MS (FAB) m/z: 340 (M+H)$^+$.

(6g) (3aR,4R,5R,6aS)-4-Benzoyloxy-5-benzyloxy-hexahydro-cyclopenta[c]isooxazole (3aS,4R,5R,6aR)-4-Benzoyloxy-5-benzyloxy-hexahydro-cyclopenta[c]isooxazole The compound (5.0 g, 14.7 mmol) synthesized in Reference example 6 (6f) was dissolved in toluene (100 mL) and the mixture was heated under reflux for 40 hours. After the mixture was cooled to room temperature, the solvent was distilled off under reduced pressure and the residue was purified using silica gel flash column chromatography (hexane:ethyl acetate, 2:1-1:1, V/V) to obtain the desired title compound (mixture) (4.08 g, yield: 82%) as an orange oil.

$^1$H NMR (400 MHz, CDCl$_3$): δ 1.92 (0.3H, ddd, J=10.2, 5.1, 5.1 Hz), 2.00-2.13 (1.4H, m), 2.28-2.35 (0.3H, m), 2.99-3.01 (0.3H, m), 3.37 (0.7H, dd, J=8.8, 7.3 Hz), 3.43-3.49 (0.7H, m), 3.99-4.22 (4.3H, m), 4.63 (0.3H, d, J=11.7 Hz), 4.63 (1.4H, s), 4.67 (0.3H, d, J=9.5 Hz), 5.21 (0.3H, t, J=3.7 Hz), 5.28 (0.7H, d, J=3.7 Hz), 7.25-7.35 (5H, m), 7.43-7.47 (2H, m), 7.54-7.60 (1H, m), 7.99-8.08 (2H, m);

MS (FAB) m/z: 340 (M+H)$^+$.

(6h) (3aR,4R,5R,6aS)-5-Benzyloxy-1-benzyloxycarbonyl-4-hydroxy-hexahydro-cyclopenta[c]isooxazole The compound (4.08 g, 12.0 mmol) synthesized in Reference example 6 (6g) was dissolved in methanol (40 mL) and sodium methoxide (696 μL, 3.61 mmol) was added thereto, followed by stirring of the mixture at room temperature for 2 hours. Dowex 50w×8 was added to the reaction mixture until the reaction mixture became neutral and after it was filtered, the solvent was distilled off under reduced pressure. The residue was dissolved in ethyl acetate (40 mL), and a saturated aqueous sodium hydrogencarbonate solution (20 mL) and benzyloxychloroformate (2.4 mL, 16.8 mmol) were added thereto under ice-cooling, followed by stirring of the mixture at the same temperature for 1 hour and 30 minutes. The organic layer was washed with a saturated aqueous NaCl solution (50 mL) and after it was dried with anhydrous sodium sulfate, the solvent was distilled off under reduced pressure. The residue was purified using silica gel flash column chromatography (hexane:ethyl acetate, 2:1-1:1, V/V) to obtain the desired title compound (789 mg, yield: 18%) as a pale yellow solid and its diastereomer (1.62 g, yield: 36%) as a pale yellow oil.

$^1$H NMR (400 MHz, CDCl$_3$): δ 1.57-1.63 (1H, m), 2.47 (1H, brs), 2.50-2.56 (1H, m) 2.73-2.77 (1H, m), 3.61-3.69 (2H, m), 3.88-3.92 (1H, m), 4.01 (1H, d, J=8.8 Hz), 4.49 (1H, d, J=11.7 Hz), 4.48-4.55 (1H, m), 4.60 (1H, d, J=11.7 Hz), 5.18 (2H, s);

MS (FAB) m/z: 370 (M+H)$^+$.

(6i) (3aR,4R,5R,6aS)-5-Benzyloxy-1-benzyloxycarbonyl-hexahydro-cyclopenta[c]isooxazol-4-yl 2,3,6-tri-O-benzyl-4-O-(2,3,4-tri-O-benzyl-6-deoxy-β-D-glucopyranosyl)-D-glucopyranoside The compound (751 mg, 0.87 mmol) synthesized in Reference example 2 (2f) was dissolved in methylene chloride (15 mL), and trichloroacetonitrile (435 μL, 4.33 mmol) and 1,8-diazabicyclo[5.4.0]-7-undecene (2 drops) were added thereto, followed by stirring of the mixture at room temperature for 1 hour. After the solvent was distilled off under reduced pressure, the residue was purified using silica gel flash column chromatography (hexane:ethyl acetate, 6:1-5:1, 1% triethylamine, V/V) to obtain imidate (734 mg, 84%) as a yellow oil. The compound (244 mg, 0.66 mmol) synthesized in Reference example 6 (6 h) was dissolved in diethyl ether (12 mL) and trimethylsilyl trifluoromethanesulfonate (12 μL, 0.07 mmol) was added thereto. A solution of the imidate (734 mg, 0.73 mmol) in diethyl ether (3 mL) was added dropwise to the mixture and the mixture was stirred at room temperature for 1 hour. After triethylamine (4 drops) was added to the reaction mixture, the solvent was distilled off under reduced pressure. The residue was purified using silica gel flash column chromatography (hexane:diethyl ether, 2:1-1:1, V/V) to obtain the desired title compound (α,β mixture) (516 mg, yield: 64%) as a colorless amorphous substance.

$^1$H NMR (400 MHz, CDCl$_3$): δ 1.19 (1.5H, d, J=2.9 Hz), 1.20 (1.5H, d, J=2.9 Hz), 1.62-1.68 (0.5H, m), 1.79-1.84 (0.5H, m), 2.39-2.45 (0.5H, m), 2.48-2.53 (0.5H, m), 2.73-2.77 (0.5H, m), 2.85-2.86 (0.5H, m), 3.10-3.60 (8H, m), 3.69-4.02 (6H, m), 4.10-4.14 (1H, m), 4.32-4.64 (8H, m), 4.69-4.87 (7H, m), 5.00 (0.5H, d, J=10.7 Hz), 5.12 (0.5H, d, J=3.9 Hz), 5.18 (1H, d, J=10.7 Hz), 7.18-7.43 (50H, m);

MS (FAB) m/z: 1217 (M)$^+$.

(6j) (3aR,4R,5R,6aS)-5-Benzyloxy-1-methyloxycarbonyl-hexahydro-cyclopenta[c]isooxazol-4-yl 2,3,6-tri-O-benzyl-4-O-(2,3,4-tri-O-benzyl-6-deoxy-β-D-glucopyranosyl)-α-D-glucopyranoside The compound (516 mg, 0.42 mmol) synthesized in Reference example 6 (6i) was dissolved in methanol (6 mL) and toluene (6 mL) and sodium methoxide (221 μL, 1.15 mmol) was added thereto, followed by stirring of the mixture at 50° C. for 40 minutes. After the reaction mixture was cooled to room temperature, Dowex 50W×8 was added to the reaction mixture until the reaction mixture became neutral. After it was filtered, the solvent was distilled off under reduced pressure. The residue was purified using silica gel flash column chromatography (hexane:diethyl ether, 1.5:1-1:1, V/V) to obtain the desired title compound (173 mg, yield: 47%) as a colorless amorphous substance.

$^1$H NMR (400 MHz, CDCl$_3$): δ 1.61-1.69 (1H, m), 2.48-2.55 (1H, m), 2.72-2.78 (1H, m), 3.13 (1H, dd, J=9.5, 8.8 Hz), 3.21 (1H, dd, J=9.5, 5.9 Hz), 3.31 (1H, dd, J=8.1, 7.3 Hz), 3.36-3.54 (5H, m), 3.59-3.62 (1H, m), 3.79 (3H, s), 3.74-3.94 (5H, m), 3.99 (1H, d, J=8.8 Hz), 4.32-4.38 (2H, m), 4.50-4.67 (7H, m), 4.76-5.00 (5H, m), 5.01 (1H, d, J=11.0 Hz), 5.12 (1H, d, J=3.7 Hz), 7.14-7.44 (35H, m);

MS (FAB) m/z: 1141 (M)$^+$.

(6k) (3aR,4R,5R,6aS)-5-Benzyloxy-hexahydro-cyclopenta[c]isooxazol-4-yl 2,3,6-tri-O-benzyl-4-O-(2,3,4-tri-O-benzyl-6-deoxy-β-D-glucopyranosyl)-α-D-glucopyranoside The compound (363 mg, 0.32 mmol) synthesized in Reference example 6 (6j) was dissolved in methanol (8 mL) and 1N aqueous potassium hydroxide solution (4 mL) was added thereto, followed by stirring of the mixture at 80° C. for 8 hours. After the reaction mixture was cooled to room temperature, a saturated aqueous sodium ammonium chloride solution (15 mL) was added to the reaction mixture. After the mixture was extracted with ethyl acetate (100 mL), the organic layer was washed with a saturated aqueous NaCl solution (10 mL). After it was dried with anhydrous sodium sulfate, the solvent was distilled off under reduced pressure. The residue was purified using silica gel flash column chromatography (hexane:ethyl acetate, 1.5:1-1:1, V/V) to obtain the desired title compound (313 mg, yield: 91%) as a pale yellow amorphous substance.

$^1$H NMR (400 MHz, CDCl$_3$): δ 1.20 (3H, d, J=5.9 Hz), 1.56-1.64 (1H, m), 2.26-2.36 (1H, m), 2.76-2.86 (1H, m), 3.13 (1H, dd, J=9.5, 8.8 Hz), 3.19-3.25 (2H, m), 3.32 (1H, dd, J=8.8, 8.1 Hz), 3.43-3.53 (3H, m), 3.67-3.69 (2H, m), 3.81-3.95 (6H, m), 4.35-4.40 (2H, m), 4.51-4.67 (7H, m), 4.74-4.87 (6H, m), 5.01 (1H, d, J=10.3 Hz), 7.15-7.44 (35H, m);

MS (FAB) m/z: 1084 (M+H)$^+$.

(6l) (1S,3R,4R,5S)-1-Amino-3-hydroxy-5-hydroxymethylcyclopent-4-yl 4-O-(6-deoxy-β-D-glucopyranosyl)-α-D-glucopyranoside The compound (313 mg, 0.29 mmol) synthesized in Reference example 6 (6k) was dissolved in methanol (8 mL) and ethyl acetate (4 mL), and hydrochloric acid (5 drops) and 20% palladium hydroxide-carbon (300 mg) were added thereto, followed by stirring of the mixture at room temperature under a hydrogen atmosphere for 6 hours. After the reaction mixture was filtered through Celite, the solvent was distilled off under reduced pressure. Methanol (3 mL) and 28% ammonia water (300 μL) were added to the residue and the mixture was stirred at room temperature for 10 minutes. After the solvent was distilled off under reduced pressure, the residue was purified by an ion exchange resin column (Dowex 50W×8) (water-2.8% ammonia water). Further, it was purified using silica gel flash column chromatography (ethyl acetate:methanol:water, 1:1:1, V/V) to obtain the desired title compound (107 mg, yield: 81%) as a pale yellow solid.

¹H NMR (500 MHz, D₂O): δ 1.19 (1H, d, J=5.9 Hz), 1.53 (1H, dt, J=13.7, 6.8 Hz), 2.18-2.23 (1H, m), 2.27-2.33 (1H, m), 3.07 (1H, dd, J=9.8, 8.8 Hz), 3.19 (1H, dd, J=9.8, 7.8 Hz), 3.34 (1H, dd, J=9.8, 8.8 Hz), 3.37-3.41 (1H, m), 3.47-3.51 (2H, m), 3.58 (1H, dd, J=14.7, 6.8 Hz), 3.66-3.80 (6H, m), 3.86 (1H, dd, J=6.8, 4.9 Hz), 4.11-4.14 (1H, m), 4.36 (1H, d, J=7.8 Hz), 5.06 (1H, d, J=3.9 Hz);
¹³C NMR (125 MHz, D₂O): δ 16.89, 38.27, 47.74, 49.85, 59.41, 60.05, 70.97, 71.19, 71.56, 72.22, 73.64, 74.96, 75.45, 75.51, 79.24, 84.26, 97.34, 102.68;
MS (FAB) m/z: 456 (M+H)⁺.

Reference Example 7

(2R,3R,4R,5R)-2,5-Dihydroxymethyl-4-hydroxypyr-rolidin-3-yl 4-O-(6-deoxy-β-D-glucopyranosyl)-α-D-glucopyranoside (7a) (1R,3S,4S,6R,7R)-7-Benzyloxy-6-hydroxymethyl-3-methoxy-2-oxa-5-aza-bicyclo[2.2.1]heptane Azide epoxide (Tetrahedron, 26, 1985, 1469) (2.03 g, 6.97 mmol) was dissolved in ethanol (40 mL) and Lindler catalyst (0.4 g) was added thereto, followed by stirring of the mixture under a hydrogen atmosphere for 2 hours. After the catalyst was removed by Celite filtration, it was dissolved in ethanol (40 mL) and the mixture was heated under reflux for 1 hour. After the solvent was distilled off under reduced pressure, the residue was purified using silica gel flash column chromatography (methylene chloride:ethanol, 20:1-10:1, V/V) to obtain the desired title compound (1.21 g, yield: 65%) as a brown solid.
¹H NMR (400 MHz, CDCl₃): δ 2.15-2.35 (2H, br), 3.19 (1H, dd, J=5.8, 5.9 Hz), 3.35 (3H, s), 3.41 (1H, s), 3.65 (1H, dd, J=5.8, 11.7 Hz), 3.73 (1H, dd, J=5.8, 11.7 Hz), 4.11 (1H, s), 4.18 (1H s), 4.54 (1H, d, J=11.7 Hz), 4.61 (1H, d, J=11.7 Hz), 4.64 (1H, s), 7.29-7.38 (5H, m);
MS (FAB) m/z: 266 (M+H)⁺.

(7b) (1R,3R,4S,6R,7R)-7-Hydroxy-6-hydroxymethyl-3-methoxy-2-oxa-5-aza-bicyclo[2.2.1]heptane-5-carboxylic acid benzyl ester The compound (930 mg, 3.51 mmol) synthesized in Reference example 7 (7a) was dissolved in methanol (20 mL) and 20% palladium hydroxide-carbon (280 mg) was added thereto, followed by stirring of the mixture under a hydrogen atmosphere for 6 hours. After the catalyst was removed by Celite filtration, the solvent was distilled off under reduced pressure. The residue was dissolved in ethyl acetate: a saturated aqueous sodium hydrogencarbonate solution (2:1, 20 mL) and benzyl chloroformate (0.75 mL, 5.27 mmol) was added thereto, followed by stirring of the mixture at 0° C. for 2 hours. Water (20 mL) was added to the reaction mixture at 0° C. and after the mixture was extracted with ethyl acetate, the organic layer was washed with a saturated aqueous NaCl solution (20 mL). After it was dried with anhydrous sodium sulfate, the solvent was distilled off under reduced pressure. The residue was purified using silica gel flash column chromatography (hexane:ethyl acetate, 1:1-3:1, V/V) to obtain the desired title compound (759 mg, yield: 70%) as a colorless solid.
¹H NMR (400 MHz, CDCl₃): δ 3.33 (3H, s), 3.50-4.00 (3H, m), 4.10-4.25 (3H, m), 4.61 (1H, brs), 4.60-4.74 (2H, m), 5.10-5.25 (2H, m), 7.25-7.45 (5H, m);
MS (FAB) m/z: 310 (M+H)⁺.

(7c) (1R,3S,4S,6R,7R)-7-Benzyloxy-6-t-butyldimethylsilyloxymethyl-3-methoxy-2-oxa-5-aza-bicyclo [2.2.1]heptane-5-carboxylic acid benzyl ester The compound (152 mg, 0.49 mmol) synthesized in Reference example 7 (7b) was dissolved in pyridine (4 mL) and t-butyldimethylsilyl chloride (82 mg, 0.54 mmol) was added thereto, followed by stirring of the mixture at 0° C. for 3 hours. After it was confirmed by TLC that the starting material had disappeared, benzoyl chloride (86 μL, 0.74 mmol) was added thereto and the mixture was stirred at 0° C. for 1 hour. Water (20 ml) was added to the reaction mixture at 0° C. and after the mixture was extracted with ethyl acetate, the organic layer was washed with a saturated aqueous NaCl solution (20 mL). After it was dried with anhydrous sodium sulfate, the solvent was distilled off under reduced pressure. The residue was purified using silica gel flash column chromatography (hexane:ethyl acetate, 10:1, V/V) to obtain the desired title compound (218 mg, yield: 84%) as a colorless oil.
¹H NMR (400 MHz, CDCl₃): δ 0.24-0.04 (6H, m), 0.72 (4.5H, s), 0.77 (4.5H, s), 3.34 (1.5H, s), 3.38 (1.5H, s), 3.67-3.80 (2H, m), 3.91 (0.5H m), 4.10 (0.5H, m), 4.40 (0.5H, s), 4.46 (0.5H, m), 4.66 (0.5H, s), 4.69 (1H, m), 4.78 (0.5H, m), 5.15 (2H, m), 5.44 (1H, m), 7.39-7.36 (5H, m), 7.41 (2H, m), 7.55 (1H, m), 7.95 (2H, m);
MS (FAB) m/z: 528 (M+H)⁺.

(7d) (2R,3R,4R,5R)—N-Benzyloxycarbonyl-3-benzoyl-2,5-dihydroxymethyl-4-hydroxypyrrolidine The compound (997 mg, 1.89 mmol) synthesized in Reference example 7 (7c) was dissolved in trifluoroacetic acid:water (4:1, 12 mL) and the mixture was stirred at room temperature for 15 minutes. Water (20 mL) was added to the reaction mixture at 0° C. and after the mixture was extracted with dichloromethane (30 mL), the organic layer was washed with a saturated aqueous sodium hydrogencarbonate solution (20 mL) and a saturated aqueous NaCl solution (20 mL). After it was dried with anhydrous sodium sulfate, the solvent was distilled off under reduced pressure. The residue was dissolved in ethanol (15 mL) and a reagent obtained by dissolving sodium borohydride (35.7 mg, 0.10 mmol) in water (5 mL) was added thereto, followed by stirring of the mixture at 0° C. for 20 minutes. After a saturated aqueous ammonium chloride solution (2 mL) was added to the reaction mixture at 0° C., ethanol was distilled off under reduced pressure. Water (15 mL) was added and after the mixture was extracted with ethyl acetate (15 mL), the organic layer was washed with a saturated aqueous NaCl solution (15 mL). After it was dried with anhydrous sodium sulfate, the solvent was distilled off under reduced pressure. The residue was purified using silica gel flash column chromatography (hexane:ethyl acetate, 2:1, V/V) to obtain the desired title compound (643 mg, yield: 85%) as a colorless oil.
¹H NMR (400 MHz, CDCl₃): δ 3.60-3.38 (9H, m), 4.98-5.19 (4H, m), 7.20-7.30 (5H, m), 7.36. (2H, m), 7.50 (1H, m), 7.89 (2H, d, J=7.3 Hz);
MS (FAB) m/z: 402 (M+H)⁺.

(7e) (2R,3R,4R,5R)—N-Benzyloxycarbonyl-3-hydroxy-2,5-dibenzyloxymethyl-4-benzyloxypyrrolidine The compound (643 mg, 1.60 mmol) synthesized in Reference example 7 (7d) was dissolved in dichloromethane:

cyclohexane (1:2, 18 mL), and benzyltrichloroacetimidate (2.7 mL, 14.4 mmol) and trifluoromethanesulfonic acid (29 μL, 0.32 mmol) were added thereto, followed by stirring of the mixture at room temperature for 2 hours. A saturated aqueous sodium hydrogencarbonate solution (5 mL) was added to the reaction mixture at 0° C. and after the mixture was diluted with ethyl acetate (200 mL), the mixture was washed with water (30 mL) and a saturated aqueous NaCl solution (30 mL). After it was dried with anhydrous sodium sulfate, the solvent was distilled off under reduced pressure. The residue was purified using silica gel flash column chromatography (hexane:ethyl acetate, 20:1-10:1, V/V) to obtain 1080 mg of a colorless oil. The thus obtained colorless oil (1080 mg) was dissolved in methanol:tetrahydrofuran (4:1, 25 mL) and potassium carbonate (44 mg, 0.32 mmol) was added thereto, followed by stirring of the mixture at room temperature for 2.5 hours. After methanol was distilled off under reduced pressure, water (15 mL) was added to the residue and after the mixture was extracted with ethyl acetate (15 mL), the organic layer was washed with a saturated aqueous NaCl solution (15 mL). After it was dried with anhydrous sodium sulfate, the solvent was distilled off under reduced pressure. The residue was purified using silica gel flash column chromatography (hexane:ethyl acetate, 4:1, V/V) to obtain the desired title compound (715 mg, yield: 78%) as a colorless oil.

$^1$H NMR (400 MHz, CDCl$_3$): δ 3.40-3.49 (2H, m), 3.62 (1H, dd, J=4.4, 8.8 Hz), 3.79-4.12 (4H, m), 4.19 (1H, dd, J=3.7, 10.3 Hz), 4.26-4.61 (6H, m), 5.01 (1H, d, J=16.8 Hz), 5.03 (1H, d, J=16.8 Hz), 5.51 (1H, m), 7.15-7.38 (20H, m);

MS (FAB) m/z: 568 (M+H)$^+$.

(7f) (2R,3R,4R,5R)—N-Benzyloxycarbonyl-2,5-dibenzyloxymethyl-4-benzyloxypyrrolidin-3-yl 2,3,6-tri-O-benzyl-4-O-(2,3,4-tri-O-benzyl-6-deoxy-β-D-glucopyranosyl)-α-D-glucopyranoside The compound (426 mg, 0.49 mmol) synthesized in Reference example 2 (2f) was dissolved in methylene chloride (8 mL), and trichloroacetonitrile (0.25 mL, 2.45 mmol) and 1,8-diazabicyclo[5.4.0]-7-undecene (7 μL, 0.05 mmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain colorless oily imidate (398 mg, 80%). The compound (248 mg, 0.44 mmol) synthesized in Reference example 7 (7e) was dissolved in diethyl ether (8 mL) and trimethylsilyl trifluoromethanesulfonate (7 μL, 44 μmol) was added thereto under a nitrogen atmosphere. A solution of the imidate in diethyl ether (5 mL) was added to the reaction mixture and the mixture was stirred at room temperature for 1.5 hours. Triethylamine (12 μL, 88 μmol) was added to the reaction mixture and after the solvent was distilled off under reduced pressure, it was diluted with ethyl acetate (20 mL) and the mixture was washed with a saturated aqueous sodium hydrogencarbonate solution (20 mL) and a saturated aqueous NaCl solution (20 mL). After the organic layer was dried with anhydrous sodium sulfate, the solvent was distilled off under reduced pressure. The residue was purified using silica gel flash column chromatography (hexane:diethyl ether, 4:1, V/V) to obtain the desired title compound (218 mg, 31%) as a colorless oil.

$^1$H NMR (500 MHz, CDCl$_3$): δ 1.23 (3H, d, J=5.9 Hz), 2.92-3.19 (4H, m), 3.26-3.73 (13H, m), 3.85 (1H, dd, J=5.1, 5.1 Hz), 3.93 (1H, dd, J=5.1, 5.1 Hz), 4.31 (1H, d, J=8.0 Hz), 5.03 (1H, d, J=3.6 Hz);

MS (FAB) m/z: 472 (M+H)$^+$.

(7g) (2R,3R,4R,5R)-2,5-dihydroxymethyl-4-hydroxypyrrolidin-3-yl 4-O-(6-deoxy-β-D-glucopyranosyl)-α-D-glucopyranoside The compound (218 mg, 0.15 mmol) synthesized in Reference example 7 (7f) was dissolved in a 1% hydrochloric acid-methanol solution (5 mL) and 20% palladium hydroxide-carbon (110 mg) was added thereto, followed by stirring of the mixture under a hydrogen atmosphere for 2 hours. After the catalyst was removed by Celite filtration, 28% ammonia water (0.8 mL) was added thereto and the mixture was stirred for 10 minutes. The solvent was distilled off under reduced pressure and the residue was passed through an ion exchange resin column with water (30 mL), 1% ammonia water (30 mL) was made to flow. The ammonia water containing the desired compound was concentrated under reduced pressure and was purified using silica gel flash column chromatography (ethyl acetate:methanol:water, 5:2:1-1:1:1, V/V) to obtain the desired title compound (47 mg, 64%) as a colorless solid.

$^1$H NMR (400 MHz, D$_2$O): δ 1.15 (3H, d, J=5.9 Hz), 2.92-3.19 (4H, m), 3.26-3.73 (13H, m), 3.85 (1H, dd, J=5.1, 5.1 Hz), 3.93 (1H, dd, J=5.1, 5.1 Hz), 4.31 (1H, d, J=8.0 Hz), 5.03 (1H, d, J=3.6 Hz);

MS (FAB) m/z: 472 (M+H)$^+$.

Reference Example 8

(2R,3R,4R)-4-Hydroxy-2-hydroxymethylpyrrolidin-3-yl 4-O-(6-methoxy-6-deoxy-β-D-glucopyranosyl)-D-glucopyranoside (8a) Allyl 2,3,6-tri-O-benzyl-4-O-(2,3,4-tri-O-benzyl-6-fluoro-6-deoxy-β-D-glucopyranosyl)-α-D-glucopyranoside The compound (2.19 g, 2.37 mmol) synthesized in Reference example 2 (2c) was dissolved in N,N-dimethylformamide (45 mL) and sodium hydride (0.12 g, 2.75 mmol) was added thereto under ice-cooling, followed by stirring of the mixture for 10 minutes. Methyl iodide (0.3 mL, 4.82 mmol) was added to the reaction mixture and the mixture was stirred at room temperature for 5 hours. Methanol (5 mL) was added to the reaction mixture under ice-cooling and the mixture was stirred for 30 minutes. Ethyl acetate (20 mL) was added to the reaction mixture and the organic layer was washed with water (20 mL) and a saturated aqueous NaCl solution (20 mL). After it was dried with anhydrous sodium sulfate, the solvent was distilled off under reduced pressure. The residue was purified using silica gel flash column chromatography (hexane:ethyl acetate, 6:1-5:1, V/V) to obtain the desired title compound (1.80 g, yield: 81%) as a colorless oil.

$^1$H NMR (400 MHz, CDCl$_3$): δ 3.21 (3H, s), 3.30-5.00 (28H, m), 5.10 (1H, m), 5.20 (1H, m), 5.95 (1H, m), 7.20-7.40 (30H, m);

MS (FAB) m/z: 938 (M+H)$^+$.

(8b) Allyl 2,3,6-tri-O-benzyl-4-O-(2,3,4-tri-O-benzyl-6-methoxy-6-deoxy-β-D-glucopyranosyl)-D-glucopyranoside The compound (1.80 g, 1.92 mmol) synthesized in Reference example 8 (8a) was dissolved in methanol (30 mL) and tetrahydrofuran (6 mL), and palladium chloride (II) (67.4 mg, 0.38 mmol) was added thereto, followed by stirring of the mixture at room temperature for 14 hours. After the reaction mixture was filtered through Celite, the solvent was distilled off under reduced pressure. The residue was purified using silica gel flash column chromatography (hexane:ethyl acetate, 5:1-4:1-3:1, V/V) to obtain the desired title compound (1.43 g, yield: 83%) as a colorless amorphous substance.

$^1$H NMR (400 MHz, CDCl$_3$): δ 3.20 (3H, s), 3.25-5.00 (27H, m), 5.10 (1H, m), 7.20-7.40 (30H, m);

MS (FAB) m/z: 898 (M+H)$^+$.

(8c) (2R,3R,4R)-4-Benzyloxy-N-benzyloxycarbonyl-2-(benzyloxymethyl)pyrrolidin-3-yl 2,3,6-tri-O-benzyl-4-O-(2,3,4-tri-O-benzyl-6-methoxy-6-deoxy-β-D-glucopyranosyl)-α-D-glucopyranoside The compound (762.6 mg, 0.85 mmol) synthesized in Reference example 8 (8b) was dissolved in methylene chloride (14 mL), and trichloroacetonitrile (0.43 mL, 4.29 mmol) and 1,8-diazabicyclo[5.4.0]unde-7-cene (1 drop) were added thereto, followed by stirring of the mixture at room temperature for 30 minutes. After the solvent was distilled off under reduced pressure, the residue was purified using silica gel flash column chromatography (hexane:ethyl acetate, 4:1, 1% triethylamine, V/V) to obtain colorless oily imidate (567.8 mg, 64%). The compound (380.8 mg, 0.85 mmol) synthesized in Reference example 1 (1i) was dissolved in diethyl ether (13 mL) and a solution of trimethylsilyl trifluoromethanesulfonate (8.0 μL, 0.044 mmol) dissolved in diethyl ether (2 mL) was added thereto under a nitrogen atmosphere. A solution of the imidate (567.8 mg) in diethyl ether (5 mL) was added to the reaction mixture and the mixture was stirred at room temperature for 2 hours. Triethylamine (8.0 μL, 0.057 mmol) was added to the reaction mixture and after the solvent was distilled off under reduced pressure, it was diluted with ethyl acetate (20 mL) and the mixture was washed with a saturated aqueous sodium hydrogencarbonate solution (20 mL) and a saturated aqueous NaCl solution (20 mL). After the organic layer was dried with anhydrous sodium sulfate, the solvent was distilled off under reduced pressure. The residue containing the mixture of α and β isomers was purified using silica gel flash column chromatography (hexane:diethyl ether, 3:1, V/V) to isolate the desired title compound α form (150.1 mg, 13%) as a colorless amorphous substance.

$^1$H NMR (400 MHz, CDCl$_3$): δ 3.20 (3H, s), 3.25-5.20 (39H, m), 7.20-7.40 (45H, m); MS (FAB) m/z: 1327 (M+H)$^+$.

(8d) (2R,3R,4R)-4-Hydroxy-2-hydroxymethylpyrrolidin-3-yl 4-O-(6-methoxy-6-deoxy-β-D-glucopyranosyl)-α-D-glucopyranoside The compound (150.1 mg, 0.11 mmol) synthesized in Reference example 8 (8c) was dissolved in methanol (10 mL) containing 1% aqueous hydrochloric acid solution and 20% palladium hydroxide-carbon (100 mg) was added thereto, followed by stirring of the mixture under a hydrogen atmosphere for 2 hours. After the catalyst was removed by Celite filtration, 28% ammonia water (0.5 mL) was added thereto and the mixture was stirred for 10 minutes. The solvent was distilled off under reduced pressure and after an aqueous solution thereof (100 mL) was applied to an ion exchange resin (Dowex 50w×8) column, it was eluted with 1% ammonia water (100 mL). The ammonia water containing the desired compound was concentrated under reduced pressure and purified using silica gel flash column chromatography (ethyl acetate:methanol:water, 5:2:1-1:1:1, V/V) to obtain the desired title compound (49.1 mg, 95%) as a colorless solid.

$^1$H NMR (400 MHz, CDCl$_3$): δ 3.00-4.20 (19H, m), 3.27 (3H, s), 4.37 (1H, d, J=8.0 Hz), 4.98 (1H, d, J=3.7 Hz);

MS (FAB) m/z: 472 (M+H)$^+$.

Reference Example 9

(2R,3R,4R)-4-Fluoro-2-hydroxymethylpyrrolidin-3-yl 4-O-(6-deoxy-α-D-glucopyranosyl)-α-D-glucopyranoside (9a) (2R,3R,4R)-3-Benzoyloxy-N-benzyloxycarbonyl-2-benzyloxymethyl-4-hydroxy-pyrrolidine The compound (3.37 g, 9.07 mmol) synthesized in Reference example 1 (1 h) was dissolved in methylene chloride:cyclohexane (1:2, 180 mL), and benzyltrichloroacetimidate (2.0 mL, 10.88 mmol) and trifluoromethanesulfonic acid (2.57 ml, 15.3 mmol) were added thereto, followed by stirring of the mixture at room temperature for 1 hour. A saturated aqueous sodium hydrogencarbonate solution (20 mL) was added to the reaction mixture at 0° C. and after the mixture was diluted with ethyl acetate (200 mL), it was washed with water (300 mL) and a saturated aqueous sodium hydrogencarbonate solution (300 mL). After it was dried with anhydrous sodium sulfate, the solvent was distilled off under reduced pressure. The residue was purified using silica gel flash column chromatography (hexane:ethyl acetate, 5:1-2:1, V/V) to obtain 4.71 g of a pale yellow oil.

$^1$H NMR (400 MHz, CDCl$_3$): δ 3.50-4.20 (4H, m), 4.45-4.80 (3H, m), 5.00-5.60 (5H, m), 7.32-7.46 (12H, m), 7.59 (1H, m), 7.99 (2H, m);

MS (FAB) m/z: 462 (M+H)$^+$.

(9b) (2R,3R,4S)-3-Benzoyloxy-N-benzyloxycarbonyl-2-benzyloxymethyl-4-hydroxy-pyrrolidine The compound (183 mg, 0.40 mmol) synthesized in Reference example 9 (9a) was dissolved in methylene chloride (4 mL), and pyridine (96 μL, 1.20 mmol) and trifluoromethanesulfonic anhydride (0.10 mL, 0.60 mmol) were added thereto, followed by stirring of the mixture at 0° C. for 20 minutes. Water (10 mL) was added to the reaction mixture at 0° C. and after the mixture was extracted with methylene chloride, the organic layer was washed with a saturated aqueous NaCl solution (10 mL). After it was dried with anhydrous sodium sulfate, the solvent was distilled off under reduced pressure. The residue was purified using silica gel flash column chromatography (hexane:ethyl acetate, 2:1, V/V) to obtain the desired title compound (92 mg, yield: 50%) as a pale yellow oil.

$^1$H NMR (400 MHz, CDCl$_3$): δ 3.25-4.20 (4H, m), 4.25-4.75 (3H, m), 5.10-5.60 (5H, m), 7.32-7.46 (12H, m), 7.59 (1H, t, J=7.4 Hz), 7.99 (2H, d, J=8.8 Hz);

MS (FAB) m/z: 462 (M+H)$^+$.

(9c) (2R,3R,4R)—N-Benzoyloxycarbonyl-2-benzyloxymethyl-4-fluoropyrrolidine

The compound (980 mg, 2.12 mmol) synthesized in Reference example 9 (9b) was dissolved in 1,2-dimethoxyethane (20 mL) and diethylaminosulfur trifluoride (0.84 mL, 6.36 mmol) was added thereto at −20° C. The temperature of the mixture was gradually raised and the mixture was stirred at 60° C. for 1 hour. After a saturated aqueous sodium hydrogencarbonate solution was added to the reaction mixture at 0°

C. until foaming was not generated, the mixture was extracted with ethyl acetate and the organic layer was washed with a saturated aqueous NaCl solution (20 mL). After it was dried with anhydrous sodium sulfate, the solvent was distilled off under reduced pressure. The residue was purified using silica gel flash column chromatography (hexane:ethyl acetate, 4:1, V/V) to obtain a pale yellow oil (545 mg). The thus obtained pale yellow oil (545 mg) was dissolved in methanol (10 mL) and potassium carbonate (50 mg) was added thereto, followed by stirring of the mixture at room temperature for 20 minutes. After the solvent was distilled off under reduced pressure, water (20 mL) was added to the reaction mixture and after the mixture was extracted with ethyl acetate, the organic layer was washed with a saturated aqueous NaCl solution (20 mL). The solvent was distilled off under reduced pressure and the residue was purified using silica gel flash column chromatography (hexane:ethyl acetate, 2:1, V/V) to obtain the desired title compound (263 mg, yield: 34%) as a colorless oil.

$^1$H NMR (400 MHz, CDCl$_3$): δ 3.10-4.20 (4H, m), 4.25-4.75 (3H, m), 4.80-5.20 (5H, m), 7.30-7.45 (10H, m);

MS (FAB) m/z: 360 (M+H)$^+$.

(9d) (2R,3R,4R)—N-Benzyloxycarbonyl-2-benzyloxymethyl-4-fluoropyrrolidin-3-yl 2,3,6-tri-O-benzyl-4-O-(2,3,4-tri-O-benzyl-6-deoxy-α-D-glucopyranosyl)-α-D-glucopyranoside The compound (657 mg, 0.76 mmol) synthesized in Reference example 1 (1f) was dissolved in methylene chloride (12 mL), and trichloroacetonitrile (0.38 mL, 3.8 mmol) and 1,8-diazabicyclo[5.4.0]-7-undecene (11 µL, 76 µmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain colorless oily imidate (767 mg, 100%). The compound (263 mg, 0.73 mmol) synthesized in Reference example 9 (9c) was dissolved in diethyl ether (12 mL) and trimethylsilyl trifluoromethanesulfonate (13 µL, 73 µmol) was added thereto under a nitrogen atmosphere. A solution of imidate in diethyl ether (8 mL) was added to the reaction mixture and the mixture was stirred at room temperature for 1.5 hours. Triethylamine (20 µL, 146 µmol) was added to the reaction mixture and after the solvent was distilled off under reduced pressure, it was diluted with ethyl acetate (20 mL) and the mixture was washed with a saturated aqueous sodium hydrogencarbonate solution (20 mL) and a saturated aqueous NaCl solution (20 mL). After the organic layer was dried with anhydrous sodium sulfate, the solvent was distilled off under reduced pressure and the residue was purified using silica gel flash column chromatography (hexane:diethyl ether, 4:1, V/V) to obtain the desired title compound α form (109 mg, 12%) and β form (52 mg, 6%) as a colorless oil.

$^1$H NMR (400 MHz, CDCl$_3$): δ 1.09 (3H, d, J=4.2 Hz), 3.00-5.60 (35H, m), 7.10-7.40 (40H, m);

MS (FAB) m/z: 1209 (M+H)$^+$.

(9e) (2R,3R,4R)-4-Fluoro-2-hydroxymethylpyrrolidin-3-yl 4-O-(6-deoxy-α-D-glucopyranosyl)-α-D-glucopyranoside The compound (109 mg, 90.2 µmol) synthesized in Reference example 9 (9d) was dissolved in a 1% hydrochloric acid-methanol solution (5 mL) and 20% palladium hydroxide-carbon (55 mg) was added thereto, followed by stirring of the mixture under a hydrogen atmosphere for 1 hour. After the catalyst was removed by Celite filtration, 28% ammonia water (0.2 mL) was added thereto and the mixture was stirred for 10 minutes. The solvent was distilled off under reduced pressure and after the residue was passed through an ion exchange resin (Dowex 50w×8) column, 1% ammonia water (30 mL) was passed through. The ammonia water containing the desired compound was concentrated under reduced pressure and it was purified using silica gel flash column chromatography (ethyl acetate:methanol:water, 5:2:1-1:1:1, V/V) to obtain the desired title compound (26 mg, 65%) as a colorless solid.

$^1$H NMR (500 MHz, CDCl$_3$): δ 1.18 (3H, d, J=5.9 Hz), 2.98-3.16 (4H, m), 3.47-3.77 (12H, m), 4.11 (1H, dd, J=4.9, 20.5 Hz), 5.02 (1H, m), 5.23 (1H, m);

MS (FAB) m/z: 444 (M+H)$^+$.

Reference Example 10

(2R,3R,4R)-4-Hydroxy-2-fluoromethylpyrrolidin-3-yl 4-O-(6-deoxy-β-D-glucopyranosyl)-α-D-glucopyranoside

(10a) (2R,3R,4R)-3-Benzoyloxy-N-benzyloxycarbonyl-2-fluoromethyl-4-hydroxy-pyrrolidine The compound (257 mg, 0.69 mmol) synthesized in Reference example 1 (1h) was dissolved in 1,2-dimethoxyethane (5 mL) and diethylaminosulfur trifluoride (0.11 mL, 0.83 mmol) was added thereto at −20° C. The temperature of the mixture was gradually raised and the mixture was stirred at 60° C. for 1 hour. After a saturated aqueous sodium hydrogencarbonate solution was added to the reaction mixture at 0° C. until foaming was not generated, the mixture was extracted with ethyl acetate (15 mL) and the organic layer was washed with a saturated aqueous NaCl solution (15 mL). After it was dried with anhydrous sodium sulfate, the solvent was distilled off under reduced pressure. The residue was purified using silica gel flash column chromatography (hexane:ethyl acetate, 3:1, V/V) to obtain a colorless oil (113 mg, 44%).

$^1$H NMR (400 MHz, CDCl$_3$): δ 3.50-4.25 (4H, m), 4.50-5.55 (3H, m), 5.40-5.60 (2H, m), 7.20-7.50 (7H, m), 7.60 (1H, m), 8.00-8.10 (2H, m);

MS (FAB) m/z: 374 (M+H)$^+$.

(10b) (2R,3R,4S)-3-Benzoyloxy-N-benzyloxycarbonyl-4-benzyloxy-2-fluoromethyl-pyrrolidine The compound (344 mg, 0.92 mmol) synthesized in Reference example 10 (10a) was dissolved in methylene chloride:cyclohexane (1:2, 10 mL), and benzyltrichloroacetimidate (0.68 mL, 3.68 mmol) and trifluoromethanesulfonic acid (16 µL, 0.18 mmol) were added thereto, followed by stirring of the mixture at room temperature for 4 hours. A saturated aqueous sodium hydrogencarbonate solution (1 mL) was added to the reaction mixture at 0° C. and after the mixture was diluted with ethyl acetate (20 mL), the mixture was washed with water (20 mL) and a saturated aqueous NaCl solution (20 mL). After it was dried with anhydrous sodium sulfate, the solvent was distilled off under reduced pressure. The residue was purified using silica gel flash column chromatography (hexane:ethyl acetate, 8:1-5:1, V/V) to obtain a colorless oil (307 mg, 68%).

¹H NMR (400 MHz, CDCl₃): δ 3.50-5.25 (7H, m), 5.50-5.75 (4H, m), 7.20-7.50 (12H, m), 7.60 (1H, m), 8.00-8.10 (2H, m);
MS (FAB) m/z: 464 (M+H)⁺.

(10c) (2R,3R,4S)—N-Benzyloxycarbonyl-4-benzyloxy-2-fluoromethylpyrrolidine

The compound (307 mg, 0.66 mmol) synthesized in Reference example 10 (10b) was dissolved in methanol (6 mL) and potassium carbonate (27 mg, 0.20 mmol) was added thereto, followed by stirring of the mixture at room temperature for 2.5 hours. After methanol was distilled off under reduced pressure, water (15 mL) was added and the mixture was extracted with ethyl acetate (15 mL). The organic layer was washed with a saturated aqueous NaCl solution (15 mL). After it was dried with anhydrous sodium sulfate, the solvent was distilled off under reduced pressure. The residue was purified using silica gel flash column chromatography (hexane:ethyl acetate, 3:1, V/V) to obtain the desired title compound (176 mg, yield: 74%) as a colorless oil.
¹H NMR (400 MHz, CDCl₃): δ 3.35-4.80 (7H, m), 5.50-5.75 (4H, m), 7.20-7.50 (10H, m);
MS (FAB) m/z: 360 (M+H)⁺.

(10d) (2R,3R,4R)—N-Benzyloxycarbonyl-4-benzyloxy-2-fluoromethylpyrrolidin-3-yl 2,3,6-tri-O-benzyl-4-O-(2,3,4-tri-O-benzyl-6-deoxy-β-D-glucopyranosyl)-α-D-glucopyranoside The compound (398 mg, 0.46 mmol) synthesized in Reference example 2 (2f) was dissolved in methylene chloride (8 mL) and trichloroacetonitrile (0.23 mL, 2.30 mmol) and 1,8-diazabicyclo[5.4.0]-7-undecene (7 µL, 0.05 mmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain colorless oily imidate. The compound (165 mg, 0.46 mmol) synthesized in Reference example 10 (10c) was dissolved in diethyl ether (8 mL) and trimethylsilyl trifluoromethanesulfonate (8 µL, 46 µmol) was added thereto under a nitrogen atmosphere. A solution of the imidate in diethyl ether (4 mL) was added to the reaction mixture and the mixture was stirred at room temperature for 2.5 hours. Triethylamine (13 µL, 92 µmol) was added to the reaction mixture and after the solvent was distilled off under reduced pressure, it was diluted with ethyl acetate (15 mL) and the mixture was washed with a saturated aqueous sodium hydrogencarbonate solution (15 mL) and a saturated aqueous NaCl solution (15 mL). After the organic layer was dried with anhydrous sodium sulfate, the solvent was distilled off under reduced pressure and the residue was purified using silica gel flash column chromatography (hexane:diethyl ether, 4:1, V/V) to obtain the desired title compound (53 mg, 10%) as a colorless oil. ¹H NMR (400 MHz, CDCl₃): δ 1.10 (3H, d, J=4.2 Hz), 3.00-5.60 (35H, m), 7.10-7.40 (40H, m);
MS (FAB) m/z: 1209 (M+H)⁺.

(10e) (2R,3R,4R)-4-Hydroxy-2-fluoromethylpyrrolidin-3-yl 4-O-(6-deoxy-β-D-glucopyranosyl)-α-D-glucopyranoside The compound (53 mg, 43.9 µmol) synthesized in Reference example 10 (10d) was dissolved in a 1% hydrochloric acid-methanol solution (5 mL) and 20% palladium hydroxide-carbon (30 mg) was added thereto, followed by stirring of the mixture under a hydrogen atmosphere for 3 hours. After the catalyst was removed by Celite filtration, 28% ammonia water (0.2 mL) was added thereto and the mixture was stirred for 10 minutes. The solvent was distilled off under reduced pressure and after the residue was passed through an ion exchange resin column with water (30 mL), 1% ammonia water (30 mL) was passed through. The ammonia water containing the desired compound was concentrated under reduced pressure and it was purified using silica gel flash column chromatography (ethyl acetate:methanol:water, 5:2:1-1:1:1, V/V) to obtain the desired title compound (1.6 mg, 8%) as a colorless solid.
¹H NMR (500 MHz, CDCl₃): δ 1.18 (3H, d, J=4.0 Hz), 2.98-4.25 (16H, m), 4.50 (2H, m), 5.83 (1H, m);
MS (FAB) m/z: 444 (M+H)⁺.

Reference Example 11

(2R,3R,4S)-4-Hydroxy-2-hydroxymethylpyrrolidin-3-yl 4-O-(6-deoxy-α-D-glucopyranosyl)-α-D-glucopyranoside (11a) (2R,3R,4S)—N-Benzyloxycarbonyl-4-benzyloxy-2-benzyloxymethyl-3-hydroxy-pyrrolidine The compound (815 mg, 1.77 mmol) synthesized in Reference example 9 (9b) was dissolved in dichloromethane:cyclohexane (1:2, 45 mL), and benzyltrichloroacetimidate (0.66 mL, 3.54 mmol) and trifluoromethanesulfonic acid (24 µL, 0.27 mmol) were added thereto, followed by stirring of the mixture at room temperature for 1.5 hours. A saturated aqueous sodium hydrogencarbonate solution (5 mL) was added to the reaction mixture at 0° C. and after the mixture was diluted with ethyl acetate (200 mL), it was washed with water (50 mL) and a saturated aqueous sodium hydrogencarbonate solution (50 mL). After it was dried with anhydrous sodium sulfate, the solvent was distilled off under reduced pressure. The residue was purified using silica gel flash column chromatography (hexane:ethyl acetate, 4:1, V/V) to obtain a pale yellow oil (866 mg). The thus obtained pale yellow oil (866 mg) was dissolved in methanol (15 mL) and potassium carbonate (65 mg) was added thereto, followed by stirring of the mixture at room temperature for 1 hour. After the solvent was distilled off under reduced pressure, water (20 mL) was added thereto. After the mixture was extracted with ethyl acetate, the organic layer was washed with a saturated aqueous NaCl solution (20 mL). The solvent was distilled off under reduced pressure and the residue was purified using silica gel flash column chromatography (hexane:ethyl acetate, 5:1-2:1, V/V) to obtain the desired title compound (233 mg, yield: 30%) as a colorless oil.
¹H NMR (400 MHz, CDCl₃): δ 3.35-4.25 (6H, m), 4.25-4.70 (4H, m), 5.00-5.30 (4H, m), 7.09-7.26 (15H, m);
MS (FAB) m/z: 448 (M+H)⁺.

(11b) (2R,3R,4S)—N-Benzyloxycarbonyl-2-benzyloxymethyl-4-benzyloxypyrrolidin-3-yl 2,3,6-tri-O-benzyl-4-O-(2,3,4-tri-O-benzyl-6-deoxy-α-D-glucopyranosyl)-α-D-glucopyranoside The compound (513 mg, 0.59 mmol) synthesized in Reference example 1 (1f) was dissolved in methylene chloride (10 mL), and trichloroacetonitrile (0.3 mL, 2.95 mmol) and 1,8-diazabicyclo[5.4.0]-7-undecene (9 µL, 0.06 mmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain colorless oily imidate (447 mg, 75%). The compound (233 mg, 0.52 mmol) synthesized in Reference example 11 (11a) was dissolved in diethyl ether (10 mL) and trimethylsilyl trifluoromethanesulfonate (9 μL, 59 μmol) was added thereto under a nitrogen atmosphere. A solution of the imidate in diethyl ether (5 mL) solution was added to the reaction mixture and the mixture was stirred at room temperature for 1.5 hours. Triethylamine (16 μL, 118 μmol) was added to the reaction mixture and after the solvent was distilled off under reduced pressure, it was diluted with ethyl acetate (20 mL) and the mixture was washed with a saturated aqueous sodium hydrogencarbonate solution (20 mL) and a saturated aqueous NaCl solution (20 mL). After the organic layer was dried with anhydrous sodium sulfate, the solvent was distilled off under reduced pressure and the residue was purified using silica gel flash column chromatography (hexane:diethyl ether, 5:1-4:1, V/V) to obtain the desired title compound α form (58 mg, 8%) and β form (51 mg, 7%) as a colorless oil.

$^1$H NMR (400 MHz, CDCl$_3$): δ 1.15 (3H, d, J=5.6 Hz), 3.10-5.20 (36H, m), 1.15 (1H, d, J=6.3 Hz), 7.20-7.39 (45H, m);

MS (FAB) m/z: 1297 (M+H)$^+$.

(11c) (2R,3R,4S)-4-Hydroxy-2-hydroxymethylpyrrolidin-3-yl 4-O-(6-deoxy-α-D-glucopyranosyl)-α-D-glucopyranoside The compound (58 mg, 44.7 μmol) synthesized in Reference example 11 (11b) was dissolved in a 1% hydrochloric acid-methanol solution (5 mL) and 20% palladium hydroxide-carbon (30 mg) was added thereto, followed by stirring of the mixture under a hydrogen atmosphere for 1.5 hours. After the catalyst was removed by Celite filtration, 28% ammonia water (0.2 mL) was added thereto and the mixture was stirred for 10 minutes. The solvent was distilled off under reduced pressure and after the residue was passed through an ion exchange resin (Dowex 50w×8) column with water (30 mL), 1% ammonia water (30 mL) was passed through. The ammonia water containing the desired compound was concentrated under reduced pressure and it was purified using silica gel flash column chromatography (ethyl acetate:methanol:water, 5:2:1-1:1:1, V/V) to obtain the desired title compound (13 mg, 68%) as a colorless solid.

$^1$H NMR (400 MHz, D$_2$O): δ 1.19 (3H, d, J=4.1 Hz), 2.80-4.60 (17H, m), 5.00 (1H, d, J=3.6 Hz), 5.24 (1H, d, J=3.0 Hz);

MS (FAB) m/z: 442 (M+H)$^+$.

Reference Example 12

(2R,3R,4R)-2-Hydroxymethyl-3-hydroxypyrrolidin-4-yl 4-O-(6-deoxy-β-D-glucopyranosyl)-α-D-glucopyranoside (12a) (2R,3R,4R)—N-Benzyloxycarbonyl-2-benzyloxymethyl-3-hydroxypyrrolidin-4-yl 2,3,6-tri-O-benzyl-4-O-(2,3,4-tri-O-benzyl-6-deoxy-β-D-glucopyranosyl)-α-D-glucopyranoside The compound (607 mg, 0.70 mmol) synthesized in Reference example 2 (2f) was dissolved in methylene chloride (10 mL), and trichloroacetonitrile (500 μL, 4.98 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain the imidate (630 mg, 89%) as a yellow oil. The compound (323 mg, 0.700 mmol) synthesized in Reference example 9 (9a) was dissolved in diethyl ether (10 mL), the imidate (630 mg, 0.623 mmol) was added thereto and trimethylsilyl trifluoromethanesulfonate (6.3 μL, 34.8 μmol) was added dropwise thereto, followed by stirring of the mixture at room temperature for 45 minutes. After triethylamine (4 drops) was added to the reaction mixture, the solvent was distilled off under reduced pressure. The residue was purified using silica gel flash column chromatography (hexane:diethyl ether, 6:1, V/V) to obtain the desired title compound (610 mg, 75%) as a pale yellow oil. Subsequently, the pale yellow oil (610 mg, 0.465 mmol) was dissolved in methanol (10 mL) and an aqueous potassium carbonate solution (1M, 1 mL, 1 mmol) was added thereto, followed by stirring of the mixture at room temperature for 3 hours. The solvent was distilled off under reduced pressure and the residue was purified using silica gel flash column chromatography (hexane:diethyl ether, 2:1, V/V) to obtain the desired title compound (280 mg, yield: 50%) as a colorless solid.

$^1$H NMR (400 MHz, D$_2$O): δ 1.19 (3H, d, J=5.8 Hz), 2.83 (1H, brs), 3.12 (1H, t, J=9.3 Hz), 3.17-3.23 (1H, m), 3.29-3.37 (2H, m), 3.39-3.45 (2H, m), 3.51 (1H, dd, J=9.76, 2.93 Hz), 3.60 (1H, brt, J=7.8 Hz), 3.72-4.01 (7H, m), 4.27-4.56 (6H, m), 4.60-4.63 (2H, m), 4.73-4.75 (4H, brm), 4.78 (1H, d, J=10.75 Hz), 4.85 (1H, d, J=10.74 Hz), 4.87 (1H, d, J=9.77 Hz), 4.92 (1H, d, J=2.93 Hz), 5.01-5.12 (3H, m), 7.21-7.34 (38H, m), 7.43 (2H, d, J=6.83 Hz);

MS (FAB) m/z: 1207 (M+H)$^+$.

(12b) (2R,3R,4R)-2-Hydroxymethyl-3-hydroxypyrrolidin-4-yl 4-O-(6-deoxy-β-D-glucopyranosyl)-α-D-glucopyranoside The compound (90 mg, 74.6 μmol) synthesized in Reference example 12 (12a) was dissolved in methanol (10 mL) and hydrochloric acid (140 μL) and 20% palladium hydroxide-carbon (90 mg) were added thereto, followed by stirring of the mixture at room temperature under a hydrogen atmosphere for 2 hours. After it was filtered through Celite, ammonia water (5%) was added thereto until the pH became neutral. The solvent was distilled off under reduced pressure and the residue was purfied by an ion exchange resin (Dowex 50w×8) column (water-5% ammonia water). Further, it was purified using silica gel flash column chromatography (ethyl acetate:methanol:water, 1:1:1, V/V) to obtain desired title compound (26 mg, 79%) as a colorless solid.

$^1$H NMR (400 MHz, D$_2$O): δ 1.32 (3H, d, J=5.8 Hz), 3.17-3.22 (2H, m), 3.30-3.38 (2H, m), 3.44-3.55 (2H, m), 3.60-3.64 (2H, m), 3.74-3.86 (6H, m), 3.92 (1H, brd, J=11.72 Hz), 4.13 (1H, brs), 4.24 (1H, brs), 4.48 (1H, d, J=7.81 Hz), 5.11 (1H, d, J=2.93 Hz); MS (FAB) m/z: 442 (M+H)$^+$.

Reference Example 13

(2R,3R,4R)-4-Hydroxy-2-hydroxymethylpyrrolidin-3-yl 4-O-(6-deoxy-α-D-glucopyranosyl)-β-D-glucopyranoside The compound β form (60 mg, 46.3 μmol) synthesized in Reference example 1 (1j) was dissolved in methanol (4 mL), and hydrochloric acid (56 μL) and 20% palladium hydroxide-carbon (60 mg) were added thereto, followed by stirring of the mixture at room temperature under a hydrogen atmosphere for 4 hours. After it was filtered through Celite, 18% ammonia water (3 drops) was added thereto. The solvent was distilled off under reduced pressure and the residue was purified by an ion exchange resin (Dowex 50w×8) column (water-5% ammonia water). Further, it was purified using silica gel flash column chromatography (ethyl acetate:methanol:water, 3:2: 1, V/V) to obtain the desired title compound (10 mg, 49%) as a colorless solid.

$^1$H NMR (400 MHz, D$_2$O): δ 1.29 (3H, d, J=5.8 Hz), 2.93 (1H, dd, J=11.7, 3.6 Hz), 3.15-3.35 (4H, m), 3.51-3.65 (5H, m), 3.74-3.80 (5H, m), 3.93-4.00 (2H, m), 4.40 (1H, br, s), 4.56 (1H, d, J=7.3 Hz), 5.34 (1H, br, s);

MS (FAB) m/z: 464 (M+Na)$^+$, 442 (M+H)$^+$.

Reference Example 14

(1R,2S,3R,4R,5R)-1-Amino-2,3-dihydroxy-5-hydroxymethylcyclopent-4-yl 4-O-(6-deoxy-α-D-glucopyranosyl)-α-D-glucopyranoside (14a) Methyl 4-O-benzoyl-2,3-di-O-benzyl-6-O-p-toluenesulfonyl-α-D-glucopyranoside Methyl 2,3-di-O-Benzyl-6-O-p-toluenesulfonyl-α-D-glucopyranoside (J. Org. Chem., 2001, 66, 5965-5975) (163.9 g, 310 mmol) was dissolved in methylene chloride (1.5 L), 4-dimethylaminopyridine (43.5 g, 352 mmol) and triethylamine (49.0 mL, 352 mmol) were added thereto and benzoyl chloride (43.2 mL, 372 mmol) was added dropwise thereto under ice-cooling, followed by stirring of the mixture at 0° C. for 1 hour. Diluted hydrochloric acid (2N, 500 mL) was added to the reaction mixture and after the mixture was extracted with methylene chloride (1 L), the organic layer was washed with a saturated aqueous sodium hydrogencarbonate solution (1 L) and a saturated aqueous NaCl solution (1 L). After it was dried with anhydrous sodium sulfate, the solvent was distilled off under reduced pressure. The residue was purified using silica gel flash column chromatography (hexane:ethyl acetate, 1:1, V/V) to obtain the desired title compound (196 g, yield: 99%) as a colorless solid.

$^1$H NMR (400 MHz, CDCl$_3$): δ 2.34 (3H, s), 3.40 (3H, s), 3.58 (1H, dd, J=9.3, 3.4 Hz), 3.98-4.10 (4H, m), 4.57-4.65 (3H, m), 4.79 (1H, d, J=10.8 Hz), 5.06 (1H, dd, J=9.8, 9.8 Hz), 7.08-7.10 (5H, m), 7.18 (2H, d, J=7.8 Hz), 7.29-7.35 (5H, m), 7.41-7.45 (2H, m), 7.57-7.61 (1H, m), 7.67 (2H, d, J=7.8 Hz), 7.89 (2H, d, J=8.8 Hz);

MS (FAB) m/z: 633 (M+H)$^+$.

(14b) Methyl 4-O-benzoyl-2,3-di-O-benzyl-6-deoxy-6-iodo-α-D-glucopyranoside

The compound (196 g, 310 mmol) synthesized in Reference example 14 (14a) was dissolved in toluene (2 L), and sodium iodide (235 g, 1.57 mol) and 18-crown-6-ether (16.6 g, 62.8 mmol) were added thereto under a nitrogen atmosphere, followed by stirring of the mixture at 100° C. for 2 hours. The reaction mixture was cooled to room temperature and filtered and the filtered product was washed with toluene. The filtrate and the washing liquid were washed with a saturated aqueous sodium hydrogencarbonate solution (1 L) and a saturated aqueous NaCl solution (1 L). After it was dried with anhydrous sodium sulfate, the solvent was distilled off under reduced pressure to obtain the desired title compound (181 g, yield: 99%) as a colorless solid. $^1$H NMR (400 MHz, CDCl$_3$): δ 3.12 (1H, dd, J=11.0, 8.8 Hz), 3.29 (1H, dd, J=11.0, 2.2 Hz), 3.51 (3H, s), 3.64 (1H, dd, J=9.6, 3.7 Hz), 3.82-3.89 (1H, m), 4.06 (1H, dd, J=9.6, 8.8 Hz), 4.60-4.68 (3H, m), 4.82 (1H, d, J=11.0 Hz), 4.82 (1H, d, J=12.8 Hz), 5.06 (1H, dd, J=9.5, 9.5 Hz), 7.08-7.10 (5H, m), 7.29-7.38 (5H, m), 7.42-7.47 (2H, m), 7.57-7.61 (1H, m), 7.98 (2H, d, J=8.0 Hz);

MS (FAB) m/z: 589 (M+H)$^+$.

(14c) 4-O-Benzoyl-2,3-di-O-benzyl-5,6-dideoxy-D-xylo-hexa-5-enose oxime

The compound (181 g, 307 mmol) synthesized in Reference example 14 (14b) was dissolved in isopropanol (1.5 L) and distilled water (50 mL) and zinc powder (180 g) washed with diluted hydrochloric acid was added thereto, followed by stirring of the mixture at 100° C. for 1 hour. The reaction mixture was filtered through Celite and the filtered product was washed with ethanol, followed by distillation of the filtrate and the washing liquid under reduced pressure. The residue was dissolved in ethanol (500 mL), and hydroxylamine hydrochloride (42.7 g, 615 mmol) and pyridine (49.7 mL, 615 mmol) were added thereto, followed by stirring of the mixture at 80° C. for 40 minutes. The solvent was distilled off under reduced pressure and the residue was purified using silica gel flash column chromatography (hexane:ethyl acetate, 5:1, V/V) to obtain the desired title compound (126 g, yield: 92%) as a colorless solid.

$^1$H NMR (400 MHz, CDCl$_3$): δ 3.83 (0.7H, dd, J=5.8, 4.9 Hz), 3.99 (0.3H, dd, J=6.2, 3.9 Hz), 4.23 (0.7H, dd, J=7.8, 4.9 Hz), 4.42 (1H, dd, J=11.8, 3.9 Hz), 4.65 (1H, d, J=11.7 Hz), 4.68-4.76 (3H, m), 4.97 (0.3H, dd, J=5.8, 3.9 Hz), 5.23 (1H, dd, J=10.7, 5.9 Hz), 5.31-5.37 (1H, m), 5.78-5.94 (2H, m), 7.20-7.38 (9H, m), 7.40-7.48 (3H, m), 7.53-7.59 (1H, m), 8.00-8.07 (2H, m);

MS (FAB) m/z: 446 (M+H)$^+$.

(14d) (3aR,4R,5R,6S,6aR)-4-Benzoyloxy-5,6-dibenzyloxyhexahydro-cyclopent[c]isooxazole The compound (126 g, 282 mmol) synthesized in Reference example 14 (14c) was dissolved in toluene (800 mL) and the mixture was stirred at 120° C. for 8 hours. The solvent was distilled off under reduced pressure and the residue was purified using silica gel flash column chromatography (hexane:ethyl acetate, 3:1, V/V) to obtain the desired title compound (59.7 g, yield: 48%) as a colorless solid.

$^1$H NMR (400 MHz, CDCl$_3$): δ 2.83-2.91 (1H, m), 3.45-3.60 (1H, m), 3.89-3.95 (2H, m), 4.11-4.18 (1H, m), 4.55 (1H, m), 4.75-4.87 (4H, m), 5.01 (1H, dd, J=7.8, 6.8 Hz), 5.09-5.13 (1H, m), 7.22-7.40 (10H, m), 7.43-7.47 (2H, m), 7.57-7.61 (1H, m), 7.97-8.00 (2H, m);

MS (FAB) m/z: 446 (M+H)$^+$.

(14e) (3aR,4R,5S,6S,6aR)-1-Benzyloxycarbonyl-5, 6-dibenzyloxy-4-hydroxy-hexahydrocyclopent[c]isooxazole The compound (59.7 g, 134 mmol) synthesized in Reference example 14 (14d) was dissolved in methanol (1 L) and sodium methoxide (10 mL, 49 mmol) was added thereto, followed by stirring of the mixture at room temperature for 15 minutes. A saturated aqueous ammonium chloride solution (500 mL) was added to the reaction mixture at 0° C. and after the mixture was extracted with ethyl acetate (1.5 L), the organic layer was washed with a saturated aqueous NaCl solution (50 mL). A saturated aqueous sodium hydrogencarbonate solution (500 mL) and benzyloxy chloroformate (22.9 mL, 160 mmol) were added to the organic layer at 0° C. and the mixture was stirred at 0° C. for 1 hour. The organic layer was washed with a saturated aqueous NaCl solution (500 mL) and after it was dried with anhydrous sodium sulfate, the solvent was distilled off under reduced pressure. The residue was purified using silica gel flash column chromatography (hexane:ethyl acetate, 1:1, V/V) to obtain the desired title compound (61.3 g, yield: 96%) as a colorless solid.

$^1$H NMR (400 MHz, CDCl$_3$): δ 2.30 (1H, brd, J=3.7 Hz, OH), 2.91 (1H, ddd, J=8.9, 8.9, 5.7 Hz, H-3a), 3.58 (1H, dd, J=9.0, 5.7 Hz, H-3), 3.73 (1H, dd, J=8.6, 8.4 Hz, H-5), 3.82 (1H, ddd, J=8.9, 8.6, 3.7 Hz, H-4), 3.84 (1H, dd, J=8.4, 5.6 Hz, H-6), 3.98 (1H, d, J=9.0 Hz, H-3), 4.54 (1H, d, J=11.3 Hz), 4.54 (1H, dd, J=8.9, 5.6 Hz, H-6a), 4.63 (1H, d, J=11.7 Hz), 4.84 (1H, d, J=11.3 Hz), 4.87 (1H, d, J=11.7 Hz), 5.20 (1H, d, J=12.1 Hz), 5.27 (1H, d, J=12.1 Hz), 7.23-7.40 (15H, m).

MS (FAB) m/z: 476 (M+H)$^+$.

(14f) (3 aR,4R,5R,6S,6aR)-1-Benzyloxycarbonyl-5, 6-dibenzyloxyhexahydro-cyclopent[c]isooxazol-4-yl 2,3,6-tri-O-benzyl-4-O-(6-deoxy-2,3,4-tri-O-benzyl-α-D-glucopyranosyl)-α-D-glucopyranoside The compound (215 mg, 0.248 mmol) synthesized in Reference example 1 (1f) was dissolved in methylene chloride (5 mL), and trichloroacetonitrile (460 μL, 4.61 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (250 mg, 99%) as a yellow oil. The compound (100 mg, 0.21 mmol) synthesized in Reference example 14 (14e) was dissolved in diethyl ether (10 mL), the imidate (250 mg, 0.248 mmol) was added thereto and trimethylsilyl trifluoromethanesulfonate (3.8 μL, 0.021 mmol) was added dropwise thereto, followed by stirring of the mixture at room temperature for 45 minutes. After triethylamine (4 drops) was added to the reaction mixture, the solvent was distilled off under reduced pressure. The residue was purified using silica gel flash column chromatography (hexane:diethyl ether, 2:1, V/V) to obtain the desired title compound (55 mg, 17%) as a pale yellow oil.

$^1$H NMR (400 MHz, CDCl$_3$): δ 1.15 (3H, d, J=6.8 Hz), 3.01-3.12 (2H, m), 3.14 (1H, dd, J=9.8, 3.9 Hz), 3.50-3.62 (3H, m), 3.64-3.80 (2H, m), 3.80-3.96 (5H, m), 3.99-4.10 (2H, m), 4.43 (1H, d, J=11.7 Hz), 4.47 (1H, d, J=11.7 Hz), 4.50-4.62 (7H, m), 4.68-4.93 (8H, m), 5.06 (1H, d, J=11.7 Hz), 5.18-5.29 (3H, m), 5.61 (1H, d, J=3.9 Hz), 7.05-7.41 (45H, m);

MS (FAB) m/z: 1324 (M+H)$^+$.

(14g) (1R,2S,3R,4R,5R)-1-Amino-2,3-dihydroxy-5-hydroxymethylcyclopent-4-yl 4-O-(6-deoxy-α-D-glucopyranosyl)-α-D-glucopyranoside The compound (53 mg, 40.4 μmol) synthesized in Reference example 14 (14f) was dissolved in methanol (10 mL), and hydrochloric acid (10 μL) and 20% palladium hydroxide-carbon (53 mg) were added thereto, followed by stirring of the mixture at room temperature under a hydrogen atmosphere for 4 hours. After the reaction mixture was filtered through Celite, the solvent was distilled off under reduced pressure and the residue was purified using an ion exchange resin (Dowex 50w×8) column (water-5% ammonia water). It was further purified using silica gel flash column chromatography (ethyl acetate:methanol:water, 1:1:1, V/V) to obtain the desired title compound (5 mg, 26%) as a colorless solid.

$^1$H NMR (400 MHz, D$_2$O): δ 1.18 (3H, d, J=6.8 Hz), 2.00-2.08 (1H, m), 2.15-2.22 (1H, m), 3.03-3.09 (1H, m), 3.16-3.22 (1H, m), 3.45-3.57 (5H, m), 3.58-3.78 (8H, m), 3.81-3.89 (3H, m), 5.10 (1H, d, J=2.9 Hz), 5.23 (1H, d, J=2.9 Hz);

MS (FAB) m/z: 472 (M+H)$^+$.

Reference Example 15

(1R,2S,3R,4R,5R)-1-Amino-2,3-dihydroxy-5-hydroxymethylcyclopent-4-yl 4-O-(6-deoxy-β-D-glucopyranosyl)-α-D-glucopyranoside (15a) (3aR,4R,5R,6S,6aR)-1-Benzyloxycarbonyl-5, 6-dibenzyloxy-hexahydro-cyclopent[c]isooxazol-4-yl 2,3,6-tri-O-benzyl-4-O-(6-deoxy-2,3,4-tri-O-benzyl-β-D-glucopyranosyl)-α-D-glucopyranoside The compound (1.0 g, 1.15 mmol) synthesized in Reference example 2 (2f) was dissolved in methylene chloride (30 mL), and trichloroacetonitrile (460 μL, 4.61 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (970 mg, 84%) as a yellow oil. The compound (508 mg, 1.06 mmol) synthesized in Reference example 14 (14e) was dissolved in diethyl ether (20 mL), the imidate (970 mg, 0.97 mmol) was added thereto and trimethylsilyl trifluoromethanesulfonate (17 μL, 0.097 mmol) was added dropwise thereto, followed by stirring of the mixture at room temperature for 45 minutes. After triethylamine (4 drops) was added to the reaction mixture, the solvent was distilled off under reduced pressure. The residue was purified using silica gel flash column chromatography (hexane:diethyl ether, 1:1, V/V) to obtain the title desired compound (125 mg, 9%) as a pale yellow oil.

$^1$H NMR (400 MHz, CDCl$_3$): δ 1.22 (3H, d, J=6.8 Hz), 2.81-2.87 (1H, m), 3.15 (1H, dd, J=9.8, 8.7 Hz), 3.19-3.24 (1H, m), 3.28-3.36 (2H, m), 3.40-3.45 (1H, m), 3.52 (1H, dd, J=8.8, 3.9 Hz), 3.55-3.59 (1H, m), 3.75 (1H, dd, J=10.7, 3.9 Hz), 3.79-3.84 (2H, m), 3.86-3.91 (1H, m), 3.93-4.01 (2H, m), 4.31 (1H, d, J=11.7 Hz), 4.35 (1H, d, J=7.8 Hz), 4.50 (1H, d, J=11.7 Hz), 4.52-4.59 (2H, m), 4.60-4.64 (3H, m), 4.70-4.87 (10H, m), 4.89 (1H, d, J=12.7 Hz), 5.00 (1H, d, J=10.7 Hz), 5.07 (1H, d, J=3.9 Hz), 5.21 (1H, d, J=11.7 Hz), 5.28 (1H, d, J=12.7 Hz), 7.10-7.43 (45H, m);

MS (FAB) m/z: 1324 (M+H)$^+$.

(15b) (1R,2S,3R,4R,5R)-1-Amino-2,3-dihydroxy-5-hydroxymethylcyclopent-4-yl 4-O-(6-deoxy-β-D-glucopyranosyl)-α-D-glucopyranoside The compound (115 mg, 86.8 μmol) synthesized in Reference example 15 (15a) was dissolved in methanol (20 mL) and ethyl acetate (1 mL), and hydrochloric acid (10 μL) and 20% palladium hydroxide-carbon (115 mg) were added thereto, followed by stirring of the mixture at room temperature under a hydrogen atmosphere for 4 hours. After the reaction mixture was filtered though Celite, the solvent was distilled off under reduced pressure and the residue was purified using an ion exchange resin (Dowex 50w×8) column (water-5% ammonia water). Further, it was purified using silica gel flash column chromatography (ethyl acetate:methanol:water, 1:1:1, V/V) to obtain the desired title compound (30 mg, 73%) as a colorless amorphous substance.

$[\alpha]_D^{20}$+60.9 (c 0.11, H$_2$O);

$^1$H NMR (400 MHz, D$_2$O): δ 1.21 (3H, d, J=6.8 Hz), 2.17-2.25 (1H, m), 3.05-3.10 (1H, m), 3.18-3.27 (2H, m), 3.30-3.92 (14H, m), 4.38 (1H, d, J=7.8 Hz), 5.08-5.10 (1H, m); MS (FAB) m/z: 472 (M+H)$^+$.

Reference Example 16

(1R,2S,3R,4R,5R)-1-(2-Hydroxy-1-hydroxymethylethylamino)-2,3-dihydroxy-5-hydroxymethylcyclopent-4-yl 4-O-(6-deoxy-β-D-glucopyranosyl)-α-D-glucopyranoside (16a) (3aR,4R,5R,6S,6aR)-4-Benzoyloxy-5,6-dibenzyloxy-1-(1,3-dihydroxyprop-2-yl)-hexahydrocyclopent[c]isooxazole The compound (3.07 g, 6.89 mmol) synthesized in Reference example 14 (14d) was dissolved in methanol (10 mL) and tetrahydrofuran (10 mL), and 1,3-dihydroxyacetone (1.86 g, 20.7 mmol) and acetic acid (1 mL) were added thereto, followed by stirring of the mixture at 70° C. for 30 minutes. Sodium cyanoborohydride (1.30 g, 20.67 mmol) was added to the reaction mixture and the mixture was stirred at 70° C. for 10 hours. The solvent was distilled off under reduced pressure and the residue was purified using silica gel flash column chromatography (methylene chloride:methanol, 20:1, V/V) to obtain the desired title compound (1.20 g, yield: 33%) as a colorless solid.

$^1$H NMR (400 MHz, CDCl$_3$): δ 2.35 (1H, dd, J=6.8, 4.9 Hz), 2.39 (1H, t, J=5.9 Hz), 2.77-2.82 (1H, m), 2.93-3.00 (1H, m), 3.74-3.84 (3H, m), 3.88-3.94 (1H, m), 3.96-4.08 (3H, m), 4.21-4.26 (2H, m), 4.74-4.86 (4H, m), 5.05 (1H, d, J=7.8, 5.9 Hz), 7.26-7.38 (10H, m), 7.45-7.50 (2H, m), 7.59-7.64 (1H, m), 7.98-8.02 (2H, m);

MS (FAB) m/z: 520 (M+H)$^+$.

(16b) (3aR,4R,5S,6S,6aR)-5,6-Dibenzyloxy-1-(2,2-dimethyl-[1,3]dioxan-5-yl)-4-hydroxyhexahydrocyclopent[c]isooxazole The compound (1.20 g, 2.31 mmol) synthesized in Reference example 16 (16a) was dissolved in acetone (30 mL), and 2,2-dimethoxypropane (2.27 mL, 18.5 mmol) and p-toluenesulfonic acid monohydrate (660 mg, 3.47 mmol) were added thereto, followed by stirring of the mixture at room temperature for 15 minutes. A saturated aqueous sodium hydrogencarbonate solution (50 mL) was added to the reaction mixture at 0° C. and after the mixture was extracted with ethyl acetate (50 mL), the organic layer was washed with a saturated aqueous NaCl solution (50 mL). The solvent was distilled off under reduced pressure and the residue was dissolved in methanol. Sodium methoxide (0.4 mL, 1.96 mmol) was added thereto and the mixture was stirred at room temperature for 20 minutes. A saturated aqueous ammonium chloride solution (50 mL) was added to the reaction mixture at 0° C. and after the mixture was extracted with ethyl acetate (50 mL), the organic layer was washed with a saturated aqueous NaCl solution (50 mL). After it was dried with anhydrous sodium sulfate, the solvent was distilled off under reduced pressure. The residue was purified using silica gel flash column chromatography (hexane:ethyl acetate, 1:1, V/V) to obtain the desired title compound (840 mg, yield: 80%) as a colorless solid.

$^1$H NMR (400 MHz, CDCl$_3$): δ 1.39 (3H, s), 1.47 (3H, s), 2.06 (1H, d, J=3.9 Hz), 2.85-2.96 (2H, m), 3.49 (1H, dd, J=9.8, 6.8 Hz), 3.67-3.72 (1H, m), 3.75-3.85 (6H, m), 3.89-3.97 (2H, m), 4.67 (1H, d, J=11.7 Hz), 4.68 (1H, d, J=11.7 Hz), 4.76 (1H, d, J=11.7 Hz), 4.85 (1H, d, J=11.7 Hz), 7.26-7.38 (10H, m);

MS (FAB) m/z 456: (M+H)$^+$.

(16c) (3aR,4R,5S,6S,6aR)-5,6-Dibenzyloxy-1-(2,2-dimethyl-[1,3]dioxan-5-yl)-hexahydrocyclopent[c]isooxazol-4-yl 2,3,6-tri-O-benzyl-4-O-(6-deoxy-2,3,4-tri-O-benzyl-β-D-glucopyranosyl)-α-D-glucopyranoside The compound (600 mg, 0.692 mmol) synthesized in Reference example 2 (2f) was dissolved in methylene chloride (20 mL), and trichloroacetonitrile (277 μL, 2.76 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (550 mg, 80%) as a yellow oil. The compound (230 mg, 0.501 mmol) synthesized in Reference example 16 (16b) was dissolved in diethyl ether (10 mL), the imidate (550 mg, 0.551 mmol) was added thereto and trimethylsilyl trifluoromethanesulfonate (45 μL, 0.250 mmol) was added dropwise thereto, followed by stirring of the mixture at room temperature for 45 minutes. After triethylamine (4 drops) was added to the reaction mixture, the solvent was distilled off under reduced pressure. The residue was purified using silica gel flash column chromatography (hexane:ethyl acetate, 3:1, V/V) to obtain the desired title compound (140 mg, 20%) as a pale yellow oil.

$^1$H NMR (400 MHz, CDCl$_3$): δ 1.22 (3H, d, J=5.8 Hz), 1.43 (3H, s), 1.49 (3H, s), 2.70-2.80 (2H, m), 3.11-3.17 (1H, m), 3.19-3.27 (1H, m), 3.30-3.54 (6H, m), 3.61-3.95 (12H, m), 4.34 (1H, d, J=11.7 Hz), 4.38 (1H, d, J=7.3 Hz), 4.52 (1H, d, J=12.5 Hz), 4.58-4.73 (5H, m), 4.73-4.90 (8H, m), 5.00 (1H, d, J=3.7 Hz), 5.03 (1H, d, J=11.0 Hz), 7.17-7.38 (38H, m), 7.43-7.47 (2H, m).

MS (FAB) m/z: 1304 (M+H)$^+$.

(16d) (1R,2S,3R,4R,5R)-1-(2-Hydroxy-1-hydroxymethylethylamino)-2,3-dihydroxy-5-hydroxymethylcyclopent-4-yl 4-O-(6-deoxy-β-D-glucopyranosyl)-α-D-glucopyranoside The compound (146 mg, 113 μmol) synthesized in Reference example 16 (16c) was dissolved in acetic acid (10 mL) and distilled water (2.5 mL) and the mixture was stirred at 50° C. for 1 hour. The solvent was distilled off under reduced pressure and the residue was purified using silica gel flash column chromatography (hexane:ethyl acetate, 1:1, V/V) to obtain diol (128 mg, 101 μmol) as a colorless crystal. The diol (118 mg, 93.3 μmol) was dissolved in methanol (20 mL) and ethyl acetate (1 mL), and hydrochloric acid (30 μL) and 20% palladium hydroxide-carbon (118 mg) were added thereto, followed by stirring of the mixture at room temperature under a hydrogen atmosphere for 4 hours. After the reaction mixture was filtered through Celite, the solvent was distilled off under reduced pressure and the residue was purified using an ion exchange resin (Dowex 50w×8) column (water-5% ammonia water). Further, it was purified using silica gel flash column chromatography (ethyl acetate:methanol:water, 1:1:1, V/V) to obtain the desired title compound (43 mg, 84%) as a colorless solid.

¹H NMR (400 MHz, D₂O): δ 1.32 (3H, d, J=6.8 Hz), 2.34-2.41 (1H, m), 2.88-2.94 (1H, m), 3.16-3.22 (1H, m), 3.29-3.38 (2H, m), 3.42-3.50 (1H, m), 3.49-3.97 (16H, m), 4.48 (1H, d, J=7.8 Hz), 5.18 (1H, d, J=7.8 Hz);
¹³C NMR (100 MHz, D₂O): δ 16.9, 44.0, 58.5, 58.7, 60.0, 60.1, 60.6, 61.3, 70.9, 71.3, 71.6, 72.2, 73.6, 75.0, 75.5, 79.1, 79.2, 80.5, 81.9, 97.8, 102.7;
MS (FAB) m/z: 546 (M+H)⁺.

Reference Example 17

(1R,2S,3S,4R,5R)-1-Amino-2-fluoro-3-hydroxy-5-hydroxymethylcyclopent-4-yl 4-O-(6-deoxy-β-D-glucopyranosyl)-α-D-glucopyranoside (17a) Methyl 2-deoxy-2-fluoro-D-glucopyranoside 1,3,4,6-tetra-O-Acetyl-2-deoxy-2-fluoro-β-D-glucopyranose (Carbohydr. Res., 153, 1986, 168-170) (13.4 g, 38.3 mmol) was dissolved in methanol (150 mL) and Dowex 50w×8 (19 g) was added thereto, followed by stirring of the mixture at 80° C. for 12 hours. The reaction mixture was filtered through Celite and the filtered product was washed with methanol. The filtered product and the washing liquid were combined and distilled off under reduced pressure. The residue was purified using silica gel flash column chromatography (methylene chloride:methanol, 10:1-5:1, V/V) to obtain the desired title compound (3.37 g, yield: 45%) as a colorless solid.
¹H NMR (400 MHz, CD₃OD): δ 3.32-3.36 (1H, m), 3.43 (1.5H, s), 3.52-3.64 (2H, m), 3.54 (1.5H, s), 3.65-3.70 (1H, m), 3.80-3.92 (2.5H, m), 4.16-4.29 (0.5H, m), 4.43 (0.5H, dd, J=7.8, 2.9 Hz), 4.88 (0.5H, d, J=3.9 Hz).
MS (FAB) m/z: 197 (M+H)⁺.

(17b) Methyl 4,6-O-benzylidene-2-deoxy-2-fluoro-D-glucopyranoside

The compound (3.5 g, 17.9 mmol) synthesized in Reference example 17 (17a) was dissolved in dimethylformamide (70 mL), and benzaldehyde dimethylacetal (3.75 mL, 25.0 mmol) and p-toluenesulfonic acid monohydrate (170 mg, 0.892 mmol) were added thereto, followed by stirring of the mixture at 50° C. under reduced pressure for 2 hours. Triethylamine (2 mL) was added to the reaction mixture and the solvent was distilled off under reduced pressure. The residue was purified using silica gel flash column chromatography (hexane:ethyl acetate, 3:1, V/V) to obtain the desired title compound (3.36 g, yield: 66%) as a colorless solid.
¹H NMR (400 MHz, CDCl₃): δ 3.42-3.58 (1H, m), 3.48 (2H, s), 3.60 (1H, s), 3.70-3.90 (1.33H, m), 3.98-4.08 (0.66H, m), 4.16-4.40 (2H, m), 4.48-4.54 (1H, m), 4.94 (0.66H, d, J=4.4 Hz), 5.02-5.06 (0.33H, m), 5.52-5.54 (1H, m), 7.36-7.41 (3H, m), 7.46-7.51 (2H, m);
MS (FAB) m/z: 285 (M+H)⁺.

(17c) Methyl 4-O-benzoyl-3-O-benzyl-2-deoxy-2-fluoro-6-O-p-toluenesulfonyl-D-glucopyranoside The compound (3.36 g, 11.8 mmol) synthesized in Reference example 17 (17b) was dissolved in dimethylformamide (50 mL) and sodium hydride (741 mg, 17.7 mmol) was added thereto under a nitrogen atmosphere, followed by stirring of the mixture at room temperature for 30 minutes. The reaction mixture was cooled with ice and benzyl bromide (1.68 mL, 14.1 mmol) was added thereto, followed by stirring of the mixture at room temperature for 2 hours. A saturated aqueous ammonium chloride solution (50 mL) was added to the reaction mixture at 0° C. and after the mixture was extracted with ethyl acetate (100 mL), the organic layer was washed with a saturated aqueous NaCl solution (100 mL). After it was dried with anhydrous sodium sulfate, the solvent was distilled off under reduced pressure. Acetic acid (16 mL) and distilled water (4 mL) were added to the residue and the mixture was stirred at 60° C. for 3 hours. The reaction mixture was azeotroped with toluene while the solvent was distilled off under reduced pressure. The residue was dissolved in pyridine (10 mL), and p-toluenesulfonic chloride (1.75 g, 9.20 mmol) and 4-dimethylaminopyridine (101 mg, 0.83 mmol) were added thereto under ice-cooling, followed by stirring of the mixture at room temperature for 6 hours. The reaction mixture was cooled with ice and diluted hydrochloric acid (2N, 80 mL) was added thereto. After the mixture was extracted with ethyl acetate (100 mL), the organic layer was washed with a saturated aqueous sodium hydrogencarbonate solution (200 mL) and a saturated aqueous NaCl solution (200 mL). After it was dried with anhydrous sodium sulfate, the solvent was distilled off under reduced pressure. The residue was dissolved in methylene chloride (40 mL), and 4-dimethylaminopyridine (1.28 g, 10.5 mmol), benzoyl chloride (1.30 mL, 11.2 mmol) and triethylamine (1.46 mL, 10.5 mmol) were added thereto under ice-cooling, followed by stirring of the mixture at 0° C. for 3 hours. The reaction mixture was cooled with ice and diluted hydrochloric acid (2N, 80 mL) was added thereto. After the mixture was extracted with methylene chloride (100 mL), the organic layer was washed with a saturated aqueous sodium hydrogencarbonate solution (200 mL) and a saturated aqueous NaCl solution (100 mL). After it was dried with anhydrous sodium sulfate, the solvent was distilled off under reduced pressure. The residue was purified using silica gel flash column chromatography (hexane:ethyl acetate, 3:1, V/V) to obtain the desired title compound (4.16 g, yield: 65%) as a colorless solid.
¹H NMR (400 MHz, CDCl₃): δ 2.35 (3/2H, s), 2.36 (3/2H, s), 3.47 (3/2H, s), 3.55 (3/2H, s), 3.79-3.88 (1H, m), 4.01-4.15 (3H, m), 4.28-4.62 (3.5H, m), 4.77 (1H, dd, J=11.7, 5.1 Hz), 4.91 (0.5H, d, J=4.4 Hz), 5.05-5.12 (1H, m), 7.06-7.10 (5H, m), 7.18-7.22 (2H, m), 7.42-7.48 (2H, m), 7.58-7.65 (1H, m), 7.66-7.71 (2H, m), 7.89-7.93 (2H, m);
MS (FAB) m/z: 545 (M+H)⁺.

(17d) Methyl 4-O-benzoyl-3-O-benzyl-2,6-dideoxy-2-fluoro-6-iodo-D-glucopyranoside The compound (3.83 g, 7.03 mmol) synthesized in Reference example 17 (17c) was dissolved in toluene (120 mL), and sodium iodide (5.27 g, 39.2 mmol) and 18-crown-6-ether (370 mg, 1.40 mmol) were added under a nitrogen atmosphere, followed by stirring of the mixture at 100° C. for 2 hours. The reaction mixture was cooled to room temperature and filtered and the filtered product was washed with toluene. The filtrate and the washing liquid were washed with a saturated aqueous sodium hydrogencarbonate solution (100 mL) and a saturated aqueous NaCl solution (100 mL). After it was dried with anhydrous sodium sulfate, the solvent was distilled off under reduced pressure. The residue was purified using silica gel flash column chromatography (hexane:ethyl acetate, 5:1, V/V) to obtain the desired title compound (3.38 g, yield: 96%) as a colorless solid.
¹H NMR (400 MHz, CDCl₃): δ 3.12-3.21 (1H, m), 3.27-3.32 (1H, m), 3.57-3.62 (1H, m), 3.58 (3/2H, s), 3.65 (3/2H, s), 3.82-3.91 (1H, m), 4.38-4.68 (5/2H, m), 4.79 (1H, dd, J=11.7, 6.8 Hz), 4.99 (1/2H, dd, J=3.9 Hz), 5.06-5.13 (1H, m), 7.07-7.18 (5H, m), 7.43-7.48 (2H, m), 7.59-7.64 (1H, m), 7.95-8.00 (2H, m);

MS (FAB) m/z: 501 (M+H)$^+$.

(17e) 4-O-Benzoyl-3-O-benzyl-2-fluoro-2,5,6-trideoxy-D-xylo-hexa-5-enose oxime The compound (3.37 g, 6.74 mmol) synthesized in Reference example 17 (17d) was dissolved in isopropanol (40 mL) and distilled water (1.3 mL), and zinc powder (4 g) washed with diluted hydrochloric acid was added thereto, followed by stirring of the mixture at 100° C. for 1 hour. The reaction mixture was filtered through Celite, the filtered product was washed with ethanol and the filtrate and the washing liquid were distilled off under reduced pressure. The residue was dissolved in ethanol (80 mL) and hydroxylamine hydrochloride (1.18 g, 17.1 mmol) and pyridine (1.38 mL, 17.1 mmol) were added thereto, followed by stirring of the mixture at 60° C. for 40 minutes. The solvent was distilled off under reduced pressure and the residue was purified using silica gel flash column chromatography (hexane:ethyl acetate, 5:1, V/V) to obtain the desired title compound (1.31 g, yield: 54%) as a colorless solid.

$^1$H NMR (400 MHz, CDCl$_3$): δ 3.87-3.94 (0.7H, m), 4.13-4.22 (0.3H, m), 4.64-4.82 (2H, m), 5.22 (0.7H, ddd, J=46.9, 6.8, 4.9 Hz), 5.34-5.55 (2H, m), 5.75-5.88 (1.3H, m), 5.98-6.07 (1H, m), 7.24-7.62 (8H, m), 8.03-8.08 (2H, m);

MS (FAB) m/z: 358 (M+H)$^+$.

(17f) (3 aR,4R,5S,6S,6aR)-4-Benzoyloxy-5-benzyloxy-6-fluorohexahydro-cyclopent[c]isooxazole The compound (1.31 g, 3.66 mmol) synthesized in Reference example 17 (17e) was dissolved in toluene (30 mL) and the mixture was stirred at 120° C. for 8 hours. The solvent was distilled off under reduced pressure and the residue was purified using silica gel flash column chromatography (hexane:ethyl acetate, 3:1, V/V) to obtain the desired title compound (965 mg, yield: 74%) as a colorless solid.

$^1$H NMR (400 MHz, CDCl$_3$): δ 2.91-2.98 (1H, m), 3.50-3.58 (1H, m), 4.00-4.10 (1H, m), 4.21-4.28 (1H, m), 4.54 (1H, brd, J=7.8 Hz), 4.72 (1H, d, J=12.7 Hz), 4.83 (1H, d, J=12.7 Hz), 4.84 (1H, ddd, J=52.7, 7.8, 5.8 Hz), 4.98-5.02 (1H, m), 5.11-5.15 (1H, m), 7.28-7.36 (5H, m), 7.45-7.49 (2H, m), 7.59-7.63 (1H, m), 7.97-8.00 (2H, m), MS (FAB) m/z 358: (M+H)$^+$.

(17g) (3aR,4R,5S,6S,6aR)-5-Benzyloxy-1-benzyloxycarbonyl-6-fluoro-4-hydroxy-hexahydrocyclopent[c]isooxazole The compound (950 mg, 2.66 mmol) synthesized in Reference example 17 (17f) was dissolved in methanol (10 mL) and sodium methoxide (270 μL, 1.30 mmol) was added thereto, followed by stirring of the mixture at room temperature for 15 minutes. A saturated aqueous ammonium chloride solution (50 mL) was added to the reaction mixture at 0° C. and after the mixture was extracted with ethyl acetate (50 mL), the organic layer was washed with a saturated aqueous NaCl solution (50 mL). After it was dried with anhydrous sodium sulfate, the solvent was distilled off under reduced pressure. The residue was dissolved in ethyl acetate (100 mL) and a saturated aqueous sodium hydrogencarbonate solution (50 mL) and benzyloxy chloroformate (570 μL, 4.00 mmol) were added thereto at 0° C., followed by stirring of the mixture at 0° C. for 1 hour. The organic layer was washed with a saturated aqueous NaCl solution (50 mL) and after it was dried with anhydrous sodium sulfate, the solvent was distilled off under reduced pressure. The residue was purified using silica gel flash column chromatography (hexane:ethyl acetate, 1:1, V/V) to obtain the desired title compound (1.00 g, yield: 97%) as a colorless solid.

$^1$H NMR (400 MHz, CDCl$_3$): δ 2.29 (1H, brd, J=3.3 Hz, OH), 2.92-2.99 (1H, m, H-3a), 3.60 (1H, dd, J=9.0, 5.8 Hz, H-3), 3.82-3.91 (2H, m, H-5, H-4), 3.98 (1H, d, J=8.8 Hz, H-3), 4.61 (1H, d, J=12.7 Hz, CH$_2$Ph), 4.62-4.70 (1H, m, H-6a), 4.72-4.76 (1/2H, m, H-6), 4.84 (1H, d, J=12.7 Hz, CH$_2$Ph), 4.82-4.86 (1/2H, m, H-6), 5.21 (2H, s), 7.23-7.40 (10H, m);

MS (FAB) m/z: 388(M+H)$^+$.

(17h) (3aR,4R,5S,6S,6aR)-5-Benzyloxy-1-benzyloxycarbonyl-6-fluorohexahydro-cyclopent[c]isooxazol-4-yl 2,3,6-tri-O-benzyl-4-O-(6-deoxy-2,3,4-tri-O-benzyl-β-D-glucopyranosyl)-α-D-glucopyranoside The compound (840 mg, 0.969 mmol) synthesized in Reference example 2 (2f) was dissolved in methylene chloride (10 mL), and trichloroacetonitrile (460 μL, 4.61 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (830 mg, 85%) as a yellow oil. The compound (300 mg, 0.756 mmol) synthesized in Reference example 17 (17 g) was dissolved in diethyl ether (15 mL), the imidate (830 mg, 0.832 mmol) was added thereto and trimethylsilyl trifluoromethanesulfonate (13 μL, 0.0756 mmol) was added dropwise thereto, followed by stirring of the mixture at room temperature for 45 minutes. After triethylamine (4 drops) was added to the reaction mixture, the solvent was distilled off under reduced pressure. The residue was purified using silica gel flash column chromatography (hexane:diethyl ether, 2:1, V/V) to obtain the desired title compound (86 mg, 9%) as a pale yellow oil.

$^1$H NMR (400 MHz, CDCl$_3$): δ 1.20 (3H, d, J=5.9 Hz), 2.87-2.94 (1H, m), 3.10-3.16 (1H, m), 3.19-3.24 (1H, m), 3.28-3.38 (3H, m), 3.42-3.46 (1H, m), 3.51 (1H, dd, J=9.8, 3.9 Hz), 3.55-3.59 (1H, m), 3.74 (1H, dd, J=10.7, 3.9 Hz), 3.79-3.84 (2H, m), 3.84-3.89 (1H, m), 3.94 (1H, d, J=9.8 Hz), 4.00-4.06 (1H, m), 4.31 (1H, d, J=12.7 Hz), 4.35 (1H, d, J=7.8 Hz), 4.49 (1H, d, J=12.7 Hz), 4.58-4.88 (13H, m), 5.01 (1H, d, J=10.8 Hz), 5.05 (1H, d, J=3.9 Hz), 5.18-5.26 (2H, m), 7.15-7.43 (40H, m);

MS (FAB) m/z: 1236 (M+H)$^+$.

(17i) (1R,2S,3S,4R,5R)-1-Amino-2-fluoro-3-hydroxy-5-hydroxymethylcyclopent-4-yl 4-O-(6-deoxy-β-D-glucopyranosyl)-α-D-glucopyranoside The compound (85 mg, 68.8 μmol) synthesized in Reference example 17 (17h) was dissolved in methanol (20 mL) and ethyl acetate (1 mL), and hydrochloric acid (30 μL) and 20% palladium hydroxide-carbon (85 mg) were added thereto, followed by stirring of the mixture at room temperature under a hydrogen atmosphere for 4 hours. After the reaction mixture was filtered through Celite, the solvent was distilled off under reduced pressure, and the residue was purified using an ion exchange resin (Dowex 50w×8) column (water-5% ammonia water). It was further purified using silica gel flash column chromatography (ethyl acetate:methanol:water, 1:1:1, V/V) to obtain the desired title compound (28 mg, 86%) as a colorless amorphous substance. $^1$H NMR (400 MHz, D$_2$O): δ 1.21 (3H, d, J=5.9 Hz), 2.23-2.30 (1H, m), 3.04-3.10 (1H, m), 3.18-3.25 (2H, m), 3.28-3.61 (6H, m), 3.64-3.80 (5H, m), 3.86-3.91 (1H, m), 4.11-4.18 (1H, m), 4.37 (1H, d, J=8.8 Hz), 4.41-4.46 (1/2H, m), 4.52-4.57 (1/2m), 5.06-5.08 (1H, m);

$^{13}$C NMR (100 MHz, D$_2$O): δ 16.9, 44.0, 58.5, 58.7, 60.0, 60.1, 60.6, 61.3, 70.9, 71.3, 71.6, 72.2, 73.6, 75.0, 75.5, 79.1, 79.2, 80.5, 81.9, 97.8, 102.7;

MS (FAB) m/z: 474 (M+H)$^+$.

Reference Example 18

(2R,3R,4R)-4-Hydroxy-2-hydroxymethyl-3,4-dihydro-2H-pyrrol-3-yl 4-O-(6-deoxy-α-D-glucopyranosyl)-α-D-glucopyranoside (18a) 1,2-O-Benzyl-4-deoxy-3-O-formyl-4-trifluoroacetamide-α-D-arabinoside 2-O-Benxyl-4-deoxy-3-O-formyl-4-trifluoroacetamido-D-arabinoside (Chem. Pharm. Bull., 1991, 39, 2807-2812) (0.80 g, 2.20 mmol) was dissolved in methylene chloride (50 mL), and benzyltrichloroacetamidate (0.82 mL, 4.40 mmol) and trifluoromethanesulfonic acid (40 μL, 0.22 mmol) were added thereto, followed by stirring of the mixture at room temperature for 3 hours. A saturated aqueous sodium hydrogencarbonate solution (30 mL) was added to the reaction mixture at 0° C. and after the mixture was diluted with ethyl acetate (100 mL), the mixture was washed with water (50 mL) and a saturated aqueous NaCl solution (50 mL). After it was dried with anhydrous sodium sulfate, the solvent was distilled off under reduced pressure. The residue was purified using silica gel flash column chromatography (hexane:ethyl acetate, 6:1, V/V) to obtain the desired title compound (0.73 g, yield: 74%) as a pale yellow amorphous substance.

$^1$H NMR (CDCl$_3$) δ: 3.55 (1H, dd, J=12.5, 2.2 Hz), 3.63 (1H, dd, J=10.3, 3.7 Hz), 4.13 (1H, d, J=13.9 Hz), 4.50 (1H, d, J=11.0 Hz), 4.53 (1H, d, J=12.5 Hz), 4.61 (1H, d, J=11.7 Hz), 4.62 (1H, br, s), 4.75 (1H, d, J=12.5 Hz), 4.90 (1H, d, J=2.9 Hz), 5.44 (1H, dd, J=10.3, 4.4 Hz), 6.69 (1H, d, J=7.33 Hz), 7.13-7.38 (10H, m), 8.00 (1H, s);

MS (FAB) m/z: 476 (M+Na)$^+$.

(18b) 1,2-di-O-Benzyl-4-deoxy-4-trifluoroacetamide-α-D-arabinoside

The compound (0.73 g, 1.61 mmol) synthesized in Reference example 18 (18a) was dissolved in methanol (30 mL) and water (5 mL), and potassium hydrogencarbonate (1.00 g, 10.0 mmol) was added thereto, followed by stirring of the mixture at room temperature for 15 hours. Ethyl acetate (50 mL) was added to the reaction mixture and the organic layer was washed with a saturated aqueous NaCl solution (20 mL). After it was dried with anhydrous sodium sulfate, the solvent was distilled off under reduced pressure. The residue was purified using silica gel flash column chromatography (hexane:ethyl acetate, 6:1, V/V) to obtain the desired title compound (205 mg, yield: 41%) as a colorless amorphous substance.

$^1$H NMR (CDCl$_3$) δ: 2.84 (1H, d, J=2.2 Hz), 3.44 (1H, dd, J=9.5, 2.9 Hz), 3.76 (1H, dd, J=12.5, 1.5 Hz), 3.92 (1H, dd, J=12.5, 1.5 Hz), 4.20-4.28 (2H, m), 4.47 (1H, d, J=11.7 Hz), 5.53 (2H, s), 4.72 (1H, d, J=12.5 Hz), 4.91 (1H, d, J=3.7 Hz), 6.67 (1H, br, d, J=5.86 Hz), 7.12-7.38 (10H, m);

MS (FAB) m/z: 426(M+H)$^+$, 448 (M+Na)$^+$.

(18c) 1,2-di-O-Benzyl-4-deoxy-4-trifluoroacetamido-3-O-{2,3,6-tri-O-benzyl-4-O-(2,3,4-tri-O-benzyl-6-deoxy-β-D-glucopyranosyl)-α-D-glucopyranosyl}-α-D-arabinoside The compound (0.70 g, 0.81 mmol) synthesized in Reference example 2 (2f) was dissolved in methylene chloride (20 mL), and trichloroacetonitrile (1.00 mL, 10.0 mmol) and 2 drops of 1,8-diazabicyclo[5.4.0]-7-undecene were added thereto, followed by stirring of the mixture at room temperature for 30 minutes. After the solvent was distilled off under reduced pressure, the residue was purified using silica gel flash column chromatography (hexane:ethyl acetate, 5:1, 1% triethylamine, V/V) to obtain colorless oily imidate (0.75 g, 92%). The compound (205 mg, 0.48 mmol) synthesized in Reference example 18 (18b) and the imidate (0.75 g, 0.74 mmol) were dissolved in diethyl ether (30 mL) and trimethylsilyl trifluoromethanesulfonate (8.7 μL, 0.074 mmol) was added thereto under a nitrogen atmosphere, followed by stirring of the mixture at room temperature for 3 hours. Triethylamine (0.1 mL) was added to the reaction mixture and after the solvent was distilled off under reduced pressure, the residue was diluted with ethyl acetate (30 mL) and the mixture was washed with a saturated aqueous hydrogencarbonate solution (20 mL) and a saturated aqueous NaCl solution (20 mL). After the organic layer was dried with anhydrous sodium sulfate, the solvent was distilled off under reduced pressure and the residue was purified using silica gel flash column chromatography (hexane:diethyl ether, 3:1, V/V) to obtain the desired title compound (185 mg, 31%) and its β isomer (250 mg, 41%) as a colorless amorphous substance.

$^1$H NMR (CDCl$_3$) δ: 1.17 (3H, d, J=5.9 Hz), 3.12 (1H, t, J=9.5 Hz), 3.19-3.25 (1H, m), 3.36 (1H, t, J=9.5 Hz), 3.44-3.50 (2H, m), 3.54-3.64 (3H, m), 3.75 (1H, t, J=9.5 Hz), 3.81-3.98 (4H, m), 4.19 (1H, dd, J=8.8, 4.4 Hz), 4.35-4.39 (3H, m), 4.45 (1H, J=11.7 Hz), 4.49-4.54 (3H, m), 4.59-4.61 (2H, m), 4.67-4.80 (6H, m), 4.84 (1H, d, J=11.0 Hz), 4.90 (1H, d, J=1.0 Hz), 4.94 (1H, d, J=11.7 Hz), 5.02 (1H, d, J=11.0 Hz), 5.18 (1H, d J=3.7 Hz), 6.88 (1H, br, d, J=7.3 Hz), 7.10-7.40 (40H, m);

MS (FAB) m/z: 1296 (M+Na)$^+$.

(18d) 4-Deoxy-4-trifluoroacetamido-3-O-{4-O-(6-deoxy-β-D-glucopyranosyl)-α-D-glucopyranosyl}-D-arabino side The compound (180 mg, 0.14 mmol) synthesized in Reference example 18 (18c) was dissolved in methanol (10 mL) and 20% palladium hydroxide-carbon (120 mg) was added thereto, followed by stirring of the mixture under a hydrogen atmosphere for 3 hours. After the catalyst was removed by Celite filtration, the solvent was distilled off under reduced pressure. The residue was purified using silica gel flash column chromatography (ethyl acetate:methanol, 4:1, V/V) to obtain the desired title compound (69 mg, 88.5%) as a colorless solid.

$^1$H NMR (D$_2$O) δ: 1.32 (3H, d, J=5.9 Hz), 3.19 (1H, t, J=9.5 Hz), 3.30-3.34 (2H, m), 3.46 (1H, t, J=9.5 Hz), 3.52 (1H, br, t, J=7.4 HZ), 3.59-3.67 (3H, m), 3.72-3.88 (3H, m), 3.97-4.07 (2H, m), 4.19-4.29 (1H, m), 4.48 (1H, d, J=8.0 Hz), 4.58-4.66 (2H, m), 5.24 (1H, br, s);

MS (FAB) m/z: 576 (M+Na)$^+$.

(18e) (2R,3R,4R)-4-Hydroxy-2-hydroxymethyl-3,4-dihydro-2H-pyrrol-3-yl 4-O-(6-deoxy-α-D-glucopyranosyl)-α-D-glucopyranoside The compound (47 mg, 0.085 mmol) synthesized in Reference example 18 (18d) was dissolved in water (10 mL) and an ion exchange resin Dowex-1×4 (OH$^-$) (3.0 g) was added thereto, followed by stirring of the mixture at room temperature for 1.5 hours. The ion exchange resin was removed and the solvent was distilled off under reduced pressure. The residue was purified using silica gel flash column chromatography (chloroform:methanol:water, 6:4:1, V/V) to obtain the desired title compound (8.0 mg, yield: 21.4%) as a colorless amorphous substance.

$^1$H NMR (D$_2$O) δ: 1.32 (3H, d, J=5.9 Hz), 3.16-3.21 (1H, m), 3.31-3.33 (1H, m), 3.45-3.52 (2H, m), 3.63-3.69 (2H, m), 3.80-3.96 (5H, m), 4.08 (1H, br, s), 4.25 (1H, dJ=4.9 Hz), 4.49 (1H, d, J=6.8 Hz), 4.94 (1H, d, J-4.9 Hz), 5.17 (1H, d, J=4.0 Hz), 7.68 (1H, br, s);

MS (FAB) m/z: 462 (M+Na)$^+$.

Reference Example 19

(2R,3R,4R)-4-Hydroxy-2-hydroxymethylpyrrolidin-3-yl 4-O-{4-O-(β-D-glucopyranosyl)-β-β-D-glucopyranosyl}-α-D-glucopyranoside (19a) (2R,3R,4R)-4-Benzyloxy-N-benzyloxycarbonyl-2-benzyloxymethylpyrrolidin-3-yl 4-O-acetyl-2,3,6-tri-O-benzyl-α-D-glucopyranoside 4-O-Acetyl-2,3,6-tri-O-benzylglucopyranoside (Agric. Biol. Chem, 1986, 50, 2261-2272) (2.21 g, 4.49 mmol) was dissolved in methylene chloride (45 mL), and trichloroacetonitrile (2.3 mL, 22.44 mmol) and 1,8-diazabicyclo[5.4.0]-7-undecene (65 μL, 0.44 mmol) were added thereto, followed by stirring of the mixture at room temperature for 1 hour. After the solvent was distilled off under reduced pressure, the residue was purified using silica gel flash column chromatography (hexane:ethyl acetate, 2:1, 1% triethylamine, V/V) to obtain imidate (2.06 g, 72.0%) as a yellow oil. The compound (2.00 g, 4.47 mmol) synthesized in Reference example 1 (1i) was dissolved in diethyl ether (100 mL), the imidate (2.06 g, 3.23 mmol) was added thereto and a solution of trimethylsilyl trifluoromethanesulfonate (40 μL, 0.22 mmol) in diethyl ether (2 mL) was added dropwise thereto, followed by stirring of the mixture at room temperature for 2 hours. Triethylamine (50 μL) was added to the reaction mixture and after the solvent was distilled off under reduced pressure, the mixture was diluted with ethyl acetate (20 mL) and the mixture was washed with a saturated aqueous sodium hydrogencarbonate solution (20 mL) and a saturated aqueous NaCl solution (10 mL). After the organic layer was dried with anhydrous sodium sulfate, the solvent was distilled off under reduced pressure. The residue containing the (α, β mixture was purified using silica gel flash column chromatography (hexane:ethyl acetate, 5:1, V/V) to isolate the desired title compound α form (1.93 g, 46.6%) as a colorless oil.

$^1$H NMR (400 MHz, CDCl$_3$) δ 1.82 (3H, s), 3.20-5.20 (26H, m), 7.10-7.40 (30H, m); MS (FAB) m/z: 922 (M+H)$^+$.

(19b) (2R,3R,4R)-4-Benzyloxy-N-benzyloxycarbonyl-2-benzyloxymethylpyrrolidin-3-yl 2,3,6-tri-O-benzyl-α-D-glucopyranoside The compound (1.57 g, 1.70 mmol) synthesized in Reference example 19 (19a) was dissolved in methanol (30 mL) and potassium carbonate (235 mg, 1.70 mmol) was added thereto, followed by stirring of the mixture at room temperature for 14 hours. The reaction mixture was diluted with ethyl acetate (10 mL) and the mixture was washed with a saturated aqueous sodium hydrogencarbonate solution (10 mL) and a saturated aqueous NaCl solution (10 mL). After the organic layer was dried with anhydrous sodium sulfate, the solvent was distilled off under reduced pressure. The residue was purified using silica gel flash column chromatography (hexane:ethyl acetate, 3:1, V/V) to obtain the desired title compound (1.41 g, 94.0%) as a colorless oily substance.

$^1$H NMR (400 MHz, CDCl$_3$): δ 3.40-5.20 (26H, m), 7.10-7.40 (30H, m);

MS (FAB) m/z: 880 (M+H)$^+$.

(19c) Allyl 2,3,6-O-tri-benzoyl-4-O-(2,3,4,6-tetra-O-benzoyl-β-D-glucopyranosyl)-D-glucopyranoside The compound (4.0 g, 10.46 mmol) synthesized in Reference example 2 (2a) was dissolved in pyridine (30 mL) and benzoyl chloride (12.1 mL, 104.24 mmol) was added thereto under ice-cooling, followed by stirring of the mixture at room temperature for 14 hours. The reaction mixture was poured into 10% aqueous hydrochloric acid solution (20 mL) and methylene chloride (20 mL), and the organic layer was washed with 10% aqueous hydrochloric acid solution (20 mL), a saturated aqueous sodium hydrogencarbonate solution (20 mL) and a saturated aqueous NaCl solution (20 mL). After it was dried with anhydrous sodium sulfate, the solvent was distilled off under reduced pressure. The residue was purified using silica gel flash column chromatography (hexane:ethyl acetate, 5:1-5:2, V/V) to obtain the desired title compound (8.10 g, yield: 70%) as a colorless oily substance.

$^1$H NMR (400 MHz, CDCl$_3$): δ 3.71-4.27 (6H, m), 4.44-4.51 (1H, m), 4.58-4.63 (1H, m), 4.72 (1H, d, J=6.4 Hz), 4.93-5.81 (10H, m), 7.17-8.11 (35H, m);

MS (FAB) m/z: 1111 (M+H)$^+$.

(19d) 2,3,6-O-tri-Benzoyl-4-O-(2,3,4,6-tetra-O-benzoyl-β-D-glucopyranosyl)-D-glucopyranoside The compound (8.10 g, 7.29 mmol) synthesized in Reference example 19 (19c) was dissolved in methanol (75 mL) and tetrahydrofuran (15 mL) and palladium chloride (II) (258 mg, 1.45 mmol) was added thereto, followed by stirring of the mixture at room temperature for 14 hours. After the reaction mixture was filtered through Celite, the solvent was distilled off under reduced pressure. The residue was purified using silica gel flash column chromatography (hexane:ethyl acetate, 3:1-2:1, V/V) to obtain the desired title compound (5.10 g, yield: 66%) as a pale yellow solid.

$^1$H NMR (400 MHz, CDCl$_3$): δ 2.96-3.13 (1H, m), 3.79-3.92 (2H, m), 4.05-4.25 (2H, m), 4.33-4.40 (1H, m), 4.47-4.50 (1H, m), 4.60-4.63 (1H, m), 4.89-6.15 (7H, m), 7.21-8.01 (35H, m);

MS (FAB) m/z: 1071 (M+H)$^+$.

(19e) (2R,3R,4R)-4-Benzyloxy-N-benzyloxycarbonyl-2-benzyloxymethylpyrrolidin-3-yl 2,3,6-tri-O-benzyl-4-O-{2,3,6-tri-O-benzoyl-4-O-(2,3,4,6-tetra-O-benzoyl-β-D-glucopyranosyl)-β-D-glucopyranosyl}-α-D-glucopyranoside The compound (414.4 mg, 0.39 mmol) synthesized in Reference example 19 (19d) was dissolved in methylene chloride (8 mL), and trichloroacetonitrile (200 μL, 1.99 mmol) and 1,8-diazabicyclo[5.4.0]-7-undecene (6 μL, 0.04 mmol) were added thereto, followed by stirring of the mixture at room temperature for 1 hour. After the solvent was distilled off under reduced pressure, the residue was purified using silica gel flash column chromatography (hexane:ethyl acetate, 2:1, 1% triethylamine, V/V) to obtain imidate (255.1 mg, 53.8%) as a colorless amorphous substance. The compound (185.3 mg, 0.21 mmol) synthesized in Reference Example 19 (19b) was dissolved in diethyl ether (8 mL), the imidate (225.1 mg, 0.21 mmol) was added thereto and a solution of trimethylsilyl trifluoromethanesulfonate (38 μL, 0.21 mmol) in diethyl ether (2 mL) was added dropwise thereto, followed by stirring of the mixture at room temperature for 2 hours. Triethylamine (35 μL) was added to the reaction mixture and after the solvent was distilled off under reduced pressure, the residue was diluted with ethyl acetate (10 mL) and the mixture was washed with a saturated aqueous sodium hydrogencarbonate solution (10 mL) and a saturated aqueous NaCl solution (10 mL). After the organic layer was dried with anhydrous sodium sulfate, the solvent was distilled off under reduced pressure. The residue was purified using silica gel flash column chromatography (hexane:ethyl acetate, 4:1-3:1, V/V) to isolate the desired title compound (295.8 mg, 72.9%) as a colorless amorphous substance.

$^1$H NMR (400 MHz, CDCl$_3$): δ 3.20-5.60 (40H, m), 7.10-7.40 (65H, m);
MS (FAB) m/z: 1932 (M+H)$^+$.

(19f) (2R,3R,4R)-4-Benzyloxy-N-benzyloxycarbonyl-2-benzyloxymethylpyrrolidin-3-yl 2,3,6-tri-O-benzyl-4-O-{4-O-(β-D-glucopyranosyl)-β-D-glucopyranosyl}-α-D-glucopyranoside The compound (295.8 mg, 0.15 mmol) synthesized in Reference example 19 (19e) was dissolved in methanol (6 mL) and potassium carbonate (20 mg, 0.14 mmol) was added thereto, followed by stirring of the mixture at room temperature for 6 hours. The reaction mixture was diluted with ethyl acetate (10 mL) and the mixture was washed with a saturated aqueous sodium hydrogencarbonate solution (10 mL) and a saturated aqueous NaCl solution (10 mL). The mixture was neutralized with methanol-hydrochloric acid and the solvent was distilled off under reduced pressure. The residue was purified using silica gel flash column chromatography (methylene chloride:methanol, 30:1-20:1-10:1, V/V) to obtain the desired title compound (100.7 mg, 55.8%) as a colorless solid.

$^1$H NMR (400 MHz, CD$_3$OD): δ 3.20-5.60 (40H, m), 7.10-7.40 (30H, m);
MS (FAB) m/z: 1204 (M+H)$^+$.

(19g) (2R,3R,4R)-4-Hydroxy-2-hydroxymethylpyrrolidin-3-yl 4-O-{4-O-β-D-glucopyranosyl)-β-D-glucopyranosyl}-α-D-glucopyranoside The compound (100.7 mg, 0.084 mmol) synthesized in Reference example 19 (19f) was dissolved in methanol (10 mL), and 36% hydrochloric acid (280 μL) and palladium hydroxide (100 mg) were added thereto, followed by stirring of the mixture at room temperature under a hydrogen atmosphere for 4 hours. After the reaction mixture was filtered through Celite, 18% ammonia water (1 mL) was added thereto. The solvent was distilled off under reduced pressure and the residue was purified using an ion exchange resin (Dowex 50w×8) column (water-1% ammonia water). Further, it was purified using silica gel flash column chromatography (ethyl acetate:methanol:water, 5:2:1-1:1:1, V/V) to obtain the desired title compound (10.0 mg, 19.2%) as a colorless solid.

$^1$H NMR (400 MHz, D$_2$O): δ 3.00-3.95 (25H, m), 4.38 (1H, d, J=8.1 Hz), 4.42 (1H, d, J=8.0 Hz), 5.00 (1H, d, J=2.6 Hz);
MS (FAB) m/z: 620 (M+H)$^+$.

Reference Example 20

(2R,3R,4R)-4-Hydroxy-2-hydroxymethylpyrrolidin-3-yl 4-O-{4-O-β-D-glucopyranosyl)-β-D-glucopyranosyl}-α-D-galactopyranoside (20a) (2R,3R,4R)-4-Benzyloxy-N-benzyloxycarbonyl-2-benzyloxymethylpyrrolidin-3-yl 4-O-acetyl-2,3,6-tri-O-benzyl-α-D-galactopyranoside 4-O-Acetyl-2,3,6-O-tri-benzyl-D-galactopyranoside (BCSJ, 1989, 62, 3549-3566) (1.60 g, 3.25 mmol) was dissolved in methylene chloride (30 mL), and trichloroacetonitrile (1.6 mL, 15.96 mmol) and 1,8-diazabicyclo[5.4.0]-7-undecene (50 μL, 0.33 mmol) were added thereto, followed by stirring of the mixture at room temperature for 1 hour. After the solvent was distilled off under reduced pressure, the residue was purified using silica gel flash column chromatography (hexane:ethyl acetate, 6:1, 1% triethylamine, V/V) to obtain imidate (1.37 g, 66%) as a yellow oil. The compound (0.96 g, 2.01 mmol) synthesized in Reference example 1 (1i) was dissolved in diethyl ether (50 mL), the imidate (1.37 g, 2.15 mmol) was added thereto and a solution of trimethylsilyl trifluoromethanesulfonate (20 μL, 0.11 mmol) in diethyl ether (2 mL) was added dropwise thereto, followed by stirring of the mixture at room temperature for 2 hours. Triethylamine (10 μL) was added to the reaction mixture and after the solvent was distilled off under reduced pressure, the mixture was diluted with ethyl acetate (20 mL) and the mixture was washed with a saturated aqueous sodium hydrogencarbonate solution (20 mL) and a saturated aqueous NaCl solution (10 mL). After the organic layer was dried with anhydrous sodium sulfate, the solvent was distilled off under reduced pressure. The residue containing the mixture of α and β forms was purified using silica gel flash column chromatography (hexane:ethyl acetate, 6:1-4:1, V/V) to isolate the desired title compound α form (0.98 g, 50%) as a colorless oil.

$^1$H NMR (400 MHz, CDCl$_3$): δ 2.02 (3H, s), 5.15-3.38 (25H, m), 5.61 (1H, m), 7.16-7.35 (30H, m);
MS (FAB) m/z: 922(M+H)$^+$.

(20b) (2R,3R,4R)-4-Benzyloxy-N-benzyloxycarbonyl-2-benzyloxymethylpyrrolidin-3-yl 2,3,6-tri-O-benzyl-α-D-galactopyranoside The compound (0.98 g, 1.06 mmol) synthesized in Reference example 20 (20a) was dissolved in methanol (20 mL) and potassium carbonate (147 mg, 1.06 mmol) was added thereto, followed by stirring of the mixture at room temperature for 14 hours. The reaction mixture was diluted with ethyl acetate (10 mL) and the mixture was washed with a saturated aqueous sodium hydrogencarbonate solution (10 mL) and a saturated aqueous NaCl solution (10 mL). After the organic layer was dried with anhydrous sodium sulfate, the solvent was distilled off under reduced pressure. The residue was purified using silica gel flash column chromatography (hexane:ethyl acetate, 4:1, V/V) to obtain the desired title compound (772.4 mg, 83%) as a colorless oily substance.

$^1$H NMR (400 MHz, CDCl$_3$): δ 2.70-2.81 (1H, m), 3.46-5.15 (26H, m), 7.15-7.37 (1H, m);

MS (FAB) m/z: 880 (M+H)$^+$.

(20c) (2R,3R,4R)-4-Benzyloxy-N-benzyloxycarbonyl-2-benzyloxymethylpyrrolidin-3-yl 2,3,6-tri-O-benzyl-4-O-{2,3,6-tri-O-benzyl-4-O-(2,3,4,6-tetra-O-benzoyl-β-D-glucopyranosyl)-β-D-glucopyranosyl}-α-D-galactopyranoside The compound (516.8 mg, 0.48 mmol) synthesized in Reference example 19 (19d) was dissolved in methylene chloride (10 mL), and trichloroacetonitrile (240 µL, 2.39 mmol) and 1,8-diazabicyclo[5.4.0]-7-undecene (7.5 µL, 0.05 mmol) were added thereto, followed by stirring of the mixture at room temperature for 1 hour. After the solvent was distilled off under reduced pressure, the residue was purified using silica gel flash column chromatography (hexane:ethyl acetate, 4:1, 1% triethylamine, V/V) to obtain imidate (376.9 mg, 65%) as a colorless amorphous substance. The compound (270.0 mg, 0.31 mmol) synthesized in Reference example 20 (20b) was dissolved in diethyl ether (15 mL), the imidate (376.9 mg, 0.31 mmol) was added thereto and a solution of trimethylsilyl trifluoromethanesulfonate (56 µL, 0.31 mmol) in diethyl ether (2 mL) was added dropwise thereto, followed by stirring of the mixture at room temperature for 2 hours. Triethylamine (50 µL) was added to the reaction mixture and after the solvent was distilled off under reduced pressure, the residue was diluted with ethyl acetate (20 mL) and the mixture was washed with a saturated aqueous sodium hydrogencarbonate solution (20 mL) and a saturated aqueous NaCl solution (10 mL). After the organic layer was dried with anhydrous sodium sulfate, the solvent was distilled off under reduced pressure. The residue was purified using silica gel flash column chromatography (hexane:ethyl acetate, 4:1-3:1, V/V) to isolate the desired title compound (390.8 mg, 65%) as a colorless amorphous substance.

$^1$H NMR (400 MHz, CDCl$_3$): δ 3.20-5.70 (40H, m), 7.10-7.40 (65H, m);

MS (FAB) m/z: 1932 (M+H)$^+$.

(20d) (2R,3R,4R)-4-Benzyloxy-N-benzyloxycarbonyl-2-benzyloxymethylpyrrolidin-3-yl 2,3,6-tri-O-benzyl-4-O-{4-O-β-D-glucopyranosyl)-β-D-glucopyranosyl}-α-D-galactopyranoside The compound (390.8 mg, 0.20 mmol) synthesized in Reference example 20 (20c) was dissolved in methanol (8 mL) and potassium carbonate (27.6 mg, 0.20 mmol) was added thereto, followed by stirring of the mixture at room temperature for 6 hours. The reaction mixture was diluted with ethyl acetate (10 mL) and the mixture was washed with a saturated aqueous sodium hydrogencarbonate solution (10 mL) and a saturated aqueous NaCl solution (10 mL). It was neutralized with methanol-hydrochloric acid and the solvent was distilled off under reduced pressure. The residue was purified using silica gel flash column chromatography (methylene chloride:methanol, 30:1-20:1-10:1, V/V) to obtain the desired title compound (146.5 mg, 61%) as a colorless solid.

$^1$H NMR (400 MHz, CD$_3$OD): δ 1.13 3.20-4.70 (37H, m), 4.97 (1H, d, J=3.6 Hz), 5.07 (2H, s), 7.23-7.39 (30H, m);

MS (FAB) m/z: 1226 (M+Na)$^+$.

(20e) (2R,3R,4R)-4-Hydroxy-2-hydroxymethylpyrrolidin-3-yl 4-O-{4-O-β-D-glucopyranosyl)-β-D-glucopyranosyl}-α-D-galactopyranoside The compound (146.5 mg, 0.12 mmol) synthesized in Reference example 20 (20d) was dissolved in methanol (15 mL) and 36% hydrochloric acid (420 µL) and palladium hydroxide (150 mg) were added thereto, followed by stirring of the mixture at room temperature under a hydrogen atmosphere for 4 hours. After the reaction mixture was filtered through Celite, 18% ammonia water (1 mL) was added thereto. The solvent was distilled off under reduced pressure and the residue was purified using an ion exchange resin (Dowex 50w×8) column (water-1% ammonia water). It was further purified using silica gel flash column chromatography (ethyl acetate:methanol:water, 5:2:1-1:1:1, V/V) to obtain the desired title compound (23.6 mg, 32%) as a colorless solid.

$^1$H NMR (400 MHz, D$_2$O): δ 3.17-3.87 (22H, m), 4.01 (1H, s), 4.11 (1H, s), 4.36 (1H, m), 4.38 (1H, d, J=8.0 Hz), 4.56 (1H, d, J=8.0 Hz), 5.04 (1H, s);

MS (FAB) m/z: 620 (M+H)$^+$.

Preparation Examples (1) Capsules

| Compound of Reference Example 2 | 15 mg |
|---|---|
| Pioglitazone | 5 mg |
| Lactose | 75 mg |
| Cornstarch | 58 mg |
| Magnesium stearate | 2 mg |
| Total | 155 mg |

Powders of each of the components indicated above were mixed well followed by passing through a 60 mesh sieve (the mesh standard is in compliance with the Tyler standard). 155 mg of the resulting powder were weighed out and filled into gelatin capsules (No. 3) to prepare capsules.

(2) Tablets

| Compound of Reference Example 2 | 15 mg |
|---|---|
| Nateglinide | 30 mg |
| Lactose | 35 mg |
| Cornstarch | 34 mg |
| Microcrystalline cellulose | 20 mg |
| Magnesium stearate | 1 mg |
| Total | 135 mg |

Powders of each of the components indicated above were mixed well, followed by pressing into tablets weighing 135 mg each. These tablets may be coated with glucose or a film as necessary.

(3) Tablets

| | |
|---|---|
| Compound of Reference Example 2 | 15 mg |
| Pioglitazone | 5 mg |
| Lactose | 35 mg |
| Cornstarch | 34 mg |
| Microcrystalline cellulose | 20 mg |
| Magnesium stearate | 1 mg |
| Total | 110 mg |

Powders of each of the components indicated above were mixed well, followed by pressing into tablets weighing 110 mg each. These tablets may be coated with sugar or a film as necessary.

(4) Tablets

| | |
|---|---|
| Compound of Reference Example 2 | 15 mg |
| Metformin | 200 mg |
| Lactose | 35 mg |
| Cornstarch | 34 mg |
| Microcrystalline cellulose | 20 mg |
| Magnesium stearate | 1 mg |
| Total | 305 mg |

Powders of each of the components indicated above were mixed well, followed by pressing into tablets weighing 305 mg each. These tablets may be coated with sugar or a film as necessary.

(5) Tablets

| | |
|---|---|
| Compound of Reference Example 2 | 15 mg |
| MK-0431 | 5 mg |
| Lactose | 35 mg |
| Cornstarch | 34 mg |
| Microcrystalline cellulose | 20 mg |
| Magnesium stearate | 1 mg |
| Total | 110 mg |

Powders of each of the components indicated above were mixed well, followed by pressing into tablets weighing 110 mg each. These tablets may be coated with sugar or a film as necessary.

The invention claimed is:

1. A pharmaceutical composition comprising a combination of an α-amylase inhibitor and at least one type of drug, wherein the α-amylase inhibitor is (2R,3R,4R)-4-hydroxy-2-(hydroxymethyl)pyrrolidin-3-yl 4-O-(6-deoxy-α-D-glucopyranosyl)-α-D-glucopyranoside, (2R,3R,4R)-4-hydroxy-2-(hydroxymethyl)pyrrolidin-3-yl 4-O-(6-deoxy-β-D-glucopyranosyl)-β-D-glucopyranoside, (2R,3R,4R)-4-hydroxy-2-(hydroxymethyl)pyrrolidin-3-yl 4-O-β-D-glucopyranosyl-α-D-glucopyranoside, (2R,3R,4R)-4-hydroxy-2-(hydroxymethyl)pyrrolidin-3-yl 4-O-(6-fluoro-6-deoxy-β-D-glucopyranosyl)-D-glucopyranoside or a pharmacologically acceptable salt or ester thereof, and wherein the at least one type of drug is selected from an insulin sensitizer, insulin secretagogue, biguanide drug, and an insulin preparation.

2. The pharmaceutical composition according to claim 1, comprising the combination of an α-amylase inhibitor and an insulin sensitizer.

3. A pharmaceutical composition for suppressing weight gain comprising the pharmaceutical composition according to claim 1, wherein the at least one type of drug includes an insulin sensitizer.

4. A pharmaceutical composition for suppressing cardiac hypertrophy comprising the pharmaceutical composition according to claim 1, wherein the at least one type of drug includes an insulin sensitizer.

5. The pharmaceutical composition according to claim 2, wherein the insulin sensitizer is a PPARγ agonist.

6. The pharmaceutical composition according to claim 2, wherein the insulin sensitizer is pioglitazone or rosiglitazone.

7. The pharmaceutical composition according to claim 2, wherein the insulin sensitizer is pioglitazone.

8. The pharmaceutical composition according to claim 1, comprising the combination of an α-amylase inhibitor and an insulin secretagogue.

9. The pharmaceutical composition according to claim 8, wherein the insulin secretagogue is a sulfonyl urea drug or a fast-acting insulin secretagogue.

10. The pharmaceutical composition according to claim 8, wherein the insulin secretagogue is glibenclamide, glimepiride or nateglinide.

11. The pharmaceutical composition according to claim 8, wherein the insulin secretagogue is nateglinide.

12. The pharmaceutical composition according to claim 1, comprising the combination of an α-amylase inhibitor and a biguanide drug.

13. A pharmaceutical composition for suppressing increases in lactic acid levels comprising the pharmaceutical composition according to claim 1, wherein the at least one type of drug includes a biguanide drug.

14. The pharmaceutical composition according to claim 12 or 13, wherein the biguanide drug is metformin, phenformin or buformin.

15. The pharmaceutical composition according to claim 12 or 13, wherein the biguanide drug is metformin.

16. The pharmaceutical composition according to claim 1 which is suitable for oral administration.

17. The pharmaceutical composition according to claim 1, comprising the combination of an α-amylase inhibitor and an insulin preparation.

18. The pharmaceutical composition according to claim 17, wherein the insulin preparation is fast-acting insulin.

19. The pharmaceutical composition according to claim 1, wherein the α-amylase inhibitor is (2R,3R,4R)-4-hydroxy-2-(hydroxymethyl)pyrrolidin-3-yl 4-O-(6-deoxy-α-D-glucopyranosyl)-α-D-glucopyranoside, (2R,3R,4R)-4-hydroxy-2-(hydroxymethyl)pyrrolidin-3-yl 4-O-(6-deoxy-β-D-glucopyranosyl)-α-D-glucopyranoside, or a pharmacologically acceptable salt or ester thereof.

20. The pharmaceutical composition according to claim 1, wherein the α-amylase inhibitor is (2R,3R,4R)-4-hydroxy-2-(hydroxymethyl)pyrrolidin-3-yl 4-O-(6-deoxy-β-D-glucopyranosyl)-α-D-glucopyranoside, or a pharmacologically acceptable salt or ester thereof.

21. The pharmaceutical composition according to claim 1 which is a drug for the treatment of diabetes.

22. The pharmaceutical composition according to claim 1 which is a drug for the treatment of postprandial hyperglycemia.

23. The pharmaceutical composition according to claim 1 for the treatment of diabetes having enhanced blood glucose lowering action as compared with single-drug administration.

24. A method for producing a pharmaceutical composition comprising combining an α-amylase inhibitor and at least one type of drug,
wherein the α-amylase inhibitor is (2R,3R,4R)-4-hydroxy-2-(hydroxymethyl)pyrrolidin-3-yl 4-O-(6-deoxy-α-D-glucopyranosyl)-α-D-glucopyranoside, (2R,3R,4R)-4-hydroxy-2-(hydroxymethyl)pyrrolidin-3-yl 4-O-(6-deoxy-β-D-glucopyranosyl)-α-D-glucopyranoside, (2R,3R,4R)-4-hydroxy-2-(hydroxymethyl)pyrrolidin-3-yl 4-O-β-D-glucopyranosyl-α-D-glucopyranoside, (2R,3R,4R)-4-hydroxy-2-(hydroxymethyl)pyrrolidin-3-yl 4-O-(6-fluoro-6-deoxy-β-D-glucopyranosyl)-D-glucopyranoside or a pharmacologically acceptable salt or ester thereof, and
wherein the at least one type of drug is selected from an insulin sensitizer, insulin secretagogue, biguanide drug, and an insulin preparation.

25. A method for treating diabetes comprising the enhancement of therapeutic effects and reduction of adverse side effects by administering to a patient to be treated a combination of an α-amylase inhibitor and at least one type of drug,
wherein the α-amylase inhibitor is (2R,3R,4R)-4-hydroxy-2-(hydroxymethyl)pyrrolidin-3-yl 4-O-(6-deoxy-α-D-glucopyranosyl)-α-D-glucopyranoside, (2R,3R,4R)-4-hydroxy-2-(hydroxymethyl)pyrrolidin-3-yl 4-O-(6-deoxy-β-D-glucopyranosyl)-α-D-glucopyranoside, (2R,3R,4R)-4-hydroxy-2-(hydroxymethyl)pyrrolidin-3-yl 4-O-β-D-glucopyranosyl-α-D-glucopyranoside, (2R,3R,4R)-4-hydroxy-2-(hydroxymethyl)pyrrolidin-3-yl 4-O-(6-fluoro-6-deoxy-β-D-glucopyranosyl)-D-glucopyranoside or a pharmacologically acceptable salt or ester thereof, and
wherein the at least one type of drug is selected from an insulin sensitizer, insulin secretagogue, biguanide drug, and an insulin preparation.

* * * * *